United States Patent
Sakamoto et al.

(10) Patent No.: US 9,969,812 B2
(45) Date of Patent: *May 15, 2018

(54) ANTI HUMAN NOTCH4 ANTIBODY

(71) Applicant: Eisai R&D Management Co., Ltd., Tokyo (JP)

(72) Inventors: Yoshimasa Sakamoto, Nishinomiya (JP); Yusuke Adachi, Tsukuba (JP); Junji Matsui, Tsukuba (JP); Yu Kato, Tsukuba (JP); Yoichi Ozawa, Tsukuba (JP); Takanori Abe, Tsukubamirai (JP); Ken Ito, Kashiwa (JP); Yuya Nakazawa, San Diego, CA (US); Sho Tachino, Tsukuba (JP); Katsuhisa Suzuki, Tsukubamirai (JP); Kishan Agarwala, Tsukuba (JP); Kana Hoshino, Kobe (JP); Masahiko Katayama, Fujieda (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/382,821

(22) Filed: Dec. 19, 2016

(65) Prior Publication Data

US 2017/0096493 A1    Apr. 6, 2017

Related U.S. Application Data

(63) Continuation of application No. 15/098,869, filed on Apr. 14, 2016, now Pat. No. 9,527,921.

(60) Provisional application No. 62/148,253, filed on Apr. 16, 2015.

(51) Int. Cl.
| | |
|---|---|
| *A61K 39/395* | (2006.01) |
| *C07K 16/28* | (2006.01) |
| *C07K 16/30* | (2006.01) |
| *C07K 14/705* | (2006.01) |
| *C07K 16/32* | (2006.01) |
| *A61K 31/337* | (2006.01) |
| *A61K 31/47* | (2006.01) |
| *A61K 33/24* | (2006.01) |
| *C12N 9/14* | (2006.01) |
| *C07K 14/71* | (2006.01) |
| *A61K 39/00* | (2006.01) |

(52) U.S. Cl.
CPC ............ *C07K 16/32* (2013.01); *A61K 31/337* (2013.01); *A61K 31/47* (2013.01); *A61K 33/24* (2013.01); *A61K 39/39558* (2013.01); *C07K 14/705* (2013.01); *C07K 16/28* (2013.01); *C07K 16/303* (2013.01); *C07K 16/3023* (2013.01); *C12N 9/14* (2013.01); *C12Y 301/03001* (2013.01); *A61K 2039/505* (2013.01); *C07K 2317/20* (2013.01); *C07K 2317/24* (2013.01); *C07K 2317/34* (2013.01); *C07K 2317/56* (2013.01); *C07K 2317/565* (2013.01); *C07K 2317/76* (2013.01); *C07K 2317/92* (2013.01); *C07K 2319/21* (2013.01); *C07K 2319/42* (2013.01)

(58) Field of Classification Search
CPC .......... A61K 2039/505; A61K 2300/00; A61K 39/39558; A61K 39/3955; A61K 39/395; A61K 39/39533; A61K 38/00; A61K 39/00; C07K 16/28; C07K 2317/76; C07K 2317/92; C07K 16/30; C07K 16/2863; C07K 2317/56; C07K 16/18; C07K 2317/565; C07K 2316/96; C07K 14/705; C07K 14/71; C07K 16/2866; C07K 16/286

See application file for complete search history.

(56) References Cited

U.S. PATENT DOCUMENTS

| | | | |
|---|---|---|---|
| 6,379,925 B1 | 4/2002 | Kitajewski et al. | |
| 9,527,921 B2 * | 12/2016 | Sakamoto | ................ C12N 9/14 |

FOREIGN PATENT DOCUMENTS

| | | |
|---|---|---|
| JP | 2004-527211 | 9/2004 |
| JP | 2005-511754 | 4/2005 |
| JP | 2006-513260 | 4/2006 |
| JP | 2007-526455 | 9/2007 |
| JP | 2009-513161 | 4/2009 |
| WO | WO 02/12447 | 2/2002 |
| WO | WO 03/050502 | 6/2003 |
| WO | WO 2004/013179 | 2/2004 |

(Continued)

OTHER PUBLICATIONS

Ahn, S. et al., "Notch1 and Notch4 are markers for poor prognosis of hepatocellular carcinoma", *Hepatobiliary Pancreat Dis Int.*, (2013) 12(3):286-94.

(Continued)

*Primary Examiner* — Bridget E Bunner
(74) *Attorney, Agent, or Firm* — Fish & Richardson P.C.

(57) ABSTRACT

The present invention provides an anti-human Notch4 antibody or a Notch4 binding fragment thereof that may have neutralizing activity against human Notch4, as well as a pharmaceutical composition comprising the same as the active ingredient. The present inventors obtained a mouse anti-human Notch4 antibody that has high neutralizing activity and binding affinity towards human Notch4 and determined the complementarity determining region (CDR) sequence of the mouse anti-human Notch4 antibody. This enabled the production of a humanized antibody comprising the variable region of heavy and light chains as well as the CDR sequence of the mouse anti-human Notch4 antibody.

14 Claims, 8 Drawing Sheets

(56) References Cited

FOREIGN PATENT DOCUMENTS

WO    WO 2005/074633    8/2005
WO    WO 2007/053648    5/2007

OTHER PUBLICATIONS

Al-Lazikani, B. et al., "Standard Conformations for the Canonical Structures of Immunoglobulins", *J. Mol. Biol.*, (1997) 273:927-948.
Benedito, R. et al., "The Notch Ligands Dll4 and Jagged1 Have Opposing Effects on Angiogenesis", *Cell*, (2009) 137:1124-1135.
Boo, Y-J. et al., "Vascular characterization of clear cell sarcoma of the kidney in a child: a case report and review", *J. Pediatric Surgery*, (2009) 44:2031-2036.
Curry, C.L. et al., "Gamma secretase inhibitor blocks Notch activation and induces apoptosis in Kaposi's sarcoma tumor cells", *Oncogene*, (2005) 24:6333-6344.
Dell' Albani, P. et al., "Differential patterns of NOTSCH1-4 receptor expression are markers of glioma cell differentiation", *Neuro-Oncology*, (2014) 16(2):204-216.
English Translation of the Written Opinion of the International Search Authority in Application No. PCT/2016/061961, dated Jun. 21, 2016, 2 pages.
Funahashi, Y. et al., "Eribulin mesylate reduces tumor microenvironment abnormality by vascular remodeling in preclinical human breast cancer models", *Cancer Sci.*, (2014) 105(10):1334-1342.
Gao et al., "Deregulated expression of Notch receptors in human hepatocellular carcinoma", Digestive Liver Dis 40:114-120, available online Oct. 4, 2007.
Geers et al., "Delta-like 4/Notch pathway is differentially regulated in benign and malignant thyroid tissues", Thyroid 21(12):1323-1330, 2011.
Gramantieri et al., "Aberrant Notch3 and Notch4 expression in human hepatocellular carcinoma", Liver Int 27:997-1007, 2007.
Hardy, K.M. et al., "Regulation of the Embryonic Morphogen Nodal by Notch4 Facilitates Manifestation of the Aggressive Melanoma Phenotype", *Cancer Res.*, (2010) 70(24):10340-50.
International Search Report from Application No. PCT/2016/061961, dated Jun. 21, 2016, 11 pages.
Jhappan, C. et al., "Expression of an activated Notch-related int-3 transgene interferes with cell differentiation and induces neoplastic transformation in mammary and salivary glands", *Genes & Development.*, (1992) 6:345-55.
Justilien, V. et al., "Matrix Metalloproteinase-10 Is Required for Lung Cancer Stem Cell Maintenance, Tumor Initiation and Metastatic Potential", *PloS ONE*, (2012) 7(4) e35040:1-12.
Kamdje, A.H.N. et al., "Notch-3 and Notch-4 signaling rescue from apoptosis human B-ALL cells in contact with human bone marrow-derived mesenchymal stromal cells", (2011) *Blood*, 118:380-389.
Kamdje, A.H.N. et at, "Role of stromal cell-mediated Notch signaling in CLL resistance to chemotherapy", *Blood Cancer Journal*, (2012) 2(5):e73.
Kontennann, R.E., "Dual targeting strategies with bispecific antibodies", *mAbs*, (2012) 4:182-197.
Nagamatsu, I. et al., "NOTCH4 Is a Potential Therapeutic Target for Triple-negative Breast Cancer", *Anticancer Research*, (2014) 34:69-80.
Qian C. et al., "Notch4 promotes gastric cancer growth through activation of Wnt1/β-catenin signaling", *Mol Cell Biochem*, (2015) 401:165-174.
Radtke, F. et al., "Notch regulation of lymphocyte development and function", *Nature Immunology*, (2004) 5:247-253.
Ridgway, J. et al., "Inhibition of Dll4 signalling inhibits tumour growth by deregulating angiogenesis", *Nature*, (2006) 444:1083-1087.
Riella, L.V. et al., "Blockade of Notch Ligand Delta 1 Promotes Allograft Survival by Inhibiting Alloreactive Th1 Cells and Cytotoxic T Cell Generation", *The Journal of Immunology* 2011, 187:4629-4638.

* cited by examiner

US 9,969,812 B2

ANTI HUMAN NOTCH4 ANTIBODY

TECHNICAL FIELD

The present invention relates to an antibody that binds to human Notch4.

BACKGROUND ART

Notch is a molecule that contributes to the determination of fate of cells of various tissues, and is indicated to be involved in e.g. differentiation, proliferation, and survival during each stages of early developmental stage, embryonic stage, and after birth. Four types of receptors including Notch1, Notch2, Notch3, and Notch4 as well as five types of ligands including Jagged1, Jagged2, DLL1, DLL3, and DLL4 are reported as the Notch family. When a Notch receptor expressed on an adjacent cell binds with a Notch ligand, the NRR domain present in the lower extracellular domain of the receptor is cleaved by TACE, and due to the structural change of the intracellular domain thus caused, the intracellular domain is cleaved by γ secretase. The Notch Intracellular (NIC) domain formed as a result migrates into the nucleus, forms a heterodimer with transcription factor CSL, and target molecules such as the aHes family or the Hey family are induced and expressed. These downstream molecules further induce and express various genes, and as a result, the Notch signal contributes to e.g. the maintenance of stem cells or progenitor cells, differentiation, cell cycle arrest, and cell fate determination (Non-Patent Literature 1).

Notch is also known to be involved in tumor formation. Notch1 mutation due to t(7; 9) chromosomal translocation was first reported as being related to the onset of pre-T cell acute lymphoblastic leukemia (T-ALL). Moreover, the genome insertion site of Mouse Mammary Tumor Virus (MMTV) which is a spontaneous tumor onset model is reported to be Int3 (Notch4 intracellular domain), and it is reported that epithelial cell cancer such as breast cancer or salivary gland cancer are induced in a transgenic mouse where Int3 was force expressed (Non-Patent Literature 2). Notch4 is also reported to be related to the oncogenesis, progression, or metastasis of breast cancer (Non-Patent Literature 3), melanoma (Non-Patent Literature 4), stomach cancer (Non-Patent Literature 5), B-cell acute lymphocytic leukemia (B-ALL) (Non-Patent Literature 6), chronic lymphocytic leukemia (CLL) (Non-Patent Literature 7), glioma (Non-Patent Literature 8), hepatocellular carcinoma (Non-Patent Literature 9), lung cancer (Non-Patent Literature 10), renal cancer (Non-Patent Literature 11), Kaposi's sarcoma (Non-Patent Literature 12), and the like in humans.

The Notch signal also contributes intratumoral neovascularization. Notch1 and Notch4 are expressed as Notch receptors in vascular endothelial cells, and the expression of DLL4 and Jagged1 are confirmed as ligands. Tip cells present at the tip of new blood vessels highly express DDL4 with VEGF stimulation, and blood vessels are extended by sending a signal to the Notch receptor of the adjacent Stalk cell. On the other hand, Jagged1 competes with DLL4 for the Notch receptor and inhibits the binding of DLL4 with the Notch receptor. Since the signal from Jagged1 is weak compared to that from DLL4, the Notch signal is suppressed by binding with Jagged1. The intensity of the Notch signal is adjusted by the spatially differing expression patterns of these two ligands to control neovascularization (Non-Patent Literature 13).

Production of a DLL4 inhibitory antibody has been reported, in which when the signal from DLL4 is inhibited with a DLL4 inhibitory antibody, immature angiogenesis without bloodstream is enhanced inside a tumor and inhibition of tumor proliferation is induced. This is a completely different phenomenon from when a VEGF inhibitor inhibits the proliferation of vascular endothelial cells to suppress angiogenesis, and the Notch signal is gathering attention as a novel target for neovascularization inhibitors (Non-Patent Literature 14).

CITATION LIST

[Non-Patent Literature 1] Radtke et al. (2004), Nature Immunology 5, 247-53.
[Non-Patent Literature 2] Jhappan et al. (1992), Genes Dev. 6, 345-55
[Non-Patent Literature 3] Nagamatsu et al. (2014), Anticancer Res. 34, 69-80
[Non-Patent Literature 4] Hardy et al. (2010), Cancer Res. 70, 10340-50
[Non-Patent Literature 5] Qian et al. (2015), Mol Cell Biochem. 401, 165-74
[Non-Patent Literature 6] Nwabo Kamdje et al. (2011), Blood 118, 380-9
[Non-Patent Literature 7] Nwabo Kamdje et al. (2012), Blood Cancer Journal 2, e73
[Non-Patent Literature 8] Dell'Albani et al. (2012), Neuro-Oncology 16, 204-16
[Non-Patent Literature 9] Ahn et al. (2013), Hepatobiliary Pancreat Dis Int. 12, 286-94
[Non-Patent Literature 10] Justilien et al. (2012), PLoS ONE 7, e35040
[Non-Patent Literature 11] Boo et al. (2009), J Pediatr Surg. 44, 2031-6
[Non-Patent Literature 12] Curry et al. (2005), Oncogene 24, 6333-44
[Non-Patent Literature 13] Benedito et al. (2009), Cell 137, 1124-35
[Non-Patent Literature 14] Ridgway et al. (2006), Nature 444, 1083-7

SUMMARY OF THE INVENTION

Problems to be Solved by the Invention

The object of the present invention is to provide an anti-human Notch4 antibody or a Notch4 binding fragment thereof that may have neutralizing activity against human Notch4, as well as a pharmaceutical composition comprising the same as the active ingredient.

Means for Solving the Problems

As a result of extensive investigation to solve the above problems, the present inventors succeeded in obtaining a mouse anti-human Notch4 antibody that has high neutralizing activity and binding affinity towards human Notch4. Moreover, by determining the complementarity determining region (CDR) sequence of said mouse anti-human Notch4 antibody, the present inventors enabled the production of a humanized antibody comprising the variable region of heavy and light chains as well as the CDR sequence of said mouse anti-human Notch4 antibody to complete the present invention.

In other words, in one embodiment, the present invention relates to the following inventions.
(1) An anti-Notch4 antibody or a Notch4 binding fragment thereof comprising:

(a) a heavy chain CDR1 comprising the amino acid sequence of SEQ ID NO. 15 or 16;
(b) a heavy chain CDR2 comprising the amino acid sequence of SEQ ID NO. 17 or 18;
(c) a heavy chain CDR3 comprising the amino acid sequence of SEQ ID NO. 19;
(d) a light chain CDR1 comprising the amino acid sequence of SEQ ID NO. 20;
(e) a light chain CDR2 comprising the amino acid sequence of SEQ ID NO. 21; and
(f) a light chain CDR3 comprising the amino acid sequence of SEQ ID NO. 22.

(2) The anti-Notch4 antibody or a Notch4 binding fragment thereof according to (2), wherein said antibody or a Notch4 binding fragment thereof comprises heavy and light chains and is selected from any of the following (i)-(vii):
  (i) an antibody in which the variable region of said heavy chain comprises the amino acid sequence of SEQ ID NO. 33 and the variable region of said light chain comprises the amino acid sequence of SEQ ID NO. 45,
  (ii) an antibody in which the variable region of said heavy chain comprises the amino acid sequence of SEQ ID NO. 35 and the variable region of said light chain comprises the amino acid sequence of SEQ ID NO. 45,
  (iii) an antibody in which the variable region of said heavy chain comprises the amino acid sequence of SEQ ID NO. 33 and the variable region of said light chain comprises the amino acid sequence of SEQ ID NO. 47,
  (iv) an antibody in which the variable region of said heavy chain comprises the amino acid sequence of SEQ ID NO. 35 and the variable region of said light chain comprises the amino acid sequence of SEQ ID NO. 49,
  (v) an antibody in which the variable region of said heavy chain comprises the amino acid sequence of SEQ ID NO. 33 and the variable region of said light chain comprises the amino acid sequence of SEQ ID NO. 51,
  (vi) an antibody in which the variable region of said heavy chain comprises the amino acid sequence of SEQ ID NO. 39 and the variable region of said light chain comprises the amino acid sequence of SEQ ID NO. 45, and
  (vii) an antibody in which the variable region of said heavy chain comprises the amino acid sequence of SEQ ID NO. 35 and the variable region of said light chain comprises the amino acid sequence of SEQ ID NO. 47.

(3) The anti-Notch4 antibody or a Notch4 binding fragment thereof according to (2), wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 45.

(4) The anti-Notch4 antibody or a Notch4 binding fragment thereof according to (2), wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 45.

(5) The anti-Notch4 antibody or a Notch4 binding fragment thereof according to (2), wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 47.

(6) The anti-Notch4 antibody or a Notch4 binding fragment thereof according to (2), wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 49.

(7) The anti-Notch4 antibody or a Notch4 binding fragment thereof according to (2), wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 51.

(8) The anti-Notch4 antibody or a Notch4 binding fragment thereof according to (2), wherein said antibody or a Notch4 binding fragment thereof comprises heavy and light chains, and the variable region of said heavy chain comprises the amino acid sequence of SEQ ID NO. 39 and the variable region of said light chain comprises the amino acid sequence of SEQ ID NO. 45.

(9) The anti-Notch4 antibody or a Notch4 binding fragment thereof according to (2), wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 47.

(10) The antibody or a Notch4 binding fragment thereof according to any one of (1)-(9), wherein the constant region of said heavy chain and the constant region of said light chain comprise a human antibody-derived sequence.

(11) The anti-Notch4 antibody or a Notch4 binding fragment thereof according to (10), wherein the constant region of the heavy chain comprises the constant region of human IgG.

(12) The anti-Notch4 antibody or a Notch4 binding fragment thereof according to (11), wherein said constant region of human IgG is the constant region of human IgG2.

(13) The anti-Notch4 antibody or a Notch4 binding fragment thereof according to (12), wherein said constant region of human IgG2 has a mutation V234A and/or G237A.

(14) The anti-Notch4 antibody or a Notch4 binding fragment thereof according to (10), wherein the lysine residue at the carboxy terminal of the constant region of said heavy chain is artificially removed.

(15) The anti-Notch4 antibody or a Notch4 binding fragment thereof according to (10), wherein the constant region of said light chain comprises the constant region of human Igκ.

(16) A pharmaceutical composition comprising the anti-Notch4 antibody or a Notch4 binding fragment thereof according to any one of (1)-(15).

(17) The pharmaceutical composition according to (16) which further comprises a pharmaceutically acceptable carrier.

(18) The pharmaceutical composition according to (17) which is used for treatment of non-small cell lung cancer.

(19) The pharmaceutical composition according to (17) which is used for treatment of thyroid cancer.

(20) The pharmaceutical composition according to (17) which is used for treatment of prostate cancer.

(21) The pharmaceutical composition according to (17) which is used for treatment of hepatocellular carcinoma.

In other embodiments, the present invention also relates to the following inventions.

(1') An anti-Notch4 antibody or a Notch4 binding fragment thereof, wherein said antibody or a Notch4 binding fragment thereof comprises heavy and light chains and is selected from any of the following (i)-(vii):

(i) an antibody in which the variable region of said heavy chain comprises the amino acid sequence of SEQ ID NO. 33 and the variable region of said light chain comprises the amino acid sequence of SEQ ID NO. 45, (ii) an antibody in which the variable region of said heavy chain comprises the amino acid sequence of SEQ ID NO. 35 and the variable region of said light chain comprises the amino acid sequence of SEQ ID NO. 45, (iii) an antibody in which the variable region of said heavy chain comprises the amino acid sequence of SEQ ID NO. 33 and the variable region of said light chain comprises the amino acid sequence of SEQ ID NO. 47, (iv) an antibody in which the variable region of said heavy chain comprises the amino acid sequence of SEQ ID NO. 35 and the variable region of said light chain comprises the amino acid sequence of SEQ ID NO. 49, (v) an antibody in which the variable region of said heavy chain comprises the amino acid sequence of SEQ ID NO. 33 and the variable region of said light chain comprises the amino acid sequence of SEQ ID NO. 51, (vi) an antibody in which the variable region of said heavy chain comprises the amino acid sequence of SEQ ID NO. 39 and the variable region of said light chain comprises the amino acid sequence of SEQ ID NO. 45, and (vii) an antibody in which the variable region of said heavy chain comprises the amino acid sequence of SEQ ID NO. 35 and the variable region of said light chain comprises the amino acid sequence of SEQ ID NO. 47.

(2') The anti-Notch4 antibody or a Notch4 binding fragment thereof according to (1'), wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 45.

(3') The anti-Notch4 antibody or a Notch4 binding fragment thereof according to (1'), wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 45.

(4') The anti-Notch4 antibody or a Notch4 binding fragment thereof according to (1'), wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 47.

(5') The anti-Notch4 antibody or a Notch4 binding fragment thereof according to (1'), wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 49.

(6') The anti-Notch4 antibody or a Notch4 binding fragment thereof according to (1'), wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 51.

(7') The anti-Notch4 antibody or a Notch4 binding fragment thereof according to (1'), wherein said antibody or a Notch4 binding fragment thereof comprises heavy and light chains, and the variable region of said heavy chain comprises the amino acid sequence of SEQ ID NO. 39 and the variable region of said light chain comprises the amino acid sequence of SEQ ID NO. 45.

(8') The anti-Notch4 antibody or a Notch4 binding fragment thereof according to (1'), wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 47.

(9') The antibody or a Notch4 binding fragment thereof according to any one of (1')-(8'), wherein the constant region of said heavy chain and the constant region of said light chain comprise a human antibody-derived sequence.

(10') The antibody or a Notch4 binding fragment thereof according to (9'), wherein the constant region of the heavy chain comprises the constant region of human IgG.

(11') The antibody or a Notch4 binding fragment thereof according to (10'), wherein said constant region of human IgG is the constant region of human IgG2.

(12') The antibody or a Notch4 binding fragment thereof according to (11'), wherein said constant region of human IgG2 has a mutation V234A and/or G237A.

(13') The antibody or a Notch4 binding fragment thereof according to (9'), wherein the lysine residue at the carboxy terminal of the constant region of said heavy chain is artificially removed.

(14') The antibody or a Notch4 binding fragment thereof according to (9'), wherein the constant region of said light chain comprises the constant region of human Igκ.

(15') A pharmaceutical composition comprising the anti-Notch4 antibody or a Notch4 binding fragment thereof according to any one of (1')-(14').

(16') The pharmaceutical composition according to (15') which further comprises a pharmaceutically acceptable carrier.

(17') The pharmaceutical composition according to (16') which is used for treatment of non-small cell lung cancer.

(18') The pharmaceutical composition according to (16') which is used for treatment of thyroid cancer.

(19') The pharmaceutical composition according to (16') which is used for treatment of prostate cancer.

(20') The pharmaceutical composition according to (16') which is used for treatment of hepatocellular carcinoma.

In other embodiments, the present invention further relates to the following inventions.

(1") An anti-Notch4 antibody or a Notch4 binding fragment thereof, wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 45.

(2") An anti-Notch4 antibody or a Notch4 binding fragment thereof, wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 45.

(3") An anti-Notch4 antibody or a Notch4 binding fragment thereof, wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 47.

(4") An anti-Notch4 antibody or a Notch4 binding fragment thereof, wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 49.

(5") An anti-Notch4 antibody or a Notch4 binding fragment thereof, wherein said antibody or a Notch4 binding fragment thereof comprises heavy and light chains, and the variable region of said heavy chain comprises the amino acid sequence of SEQ ID NO. 33 and the variable region of said light chain comprises the amino acid sequence of SEQ ID NO. 51.

(6") An anti-Notch4 antibody or a Notch4 binding fragment thereof, wherein said antibody or a Notch4 binding fragment thereof comprises heavy and light chains, and the variable region of said heavy chain comprises the amino acid sequence of SEQ ID NO. 39 and the variable region of said light chain comprises the amino acid sequence of SEQ ID NO. 45.

(7") An anti-Notch4 antibody or a Notch4 binding fragment thereof, wherein said antibody or a Notch4 binding fragment thereof comprises heavy and light chains, and the variable region of said heavy chain comprises the amino acid sequence of SEQ ID NO. 35 and the variable region of said light chain comprises the amino acid sequence of SEQ ID NO. 47.

(8") The antibody or a Notch4 binding fragment thereof according to any one of (1")-(7"), wherein the constant region of said heavy chain and the constant region of said light chain comprise a human antibody-derived sequence.

(9") The antibody or a Notch4 binding fragment thereof according to (8"), wherein the constant region of the heavy chain comprises the constant region of human IgG.

(10") The antibody or a Notch4 binding fragment thereof according to (9"), wherein said constant region of human IgG is the constant region of human IgG2.

(11") The antibody or a Notch4 binding fragment thereof according to (10"), wherein said constant region of human IgG2 has a mutation V234A and/or G237A.

(12") The antibody or a Notch4 binding fragment thereof according to (10"), wherein the lysine residue at the carboxy terminal of the constant region of said heavy chain is artificially removed.

(13") The antibody or a Notch4 binding fragment thereof according to (8"), wherein the constant region of said light chain comprises the constant region of human Igκ.

(14") A pharmaceutical composition comprising the anti-Notch4 antibody or a Notch4 binding fragment thereof according to any one of (1")-(13").

(15") The pharmaceutical composition according to (14") which further comprises a pharmaceutically acceptable carrier.

(16") The pharmaceutical composition according to (15") which is used for treatment of non-small cell lung cancer.

(17") The pharmaceutical composition according to (15") which is used for treatment of thyroid cancer.

(18") The pharmaceutical composition according to (15") which is used for treatment of prostate cancer.

(19") The pharmaceutical composition according to (15") which is used for treatment of hepatocellular carcinoma.

An invention of any combination of one of more characteristics of the present invention listed above is also encompassed in the scope of the present invention.

BRIEF DESCRIPTION OF THE DRAWINGS

FIG. 2A shows the change in relative tumor volume (RTV) for each group with tail vein administration of IgG at 10 mg/kg for Control or Antibody B at 1, 3, or 10 mg/kg in a Calu6 xenograft model (N=8, mean±standard error). FIG. 2B shows the result of determining the Hoechst fluorescence area for tumors sampled at the end of administration test (Day 8) (N=8 mean±standard error) (*P<0.05 vs Control IgG administration group (Dunnett test)).

(FIG. 8A) human Notch1-NRR-SEAP-His, (FIG.

Figure 8A:
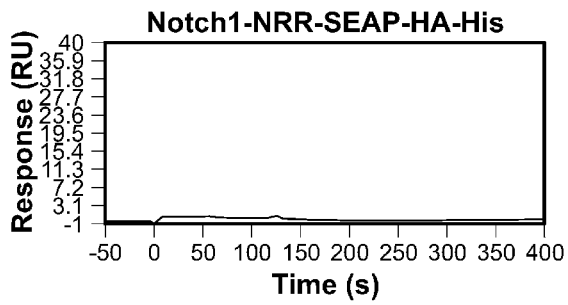
FIGS. 8A-8D show the overlaid sensorgram of the interaction between Antibody B and human Notch NRR domains.
Figure 8B:
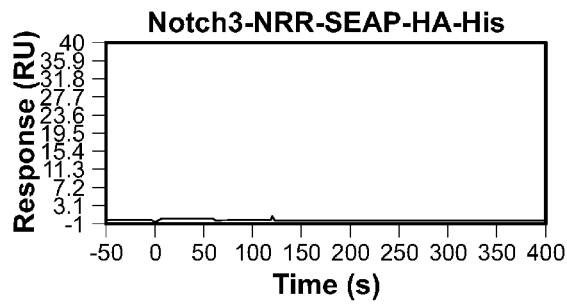
Figure 8C:
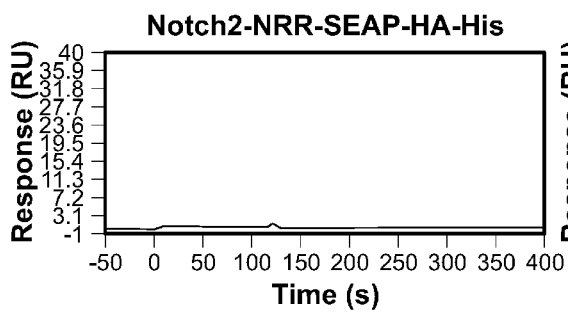
Figure 8D:
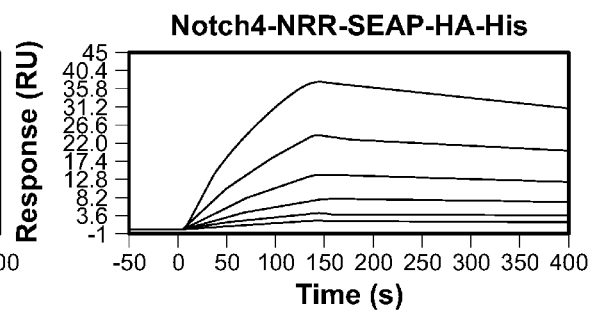

8B) human Notch2-NRR-SEAP-His, (FIG. 8C) human Notch3-NRR-SEAP-His, and (FIG. 8D) human Notch4-NRR-SEAP-His.

DESCRIPTION OF EMBODIMENTS

An antibody herein may refer to an immunoglobulin molecule that can bind specifically to a target such as a sugar, a polynucleotide, a lipid, a polypeptide, and a protein via at least one antigen recognition site positioned on the variable region of the immunoglobulin molecule. An antibody may refer to a complete polyclonal or monoclonal antibody.

The antibody may be of any class such as IgG, IgA, or IgM (or a subclass thereof) etc. and is not limited to a particular class. An immunoglobulin is classified to different classes depending on the antibody amino acid sequence of the constant region of the heavy chain (sometimes referred to as the H chain). There are five major immunoglobulin classes: IgA, IgD, IgE, IgG, and IgM, some of which may be further classified into subclasses (isotypes) such as $IgG_1$, $IgG_2$, $IgG_3$, $IgG_4$, $IgA_1$, and $IgA_2$. The constant regions of the heavy chain corresponding to the different classes of immunoglobulin are referred to as $\alpha$, $\delta$, $\varepsilon$, $\gamma$, and $\mu$, respectively. Moreover, the types of the light chain (sometimes referred to as the L chain) of the antibody include $\lambda$, and $\kappa$ chains.

In one aspect, the anti-human Notch4 antibody of the present invention may be an IgG antibody, for example an $IgG_1$ antibody or an $IgG_2$ antibody etc. Moreover, in some cases, the anti-Notch4 antibody of the present invention or an antigen binding fragment thereof may be in the form of a monomer, a dimer, or a multimer.

The antigen binding fragment of an antibody herein is not particularly limited, as long as it is a functional and structural fragment of said antibody and retains the binding ability to an antigen that can be bound by said antibody. Examples of the antigen binding fragment of an antibody include, but are not limited to, Fab, Fab', F(ab')2, Fv, single-chain (ScFv), variants thereof, a fusion protein comprising an antibody portion, other modified structures of an immunoglobulin molecule comprising the antigen recognition site, and the like.

The antigen binding fragment of an antibody can be obtained for example via proteolytic digestion of a complete antibody, or may be directly produced by a recombinant host cell (e.g. an eukaryote such as a yeast cell, a plant cell, an insect cell, or a mammalian cell, or a prokaryote such as E. coli). For example, an $F(ab')_2$ fragment may be formed by collecting Fab'-SH fragments directly from E. coli and subjecting them to chemical binding. $F(ab')_2$ may also be formed by using a leucine zipper GCN4 which promotes the assembly of an $F(ab')_2$ molecule. Moreover, an automatic synthesizer can be used when producing scFv with a chemical synthesis technology. An appropriate plasmid comprising a polynucleotide encoding scFv can be introduced to an appropriate host cell (e.g. an eukaryote such as a yeast cell, a plant cell, an insect cell, or a mammalian cell, or a prokaryote such as E. coli) when producing scFv with a genetic recombination technology. The polynucleotide encoding the scFv of interest may be produced by a well-known manipulation such as ligation of polynucleotides. The scFv produced as a result may be isolated using a standard protein purification technology well-known in the art.

The variable region of an antibody may mean the variable region of the antibody light chain and/or the variable region of the antibody heavy chain, and the constant region of an antibody may mean the constant region of the antibody light chain and/or the constant region of the antibody heavy chain. The variable region of heavy and light chains each consists of four framework regions (FR) joined by three CDRs also known as hypervariable regions. The CDR in each chain is kept in the vicinity by a FR, and together with the CDR in the other chain contributes to the formation of the antigen binding site of the antibody. Technologies to determine CDRs include, but are not limited to, e.g. (1) an approach based on cross-species sequence variability (such as Kabat et al, Sequences of Proteins of Immunological Interest, 5th ed., 1991, National Institutes of Health, Bethesda Md.); and (2) an approach based on crystal structure research of antigen-antibody complexes (Al-lazikani et al., 1997 J. Molec. Biol. 273:927-948). These and other approaches may be employed in combination.

The term "binds specifically to" is a term well-known in the field to those skilled in the art, and methods for determining specific binding of an antibody etc. to an antigen or an epitope are also well-known. For example, it is understood that an antibody or an antigen binding fragment thereof that binds specifically to the epitope of Notch4 can bind to said Notch4 epitope with a higher affinity and binding activity, more rapidly, and/or, for a longer duration than to other epitope or non-epitope sites. However, an antibody or an antigen binding fragment thereof that binds specifically to a first target is not excluded from binding specifically to a second target.

A monoclonal antibody may mean an antibody that is obtained from a population of substantially uniform antibodies. In other words, individual antibodies contained in this population are identical except for a slight amount of naturally existing mutants that may be present. Monoclonal antibodies are directed to a single antigen site, and are very specific. Further, in contrast to a typical polyclonal antibody that targets different antigens or different epitopes, each monoclonal antibody targets a single epitope of the antigen. The modifier "monoclonal" indicates the property of an antibody that is obtained from a substantially uniform antibody population, and is not to be construed as being limited to requiring antibody production by a particular method.

The anti-Notch4 antibody of the present invention or an antigen binding fragment thereof may be a chimeric antibody, a humanized antibody, a human antibody, a non-human mammal (such as mouse, rat, rabbit, cow, horse, and goat) antibody, or an antigen binding fragment thereof. A chimeric antibody is an antibody having e.g. the variable region of a non-human (such as mouse or rat) antibody introduced into the constant region of a human antibody, and may refer to e.g. an antibody wherein the variable region is derived from a non-human antibody and constant region is derived from a human antibody. A humanized antibody is an antibody having e.g. the hypervariable region (also referred to as complementarity determining region (CDR)) of a non-human antibody introduced into a human antibody, and may refer to e.g. an antibody wherein the CDR is derived from a non-human antibody and other antibody regions are derived from a human antibody. Note that in the present invention, the boundary between a chimeric antibody and a humanized antibody does not necessarily need to be clear, and an antibody may be in a state that may be called both a chimeric antibody and a humanized antibody.

Needless to say, the chimeric or humanized antibody exemplified above which has been appropriately modified (such as by modification of the antibody or partial substitution, addition, or deletion of the amino acid sequence of the antibody) while retaining the function of said antibody (or in order to add to or improve the function of said antibody) is also encompassed in the antibody of the present invention. More specifically, an antibody modified by the POTELLIGENT™ technology in order to increase the antibody-dependent cellular cytotoxicity ((ADCC) activity) of the antibody bound to the target, an antibody modified by the COMPLEGENT™ technology in order to increase the complement-dependent cytotoxicity ((CDC) activity) of the antibody, or an antibody modified by combination use of these technologies are also encompassed in the scope of the present invention. Moreover, an antibody having the lysine (Lys) located at the carboxy terminal (C-terminal) of the heavy chain deleted by an artificial method such as genetic modification in order to reduce the ununiformity of antibodies produced by antibody-producing cells is also encompassed in the scope of the present invention. Further, a bispecific antibody possessing the antibody binding site having the CDR sequence of the antibody of the present invention together with an antigen binding site that binds to a different antigen (Kontermann (2012), mAbs 4, 182-97) is also encompassed in the scope of the present invention.

The anti-Notch4 antibody of the present invention or an antigen binding fragment thereof may be modified as desired. The modification of the anti-Notch4 antibody of the present invention or an antigen binding fragment thereof may be a modification that changes (a) the three dimensional structure of the amino acid sequence at the modified region such as sheet or helix conformation; (b) the charge or hydrophobicity state of the molecule at the target site; or (c) the effect of modification on the side chain volume, or a modification where these changes are not clearly observed.

The modification of the anti-Notch4 antibody of the present invention or an antigen binding fragment thereof may be achieved by e.g. substitution, deletion, and addition etc. of the configuring amino acid residues.

An amino acid herein is employed in its broadest meaning, and includes not only natural amino acids such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro), but also non-natural amino acids such as amino acid variants and derivatives. Those skilled in the art shall naturally recognize in light of this broad definition that examples of amino acids herein include L-amino acids; D-amino acids; chemically modified amino acids such as amino acid variants and derivatives; amino acids that are not materials configuring proteins in vivo such as norleucine, β-alanine, and ornithine; and chemically synthesized compounds having properties of amino acids well-known to those skilled in the art. Examples of a non-natural amino acid include α-methylamino acids (such as α-methylalanine), D-amino acids (such as D-aspartic acid and D-glutamic acid), histidine-like amino acids (such as 2-amino-histidine, β-hydroxy-histidine, homohistidine, α-fluoromethyl-histidine, and α-methyl-histidine), amino acids having excess methylene in the side chain ("homo" amino acids), and amino acids where the carboxylate functional group amino acid in the side chain is substituted with a sulfonate group (such as cysteic acid).

Naturally-occurring amino acid residues may be e.g. classified into the following groups based on common side chain properties:
(1) Hydrophobic: Met, Ala, Val, Leu, and Ile;
(2) Neutral hydrophilic: Cys, Ser, and Thr;
(3) Acidic: Asp and Glu;
(4) Basic: Asn, Gln, His, Lys, and Arg;
(5) Residues that influence chain orientation: Gly and Pro; and
(6) Aromatic: Trp, Tyr, and Phe.

A nonconservative substitution of the amino acid sequence configuring an antibody or an antigen binding fragment thereof may be performed by exchanging an amino acid that belongs to one of these groups with an amino acid that belongs to another group. A more conservative substitution may be performed by exchanging an amino acid that belongs to one of these groups with another amino acid that belongs to the same group. Similarly, deletion or substitution of the amino acid sequence may be appropriately performed.

A modification of the amino acid configuring an antibody or an antigen binding fragment thereof may be e.g. a post-translational modification such as glycosylation by a sugar, acetylation, or phosphorylation. The antibody may be glycosylated at a conserved position in its constant region. Glycosylation of an antibody is ordinarily either N-linked or O-linked. N-linked means linking of a sugar moiety to the side chain of an asparagine residue. Tripeptide sequences asparagine-X-serine, asparagine-X-threonine, and asparagine-X-cysteine (wherein X is any amino acid other than proline) are recognition sequences for enzymatically adding a sugar moiety to the asparagine side chain. A potential glycosylation site is present when one of these tripeptide sequences is present in an antibody or an antigen binding fragment thereof. O-linked glycosylation may be the linking of either N-acetylgalactosamine, galactose, or xylose to a hydroxy amino acid (such as serine or threonine), and in some instances may be the linking to 5-hydroxy proline or 5-hydroxy lysine. The glycosylation condition (e.g. when glycosylation is performed with a biological means, the type of host cell or cell medium, pH, and the like) can be appropriately selected by those skilled in the art according to the purpose.

The anti-Notch4 antibody of the present invention or an antigen binding fragment thereof may be further modified based on technical common sense well-known to those skilled in the art by other modification methods alone or in combination.

The anti-Notch4 antibody of the present invention or an antigen binding fragment thereof may be produced by a method well-known to those skilled in the art. For example, the antibody may be produced with a hybridoma that produces the anti-Notch4 antibody of the present invention or an antigen binding fragment thereof, or by integrating the gene encoding the anti-Notch4 antibody of the present invention or an antigen binding fragment thereof into an expression vector and introducing said expression vector into e.g. E. coli cells, monkey COS cells, Chinese hamster ovary (CHO) cells, and the like.

The anti-Notch4 antibody of the present invention or an antigen binding fragment thereof may be those that are isolated or purified according to methods well-known to those skilled in the art. Here, "isolated" or "purified" means that it is artificially isolated or purified from the natural state. When a molecule or a composition is naturally occurring, it is "isolated" or "purified" when it has changed or is removed from its original environment or both. Examples of an isolation or purification method include, but are not limited to, electrophoresis, molecular biological, immunological, or chromatographic means, specifically, ion exchange chromatography, hydrophobic chromatography, or reverse phase HPLC chromatography, or isoelectric focusing.

The method employed for measuring the binding property (such as binding affinity and cross-reactivity) of an antibody or an antigen binding fragment thereof to an antigen may be a method well-known in the field to those skilled in the art. For example, binding affinity may be measured with, but is not limited to, Biacore™ biosensor, KinExA biosensor, scintillation proximity assay, ELISA, ORIGEN immunoassay (from IGEN), flow cytometry, fluorescence quenching, fluorescence transfer, yeast display, and/or immunostaining. The neutralizing activity of an antibody or an antigen binding fragment thereof against the binding of Notch4 to its ligand may be measured with, but is not limited to, Biacore™ biosensor, ELISA, and/or flow cytometry. The neutralizing activity an antibody or an antigen binding fragment thereof against signal transduction that is induced inside the human body due to the binding of Notch4 to its ligand, or against molecular expression response or functionality change of the cell may be measured with, but are not limited to, for example the following methods: (i) a reporter assay which detects variation in the expression of a molecule downstream of the Notch signal, (ii) Western Blot which detects Notch4 cleaving by TNF-α converting enzyme (TACE) or γ selectase, (iii) immune cell staining which detects nuclear import of Notch intracellular domain (NIC), and (iv) cell functionality evaluation which employs a normal cell such as a vascular endothelial cell or a cancer cell that expresses Notch4.

In one aspect, the present invention may be a pharmaceutical composition comprising the anti-Notch4 antibody of the present invention or an antigen binding fragment thereof.

The pharmaceutical composition comprising the anti-Notch4 antibody of the present invention or an antigen binding fragment thereof in an aqueous or dry preparation form may further comprise a pharmaceutically acceptable carrier, excipient, and/or a stabilizer. Examples of an acceptable carrier, excipient, or a stabilizer include saline; a buffer such as phosphoric acid, citric acid, and other organic acids; an antioxidant including ascorbic acid; a low molecular weight polypeptide; a protein (such as serum albumin, gelatin, or immunoglobulin); a hydrophilic polymer such as polyvinyl pyrrolidone; an amino acid; monosaccharides, disaccharides, and other carbohydrates including glucose, mannose, or dextrins; a chelator such as EDTA; sugar alcohols such as mannitol or sorbitol; a counter ion that forms a salt such as sodium; or a nonionic surfactant such as TWEEN™, PLURONICS™, or PEG.

The pharmaceutical composition comprising the anti-Notch4 antibody of the present invention or an antigen binding fragment thereof may be encapsulated e.g. in a microcapsule, in a colloidal drug delivery system (such as a liposome, an albumin microsphere, a microemulsion, a nanoparticle, or a nanocapsule), or in a macroemulsion. When sustained release administration of the antibody is desired in a preparation having release property suitable for any disease that requires administration of the antibody, microcapsulation of the antibody may be intended. Examples of a sustained release matrix include a polyester, a hydrogel (such as poly(2-hydroxyethyl-methacrylate) or poly(vinyl alcohol)), polylactic acids, a copolymer of L-glutamic acid and γ ethyl-L-glutamate, a nondegradable ethylene-vinyl acetate, a degradable lactic acid-glycolic acid copolymer such as LUPRON DEPOT™ (an injectable microsphere composed of lactic acid-glycolic acid copolymer and leuprolide acetate), and poly-D-(-)-3-hydroxy butyric acid.

A preparation employed for in vivo administration must be sterile. This can be easily achieved by filtration through a sterile filtration membrane.

The pharmaceutical composition comprising the anti-Notch4 antibody of the present invention or an antigen binding fragment thereof has the potential of being useful for treatment of non-small cell lung cancer, thyroid cancer, prostate cancer or hepatocellular carcinoma. In other words, another aspect of the present invention may be a method for treating non-small cell lung cancer, thyroid cancer, prostate cancer or hepatocellular carcinoma comprising a step of administering to a subject a therapeutically effective amount the anti-Notch4 antibody of the present invention or an antigen binding fragment thereof. Moreover, another aspect of the present invention may be a use of the anti-Notch4 antibody of the present invention or an antigen binding fragment thereof for manufacturing a therapeutic drug for non-small cell lung cancer, thyroid cancer, prostate cancer or hepatocellular carcinoma.

The anti-Notch4 antibody of the present invention or an antigen binding fragment thereof used for treatment of non-small cell lung cancer, thyroid cancer, prostate cancer or hepatocellular carcinoma is preferably an antibody that recognizes the extracellular domain of Notch4. For example, the anti-Notch4 antibody of the present invention or an antigen binding fragment thereof may be an antibody or an antigen binding fragment thereof that binds specifically to any site of positions 24-1447 in the amino acid sequence of human Notch4 shown in SEQ ID NO. 1. In the amino acid sequence of human Notch4 shown in SEQ ID NO. 1, positions 1-23 is the signal sequence, and positions 1448-2003 is the transmembrane domain and the intracellular domain.

The anti-Notch4 antibody of the present invention or an antigen binding fragment thereof can be used in a therapeutic method alone or in combination with other agents or compositions. For example, the anti-Notch4 antibody of the present invention or an antigen binding fragment thereof may be administered at the same or different times with another anticancer agent. Such a combination therapy comprises combined administration (two or more agents are contained in the same or separate preparation) and separate administration (e.g. at the same time or continuously). When two or more agents are administered separately, the administration of the anti-Notch4 antibody of the present invention or an antigen binding fragment thereof may be before or after the accompanying therapeutic method. The anticancer agent that may be used in combination with the anti-Notch4 antibody of the present invention or an antigen binding fragment thereof may be e.g. an anticancer agent that is effective for treating non-small cell lung cancer, thyroid cancer, prostate cancer or hepatocellular carcinoma. Examples of such an anticancer agent can include, but are not limited to, cisplatin, lenvatinib, and paclitaxel. Examples of the pharmaceutical composition for such a combination therapy can include, but are not limited to, a pharmaceutical composition comprising the anti-Notch4 antibody of the present invention or an antigen binding fragment thereof and cisplatin, a pharmaceutical composition comprising the anti-Notch4 antibody of the present invention or an antigen binding fragment thereof and lenvatinib, and a pharmaceutical composition comprising the anti-Notch4 antibody of the present invention or an antigen binding fragment thereof and paclitaxel.

The subject for administering the pharmaceutical composition comprising the anti-Notch4 antibody of the present invention or an antigen binding fragment thereof is not limited, and the present invention can be employed for a mammal (such as a human, a pig, a cow, a monkey, a baboon, a dog, a cat, a rat, and a mouse). However, humans can be excluded from the subject when it is not preferred.

The administration method of the pharmaceutical composition comprising the anti-Notch4 antibody of the present invention or an antigen binding fragment thereof to a subject (such as administration route, dosage, frequency of administration per day, and administration timing) is not limited, and can be appropriately determined by those skilled in the art (such as a physician) according to the health state of the subject, the extent of disease, the type of agent used in combination, and the like.

It is recognized by those skilled in the art that as long as it is not technically contradicting, any one of more of any and all aspects described herein may be appropriately combined to carry out the present invention. Further, it is recognized by those skilled in the art that as long as it is not technically contradicting, it is preferred that any and all preferred or advantageous aspects described herein is appropriately combined to carry out the present invention.

All disclosures of the literatures cited herein should be deemed to be clearly cited herein by reference, and those skilled in the art will be able to cite and recognize the content of the disclosure related to these literatures as a part of the present specification according to the context herein without departing from the spirit and scope of the present invention.

The literatures cited herein are provided solely for the purpose of disclosing the related technology preceding the filing date of the present application, and is not to be construed as an admission that the present inventors do not hold the priority right to said disclosures for reasons of prior invention or any other reason. All description of these literatures are based on the information available to the present applicants, and do not configure the acknowledgement that these descriptions are correct.

The terms used herein are employed for describing particular embodiments and do not intend to limit the invention.

The term "comprise" as used herein, unless the content clearly indicates to be understood otherwise, intends the presence the described items (such as components, steps, elements, or numbers), and does not exclude the presence of other items (such as components, steps, elements, or numbers). The term "consist of" encompasses the aspects described with terms "consist of" and/or "consist essentially of."

The term "neutralizing activity" as used herein means the activity to inhibit the binding of Notch4 to its ligand and/or the activity to inhibit signal transduction that is induced inside the human body by the binding of Notch4 to its ligand, or molecular expression response or functionality change of the cell.

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second are employed to express various elements, and it is recognized that these elements shall not be limited by these terms themselves. These terms are employed solely for the purpose of discriminating one element from another, and it is for example possible to describe a first element as a second element, and similarly to describe a second element as a first element without departing from the scope of the present invention.

The numeric values employed herein for indicating component content or numeric value range and the like, unless explicitly indicated, are to be understood as being modified by the term "about." For example, unless explicitly indicated, "4° C." is recognized as meaning "about 4° C.," and those skilled in the art can naturally reasonably recognize the extent thereof according to technical common sense and the context of the present specification.

Unless clearly indicated to mean otherwise in context, when used in the specification and claims herein, it should be recognized that each aspect represented in singular form may also be a plural form as long as it is not technically contradicting, and vice versa.

The present invention will now be described in further detail with reference to Examples. However, the present invention can be embodied by various aspects, and shall not be construed as being limited to the Examples described herein. Those skilled in the art of related technical field will be able to carry out the present invention with various modifications, additions, deletions, substitution, and the like without altering the spirit or scope of the present invention.

EXAMPLES

Example 1: Production of Anti-Human Notch4 Monoclonal Antibody

Production of Mouse Anti-Human Notch4 Monoclonal Antibody

In order to produce a monoclonal antibody against human Notch4 (Genbank Accession No. NP_004548.3) (SEQ ID NO. 1), Balb/c mice was immunized with three EGF repeats and the negative regulatory region (NRR) of human Notch4 (positions 1046-1445 of SEQ ID NO. 1) fused with secretory alkaline phosphatase (SEAP) and a histidine tag (hereinafter referred to as "human Notch4 3EGF-NRR-SEAP-His").

Human Notch4 3EGF-NRR-SEAP-His protein was prepared by the following steps: First, an expression vector pcDNA3.1-human Notch4 3EGF-NRR-SEAP-His was constructed. The three EGF repeats and NRR of human Notch4 were amplified by PCR, and subcloned to the SfiI/NotI site of pcDNA3.1 (Invitrogen/LifeTechnologies) having a DNA sequence encoding an Igκ signal sequence, SEAP, and a histidine tag. Next, expression vector pcDNA3.1-human Notch4 3EGF-NRR-SEAP-His was transfected into HEK293 EBNA cells (Invitrogen/LifeTechnologies) by Trans IT-LT1 (TAKARA). After 6 days of incubation (5% CO2, 37° C.), the culture supernatant was collected. The human Notch4 3EGF-NRR-SEAP-His protein was purified with a Protino column (MACHEREY-NAGEL).

Twenty micrograms of said human Notch4 3EGF-NRR-SEAP-His protein was mixed with the same amount of GERBU adjuvant (GERBU Biotechnik GmbH) and subcutaneously injected into Balb/c mice footpad. Three additional injections were administered on Days 3, 7, and 10. Mice were sacrificed on the next day, and peripheral lymph nodes were collected. Half of each peripheral lymph nodes were transplanted into SCID mice. Lymph node cells were prepared from the remaining half of each lymph node, and fused to P3U1 myeloma cells at a proportion of 5:1 in the presence of GenomeONE-CF (Ishihara Sangyo Kaisha, Ltd.). Said fused cells were cultured in a 96-well plastic plate. After 7 days of incubation (5% CO2, 37° C.), the culture supernatant was collected.

Ten micrograms of human Notch4 3EGF-NRR-SEAP-His protein were intravenously administered to said lymph node transplantation SCID mice on the day of transplantation and 6 days after transplantation. Three days after the final immunization, peripheral lymph node cells were collected, fused as described above, and cultured.

Mouse monoclonal antibodies of 8 clones were obtained by the above steps. From these, the most preferred lead antibody (6-3-A6) was selected based on Notch4-specific signal inhibitory activity and binding activity to mouse Notch4 and human Notch4.

Sequence Analysis of Mouse Anti-Human Notch4 Monoclonal Antibody (6-3-A6)

The DNA sequence encoding the heavy and light chains of clone 6-3-A6 was amplified by 5'-RACE (5'-rapid amplification of cDNA ends). Whole RNA was prepared from said hybridoma with TRIZOL (Invitrogen/LifeTechnologies) and treated using DNase (QIAGEN, RNase free DNase set). Double-stranded cDNA was prepared from said whole RNA using cDNA synthesizing kit (TAKARA). The 5' adaptor obtained by annealing of ad29S (ACATCACTCCGT (SEQ ID NO. 2)) and ad29AS (ACGGAGTGATGTCCGTC-GACGTATCTCTGCGTTGATACTTCAGCGTAGCT (SEQ ID NO. 3)) was added to said cDNA. The cDNA obtained was amplified by 5' forward primer (5'-PCR4 primer, AGCTACGCTGAAGTATCAACGCAGAG (SEQ ID NO. 4)) and 3' reverse primer (GCCAGTGGATAGACT-GATGG (SEQ ID NO. 5) was used for amplifying mouse IgG1 heavy chain and GATGGATACAGTTGGTGCAGC (SEQ ID NO. 6) was used for amplifying mouse Igκ light chain). Said amplified cDNA was inserted into pCR2.1 vector (Invitrogen/LifeTechnologies). The gene sequence was analyzed with ABI3130XL. The amino acid sequence encoded by the gene sequence identified by this analysis is shown in the following table.

Preparation of Chimeric Anti-Human Notch4 Antibody and Humanized Anti-Human Notch4 Antibody With overlapping extension PCR, the gene sequence of the heavy chain variable region of 6-3-A6 was bound to the gene sequence of the constant region of human IgG2 having mutations V234A and G237A as the heavy chain, and the gene sequence of the light chain variable region of 6-3-A6 was bound to the gene sequence of the constant region of human Igκ as the light chain to prepare a DNA sequence encoding a chimeric antibody. As used herein, "V234A" represents a mutation in which valine at position 234 is substituted with alanine and "G237A" represents a mutation in which glycine at position 237 is substituted with alanine. The sequence obtained as a result was inserted into expression vectors (pEE6.4 for heavy chain and pEE12.4 for light chain, Lonza). The amino acid and nucleotide sequences of the chimeric antibody are shown in the following tables.

TABLE 1

Amino Acid Sequence of Mouse Anti-human Notch4 Antibody (6-3-A6)

| Name | Sequence |
| --- | --- |
| Heavy chain variable region (SEQ ID NO. 7) | EVQLVESGGGLVQPGGSLKLSCAASGFTFSSYGMSWVRQTPDKRLE LVATINSNGGRTYYPDSVKGRFTISRDNAKNTLYLQMSSLKSEDTA MYYCARDQGFAYWGQGTLVTVSA |
| Light chain variable region (SEQ ID NO. 8) | DIVMTQSHKFMSTSVGDRVSITCKASQDVGTAVAWYQQKPGQSPKL LIYWASTRHTGVPDRFTGSGSGTDFTLTISNVQSEDLADYFCQQYS SYPWTFGGGTKLEIK |

TABLE 2

Nucleic Acid Sequence of Mouse Anti-human Notch4 Antibody (6-3-A6)

| Name | Sequence |
| --- | --- |
| Heavy chain variable region (SEQ ID NO. 9) | GAGGTGCAGCTGGTGGAGTCTGGGGGAGGCTTAGTGCAGCCTGGAG GGTCCCTGAAACTCTCCTGTGCAGCCTCTGGATTCACTTTCAGTAG CTATGGCATGTCTTGGGTTCGCCAGACTCCAGACAAGAGGCTGGAG TTGGTCGCAACCATTAATAGTAATGGTGGTAGAACCTATTATCCAG ACAGTGTGAAGGGCCGATTCACCATCTCCAGAGACAATGCCAAGAA CACCCTGTACCTGCAAATGAGCAGTCTGAAGTCTGAGGACACAGCC ATGTATTACTGTGCAAGAGACCAGGGTTTTGCTTACTGGGGCCAAG GGACTCTGGTCACTGTCTCTGCA |
| Light chain variable region (SEQ ID NO. 10) | GACATTGTGATGACCCAGTCTCACAAATTCATGTCCACATCAGTAG GAGACAGGGTCAGCATCACCTGCAAGGCCAGTCAGGATGTGGGTAC TGCTGTAGCCTGGTATCAACAGAAACCAGGGCAATCTCCTAAACTA CTGATTTACTGGGCATCCACCCGGCACACTGGAGTCCCTGATCGCT TCACAGGCAGTGGATCTGGGACAGATTTCACTCTCACCATTAGCAA TGTGCAGTCTGAAGACTTGGCAGATTATTTCTGTCAGCAATATAGC AGCTATCCGTGGACGTTCGGTGGAGGCACCAAGCTGGAAATCAAA |

TABLE 3

Amino Acid Sequence of Chimeric Anti-human Notch4 Antibody

| Name | Sequence (The variable region is indicated in bold, and CDRs determined with Kabat definition method in the variable region are underlined.) |
|---|---|
| Heavy chain (SEQ ID NO. 11) | EVQLVESGGGLVQPGGSLKLSCAASGFTFS<u>SYGMS</u>WVRQTPDKRLE LVAT<u>INSNGGRTYYPDSVKG</u>RFTISRDNAKNTLYLQMSSLKSEDTA MYYCARD<u>QGFAY</u>WGQGTLVTVSAASTKGPSVFPLAPCSRSTSESTA ALGCLVKDYFPEPVTVSWNSGALTSGVHTFPAVLQSSGLYSLSSVV TVPSSNFGTQTYTCNVDHKPSNTKVDKTVERKCCVECPPCPAPPAA APSVFLFPPKPKDTLMISRTPEVTCVVVDVSHEDPEVQFNWYVDGV EVHNAKTKPREEQFNSTFRVVSVLTVVHQDWLNGKEYKCKVSNKGL PAPIEKTISKTKGQPREPQVYTLPPSREEMTKNQVSLTCLVKGFYP SDIAVEWESNGQPENNYKTTPPMLDSDGSFFLYSKLTVDKSRWQQG NVFSCSVMHEALHNHYTQKSLSLSPGK |
| Light chain (SEQ ID NO. 12) | DIVMTQSHKFMSTSVGDRVSITC<u>KASQDVGTAVA</u>WYQQKPGQSPKL LIY<u>WASTRHT</u>GVPDRFTGSGSGTDFTLTISNVQSEDLADYFC<u>QQYS SYPWT</u>FGGGTKLEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |

TABLE 4

Nucleic Acid Sequence of Chimeric Anti-human Notch4 Antibody

| Name | Sequence (The variable region is indicated in bold.) |
|---|---|
| Heavy chain (SEQ ID NO. 13) | GAGGTGCAGCTGGTGGAGTCTGGGGGAGGCTTAGTGCAGCCTGGAG GGTCCCTGAAACTCTCCTGTGCAGCCTCTGGATTCACTTTCAGTAG CTATGGCATGTCTTGGGTTCGCCAGACTCCAGACAAGAGGCTGGAG TTGGTCGCAACCATTAATAGTAATGGTGGTAGAACCTATTATCCAG ACAGTGTGAAGGGCCGATTCACCATCTCCAGAGACAATGCCAAGAA CACCCTGTACCTGCAAATGAGCAGTCTGAAGTCTGAGGACACAGCC ATGTATTACTGTGCAAGAGACCAGGGTTTTGCTTACTGGGGCCAAG GGACTCTGGTCACTGTCTCTGCAGCTAGCACAAAAGGCCCCTCTGT CTTCCCTCTGGCTCCCTGCTCCCGCTCCACCTCCGAGTCCACTGCC GCTCTGGGCTGTCTGGTCAAGGATTACTTCCCTGAGCCAGTCACTG TGAGTTGGAACTCAGGCGCCCTGACCAGCGGAGTCCACACATTTCC CGCTGTGCTGCAGAGCTCCGGCCTGTACTCCCTGTCTAGTGTGGTC ACCGTGCCTTCAAGCAATTTCGGGACTCAGACCTATACATGCAACG TGGACCATAAGCCATCTAATACTAAGGTCGATAAAACCGTGGAGCG AAAATGCTGCGTGGAATGCCCACCTTGTCCTGCTCCACCAGCCGCT GCACCAAGCGTGTTCCTGTTTCCTCCAAAGCCCAAAGACACACTGA TGATCAGCAGAACTCCTGAGGTCACCTGCGTGGTCGTGGACGTGTC CCACGAGGATCCCGAAGTCCAGTTTAACTGGTACGTGGATGGGGTC GAAGTGCATAATGCAAAGACTAAACCTCGGGAGGAACAGTTCAACT CTACCTTTAGAGTCGTGAGTGTGCTGACAGTCGTGCACCAGGACTG GCTGAACGGAAAGGAGTATAAGTGCAAAGTGTCTAATAAGGGCCTG CCCGCCCCTATCGAGAAAACAATTAGTAAGACTAAAGGCCAGCCAA GGGAACCCCAGGTGTACACACTGCCCCCTAGTCGCGAGGAAATGAC AAAGAACCAGGTCTCACTGACTTGTCTGGTGAAAGGGTTCTATCCA TCCGACATTGCCGTGGAGTGGGAATCTAATGGACAGCCCGAAAACA ATTACAAGACCACACCACCCATGCTGGACAGCGATGGATCCTTCTT TCTGTATTCAAAGCTGACCGTGGATAAAAGCCGGTGGCAGCAGGGC AATGTCTTTTCCTGCTCTGTGATGCACGAAGCCCTGCACAACCACT ACACTCAGAAGTCCCTGTCCCTGTCTCCTGGCAAATGA |
| Light chain (SEQ ID NO. 14) | GACATTGTGATGACCCAGTCTCACAAATTCATGTCCACATCAGTAG GAGACAGGGTCAGCATCACCTGCAAGGCCAGTCAGGATGTGGGTAC TGCTGTAGCCTGGTATCAACAGAAACCAGGGCAATCTCCTAAACTA CTGATTTACTGGGCATCCACCCGGCACACTGGAGTCCCTGATCGCT TCACAGGCAGTGGATCTGGGACAGATTTCACTCTCACCATTAGCAA TGTGCAGTCTGAAGACTTGGCAGATTATTTCTGTCAGCAATATAGC AGCTATCCGTGGACGTTCGGTGGAGGCACCAAGCTGGAAATCAAAC GTACGGTCGCCGCCCCCTCCGTGTTTATTTTTCCTCCATCTGACGA ACAGCTGAAGAGTGGGACCGCCTCCGTGGTGTGCCTGCTGAACAAT TTCTACCCCCGGGAGGCCAAGGTGCAGTGGAAAGTCGACAACGCTC TGCAGTCTGGCAATAGTCAGGAGTCAGTGACTGAACAGGACAGCAA GGATTCCACCTATTCTCTGAGCTCCACCCTGACACTGAGCAAGCA GATTACGAAAAGCACAAAGTCTATGCCTGCGAAGTGACCCACCAGG GGCTGAGCAGTCCAGTGACCAAGTCCTTTAACAGGGGAGAGTGTTG A |

The antibody was humanized by transplanting mouse antibody 6-3-A6 CDR into the variable region of a human antibody. The amino acid sequence of mouse antibody 6-3-A6 was numbered according to the Kabat numbering system using Abysis software (licensed from UCL), and based on this numbering, said CDR was determined according to the Kabat definition or AbM definition method for identifying CDR. The amino acid and nucleotide sequences of 6-3-A6 CDR are shown in the following tables.

TABLE 5

Amino Acid Sequence of 6-3-A6 CDR

| Name | Sequence |
|---|---|
| Heavy chain CDR 1 (Kabat definition) (SEQ ID NO. 15) | SYGMS |
| Heavy chain CDR 1 (AbM definition) (SEQ ID NO. 16) | GFTFSSYGMS |
| Heavy chain CDR 2 (Kabat definition) (SEQ ID NO. 17) | TINSNGGRTYYPDSVKG |
| Heavy chain CDR 2 (AbM definition) (SEQ ID NO. 18) | TINSNGGRTY |
| Heavy chain CDR 3 (SEQ ID NO. 19) | DQGFAY |
| Light chain CDR 1 (SEQ ID NO. 20) | KASQDVGTAVA |
| Light chain CDR 2 (SEQ ID NO. 21) | WASTRHT |
| Light chain CDR 3 (SEQ ID NO. 22) | QQYSSYPWT |

TABLE 6

Nucleic Acid Sequence of 6-3-A6 CDR

| Name | Sequence |
|---|---|
| Heavy chain CDR 1 (Kabat definition) (SEQ ID NO. 23) | AGCTATGGCATGTCT |
| Heavy chain CDR 1 (AbM definition) (SEQ ID NO. 24) | GGATTCACTTTCAGTAGCTATGGCATGTCT |
| Heavy chain CDR 2 (Kabat definition) (SEQ ID NO. 25) | ACCATTAATAGTAATGGTGGTAGAACCTAT TATCCAGACAGTGTGAAGGGC |
| Heavy chain CDR 2 (AbM definition) (SEQ ID NO. 26) | ACCATTAATAGTAATGGTGGTAGAACCTAT |
| Heavy chain CDR 3 (SEQ ID NO. 27) | GACCAGGGTTTTGCTTAC |
| Light chain CDR 1 (SEQ ID NO. 28) | AAGGCCAGTCAGGATGTGGGTACTGCTGTAGCC |
| Light chain CDR 2 (SEQ ID NO. 29) | TGGGCATCCACCCGGCACACT |
| Light chain CDR 3 (SEQ ID NO. 30) | CAGCAATATAGCAGCTATCCGTGGACG |

Based on the high homology to the framework region (FR) of 6-3-A6, FR of a human antibody, IGKV1-27*1 or IGKV3-15*1 and JK1 for the light chain, and IGHV3-64*01 and JH4 for the heavy chain were selected as the FR of the humanized antibody. Then, a 3D structure prediction model of mouse 6-3-A6 was employed to predict the amino acid in the FR that interacts with the amino acid of CDR, and transplanted together with CDR. The constant region of human IgG2 with mutations V234A and G237A and with or without a C-terminal lysine residue, as well as human Igκ were each employed as the constant region of heavy and light chains. HK1, HK2, and HK3 were designed as the heavy chain of the humanized antibody to which CDR determined by the Kabat definition method was transplanted, HA1 and HA2 were designed as the heavy chain of the humanized antibody to which CDR determined by the AbM definition method was transplanted, L1, L2, and L5 were designed as the light chain of the humanized antibody that employs IGKV1-27*1 and JK1, and L3, L4, and L6 were designed as the light chain of the humanized antibody that employs IGKV3-15*1 and JK1. The following tables show the amino acid and nucleotide sequences of the variable region of the humanized antibody, the constant region of human IgG2 with mutations V234A and G237A and with or without a C-terminal lysine residue, as well as human Igκ.

TABLE 7

Amino Acid and Nucleic Acid Sequences of the Variable
Region of Humanized Anti-human Notch4 Antibody
Heavy Chain (HK1)

| Name | Sequence (CDRs determined with the Kabat definition method are underlined.) |
|---|---|
| Amino acid sequence (SEQ ID NO. 31) | EVQLVESGGGLVQPGGSLRLSCAASGFTFS<u>SYGMS</u>WVRQAPGKGLE YVS<u>TINSNGGRTYYPDSVKG</u>RFTISRDNSKNTLYLQMGSLRAEDMA VYYCAR<u>DQGFAY</u>WGQGTLVTVSS |
| Nucleic acid sequence (SEQ ID NO. 32) | GAGGTGCAGCTGGTCGAGAGCGGAGGGGGGCTGGTGCAGCCAGGAG GGTCTCTGAGGCTGAGTTGCGCCGCTTCAGGCTTCACCTTCAGCTC <u>CTACGGGATGTCTT</u>GGGTGCGCCAGGCTCCAGGGAAGGGACTGGAG TATGTCAGC<u>ACCATCAACTCCAATGGAGGCCGAACATACTATCCTG ACTCCGTGAAGGGC</u>CGGTTCACTATCTCTAGAGATAACAGTAAGAA CACCCTGTACCTGCAGATGGGCAGCCTGAGAGCAGAAGACATGGCC GTCTACTATTGTGCAAGG<u>GATCAGGGATTCGCATAC</u>TGGGGACAGG GAACTCTGGTGACCGTCTCAAGC |

TABLE 8

Amino Acid and Nucleic Acid Sequences of the
Variable Region of Humanized Anti-human Notch4
Antibody Heavy Chain (HK2)

| Name | Sequence (CDRs determined with the Kabat definition method are underlined.) |
|---|---|
| Amino acid sequence (SEQ ID NO. 33) | EVQLVESGGGLVQPGGSLRLSCAASGFTFS<u>SYGMS</u>WVRQAPGKGLE LVS<u>TINSNGGRTYYPDSVKG</u>RFTISRDNSKNTLYLQMGSLRAEDMA VYYCAR<u>DQGFAY</u>WGQGTLVTVSS |
| Nucleic acid sequence (SEQ ID NO. 34) | GAAGTGCAGCTGGTCGAGAGCGGGGGAGGGCTGGTGCAGCCAGGAG GGTCTCTGAGGCTGAGTTGCGCCGCTTCAGGCTTCACCTTCAGCTC <u>CTACGGGATGTCTT</u>GGGTGCGCCAGGCTCCAGGGAAGGGACTGGAG CTGGTCAGC<u>ACCATCAACTCCAATGGAGGCCGAACATACTATCCTG ACTCCGTGAAGGGC</u>CGGTTCACTATCTCTAGAGATAACAGTAAGAA CACCCTGTATCTGCAGATGGGCAGCCTGAGAGCAGAAGACATGGCC GTCTACTATTGTGCCCGA<u>GATCAGGGGTTCGCTTAT</u>GGGGACAGG GGACACTGGTGACCGTGAGCAGC |

TABLE 9

Amino Acid and Nucleic Acid Sequences of the
Variable Region of Humanized Anti-human Notch4
Antibody Heavy Chain (HK3)

| Name | Sequence (CDRs determined with the Kabat definition method are underlined.) |
|---|---|
| Amino acid sequence (SEQ ID NO. 35) | EVQLVESGGGLVQPGGSLRLSCAASGFTFS<u>SYGMS</u>WVRQAPGKGLE LVA<u>TINSNGGRTYYPDSVKG</u>RFTISRDNSKNTLYLQMGSLKAEDMA VYYCAR<u>DQGFAY</u>WGQGTLVTVSS |
| Nucleic acid sequence (SEQ ID NO. 36) | GAAGTGCAGCTGGTCGAGAGTGGGGGAGGCCTGGTGCAGCCAGGAG GGTCTCTGAGGCTGAGTTGCGCCGCTTCAGGCTTCACCTTCAGC<u>TC CTACGGGATGTCCT</u>GGGTGCGCCAGGCTCCAGGGAAAGGACTGGAG CTGGTCGCC<u>ACCATCAACTCTAATGGAGGCCGAACATACTATCCTG ACAGTGTGAAGGGC</u>CGGTTCACTATTAGCAGAGATAACTCCAAAAA TACCCTGTATCTGCAGATGGGCAGCCTGAAGGCAGAAGACATGGCC GTCTACTATTGTGCTCGG<u>GATCAGGGGTTCGCCTAT</u>TGGGGGCAGG GGACTCTGGTCACTGTCTCTTCC |

TABLE 10

Amino Acid and Nucleic Acid Sequences of the Variable Region of Humanized Anti-human Notch4 Antibody Heavy Chain (HA1)

| Name | Sequence (CDRs determined with the AbM definition method are underlined.) |
|---|---|
| Amino acid sequence (SEQ ID NO. 37) | EVQLVESGGGLVQPGGSLRLSCAAS<u>GFTFSSYGMS</u>WVRQAPGKGLE YVS<u>TINSNGGRTYYANSVKG</u>RFTISRDNSKNTLYLQMGSLRAEDMA VYYCAR<u>DQGFAY</u>WGQGTLVTVSS |
| Nucleic acid sequence (SEQ ID NO. 38) | GAAGTGCAGCTGGTCGAATCTGGGGGGGGACTGGTGCAGCCAGGAG GGTCTCTGAGGCTGAGTTGCGCCGCTTC<u>AGGCTTCACCTTCAGCTC CTACGGGATGTC</u>TTGGGTGCGCCAGGCTCCTGGGAAGGGACTGGAG TATGTCAGC<u>ACCATCAACTCCAATGGAGGCCGAACATACTATGCCA ACTCCGTGAAGGG</u>CCGGTTCACTATCTCTAGAGACAACAGTAAGAA CACCCTGTACCTGCAGATGGGCAGCCTGAGAGCAGAAGATATGGCC GTCTACTATTGTGCTCGG<u>GATCAGGGCTTTGCTTAT</u>TGGGGACAGG GGACACTGGTCACCGTCTCCTCC |

TABLE 11

Amino Acid and Nucleic Acid Sequences of the Variable Region of Humanized Anti-human Notch4 Antibody Heavy Chain (HA2)

| Name | Sequence (CDRs determined with the AbM definition method are underlined.) |
|---|---|
| Amino acid sequence (SEQ ID NO. 39) | EVQLVESGGGLVQPGGSLRLSCAAS<u>GFTFSSYGMS</u>WVRQAPGKGLE LVS<u>TINSNGGRTYYANSVKG</u>RFTISRDNSKNTLYLQMGSLRAEDMA VYYCAR<u>DQGFAY</u>WGQGTLVTVSS |
| Nucleic acid sequence (SEQ ID NO. 40) | GAGGTGCAGCTGGTCGAATCCGGGGGGGGCTGGTGCAGCCAGGAG GGTCTCTGAGGCTGAGTTGCGCCGCTTC<u>AGGCTTCACCTTCAGCTC CTACGGGATGTC</u>TTGGGTGCGCCAGGCTCCTGGGAAGGGACTGGAG CTGGTCAGC<u>ACCATCAACTCCAATGGAGGCCGAACATACTATGCCA ACTCCGTGAAGGG</u>CCGGTTCACTATCTCTAGAGACAACAGTAAGAA CACCCTGTATCTGCAGATGGGCAGCCTGAGAGCAGAAGATATGGCC GTCTACTATTGTGCTCGG<u>GATCAGGGCTTCGCCTAC</u>TGGGGCAGG GAACACTGGTCACCGTCTCCTCA |

TABLE 12

Amino Acid and Nucleic Acid Sequences of the Variable Region of Humanized Anti-human Notch4 Antibody Light Chain (L1)

| Name | Sequence (CDRs determined with the Kabat definition method are underlined.) |
|---|---|
| Amino acid sequence (SEQ ID NO. 41) | DIQMTQSPSSLSASVGDRVTITC<u>KASQDVGTAVA</u>WYQQKPGKVPKL LIY<u>WASTRHT</u>GVPSRFSGSGSGTDFTLTISSLQPEDVATYYC<u>QQYS SYPWT</u>FGQGTKVEIK |
| Nucleic acid sequence (SEQ ID NO. 42) | GACATTCAGATGACACAGAGCCCTTCATCTCTGAGTGCATCAGTGG GAGACAGGGTCACCATCACATGC<u>AAAGCCAGCCAGGATGTGGGAAC CGCAGTCGCTTGG</u>TACCAGCAGAAGCCCGGGAAAGTGCCTAAGCTG CTGATCTACT<u>GGGCTAGTACACGGCACACT</u>GGCGTCCCATCCAGAT TCAGCGGCTCCGGGTCTGGAACCGACTTTACTCTGACCATCAGCTC CCTGCAGCCCGAGGATGTGGCCACATACTATTGC<u>CAGCAGTATTCA TCTTATCCTTGGACC</u>TTCGGACAGGGAACAAAAGTGGAAATCAAA |

TABLE 13

Amino Acid and Nucleic Acid Sequences of the Variable Region of Humanized Anti-human Notch4 Antibody Light Chain (L2)

| Name | Sequence (CDRs determined with the Kabat definition method are underlined.) |
|---|---|
| Amino acid sequence (SEQ ID NO. 43) | DIQMTQSPSSLSASVGDRVTITC<u>KASQDVGTAVA</u>WYQQKPGKVPKL LIY<u>WASTRHT</u>GVPSRFSGSGSGTDFTLTISSLQPEDVATYFC<u>QQYS SYPWT</u>FGQGTKVEIK |
| Nucleic acid sequence (SEQ ID NO. 44) | GATATTCAGATGACTCAGAGCCCCTCCTCTCTGAGTGCATCAGTGG GAGACAGGGTCACCATCACATGC<u>AAAGCCAGCCAGGATGTGGGAAC CGCAGTCGCTTGG</u>TACCAGCAGAAGCCCGGAAAGTGCCTAAGCTG CTGATCTAC<u>TGGGCTAGTACACGGCACACT</u>GGCGTCCCATCCAGAT TCAGCGGCTCCGGGTCTGGAACCGACTTTACTCTGACCATCAGCTC CCTGCAGCCCGAGGATGTGGCCACATACTTCTGC<u>CAGCAGTATTCA TCCTATCCTTGGACC</u>TTCGGACAGGGAACTAAAGTGGAGATTAAG |

TABLE 14

Amino Acid and Nucleic Acid Sequences of the Variable Region of Humanized Anti-human Notch4 Antibody Light Chain (L3)

| Name | Sequence (CDRs determined with the Kabat definition method are underlined.) |
|---|---|
| Amino acid sequence (SEQ ID NO. 45) | EIVMTQSPATLSVSPGERATLSC<u>KASQDVGTAVA</u>WYQQKPGQAPRL LIY<u>WASTRHT</u>GIPARFSGSGSGTEFTLTISSLQSEDFAVYYC<u>QQYS SYPWT</u>FGQGTKVEIK |
| Nucleic acid sequence (SEQ ID NO. 46) | GAAATTGTGATGACCCAGTCTCCCGCCACACTGTCTGTGAGTCCAG GAGAGAGGGCAACTCTGTCTTGC<u>AAGGCCAGTCAGGACGTGGGAAC CGCAGTCGCTT</u>GGTACCAGCAGAAACCCGGGCAGGCTCCTCGGCTG CTGATCTAT<u>TGGGCATCCACTCGGCACACC</u>GGCATTCCCGCCAGAT TCTCAGGCAGCGGGTCCGGAACAGAGTTTACCCTGACAATCAGCTC CCTGCAGAGCGAAGATTTCGCTGTCTACTATTGC<u>CAGCAGTATTCT AGTTATCCTTGGACA</u>TTCGGCCAGGGAACAAAAGTGGAAATCAAA |

TABLE 15

Amino Acid and Nucleic Acid Sequences of the Variable Region of Humanized Anti-human Notch4 Antibody Light Chain (L4)

| Name | Sequence (CDRs determined with the Kabat definition method are underlined.) |
|---|---|
| Amino acid sequence (SEQ ID NO. 47) | EIVMTQSPATLSVSPGERATLSC<u>KASQDVGTAVA</u>WYQQKPGQAPRL LIY<u>WASTRHT</u>GIPARFSGSGSGTEFTLTISSLQSEDFAVYFC<u>QQYS SYPWT</u>FGQGTKVEIK |
| Nucleic acid sequence (SEQ ID NO. 48) | GAAATCGTGATGACCCAGAGCCCCGCAACACTGTCTGTGAGTCCAG GAGAGAGGGCAACTCTGTCTTGC<u>AAGGCCAGTCAGGACGTGGGAAC CGCAGTCGCT</u>TGGTACCAGCAGAAACCCGGGCAGGCTCCTCGGCTG CTGATCTAT<u>TGGGCATCCACTCGGCACACC</u>GGCATTCCCGCCAGAT TCTCAGGCAGCGGGTCCGGAACAGAGTTTACCCTGACAATCAGCTC CCTGCAGAGCGAAGATTTCGCTGTCTACTTTTGC<u>CAGCAGTATTCA TCCTATCCTTGGACC</u>TTCGGACAGGGAACAAAAGTGGAAATCAAA |

TABLE 16

Amino Acid and Nucleic Acid Sequences of the Variable Region of Humanized Anti-human Notch4 Antibody Light Chain (L5)

| Name | Sequence (CDRs determined with the Kabat definition method are underlined.) |
| --- | --- |
| Amino acid sequence (SEQ ID NO. 49) | DIQMTQSPSSLSASVGDRVTITC<u>KASQDVGTAVA</u>WYQQKPGKSPKL LIY<u>WASTRHT</u>GVPSRFSGSGSGTDFTLTISSLQPEDVATYFC<u>QQYS SYPWT</u>FGQGTKVEIK |
| Nucleic acid sequence (SEQ ID NO. 50) | GATATCCAGATGACCCAGTCCCCAAGCTCCCTGTCCGCATCTGTGG GCGACCGGGTCACCATTACATGT<u>AAAGCCAGTCAGGATGTGGGAAC AGCCGTCGCT</u>TGGTACCAGCAGAAGCCCGGCAAATCTCCTAAGCTG CTGATCTATT<u>GGGCTTCCACACGGCACACT</u>GGCGTGCCCTCTAGAT TCAGTGGCTCAGGGAGCGGAACAGACTTTACTCTGACCATTTCTAG TCTGCAGCCAGAGGATGTGGCAACTTACTTCTGCCAG<u>CAGTACTCA AGCTATCCCTGGACC</u>TTTGGCCAGGGGACAAAAGTCGAAATCAAG |

TABLE 17

Amino Acid and Nucleic Acid Sequences of the Variable Region of Humanized Anti-human Notch4 Antibody Light Chain (L6)

| Name | Sequence (CDRs determined with the Kabat definition method are underlined.) |
| --- | --- |
| Amino acid sequence (SEQ ID NO. 51) | EIVMTQSPATLSVSPGERATLSC<u>KASQDVGTAVA</u>WYQQKPGQSPRL LIY<u>WASTRHT</u>GIPARFSGSGSGTEFTLTISSLQSEDFAVYFC<u>QQYS SYPWT</u>FGQGTKVEIK |
| Nucleic acid sequence (SEQ ID NO. 52) | GAAATCGTGATGACCCAGAGCCCCGCAACACTGTCTGTGAGTCCAG GAGAGAGGGCAACTCTGTCTTGC<u>AAGGCCAGTCAGGACGTGGGAAC CGCAGTCGCT</u>TGGTACCAGCAGAAACCCGGGCAGTCTCCTCGGCTG CTGATCTATT<u>GGGCATCCACTCGGCACACC</u>GGCATTCCCGCCAGAT TCTCAGGCAGCGGGTCCGGAACAGAGTTTACCCTGACAATCAGCTC CCTGCAGAGCGAAGATTTCGCTGTCTACTTTTGC<u>CAGCAGTATTCA TCCTATCCTTGGACC</u>TTCGGACAGGGAACAAAAGTGGAAATCAAA |

TABLE 18

Amino Acid and Nucleic Acid Sequences of the Constant Region of Human IgG2 with Mutations V234A and G237A and C-terminal Lysine

| Name | Sequence |
| --- | --- |
| Amino acid sequence (SEQ ID NO. 53) | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPAAAPSVFLFPPKPKDTLMISRTPEV TCVVVDVSHEDPEVQFNWYVDGVEVHNAKTKPREEQFNSTFRVVSV LTVVHQDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHNHYTQKSLSL SPGK |
| Nucleic acid sequence (SEQ ID NO. 54) | GCTAGCACAAAAGGCCCCTCTGTCTTCCCTCTGGCTCCCTGCTCCC GCTCCACCTCCGAGTCCACTGCCGCTCTGGGCTGTCTGGTCAAGGA TTACTTCCCTGAGCCAGTCACTGTGAGTTGGAACTCAGGCGCCCTG ACCAGCGGAGTCCACACATTTCCCGCTGTGCTGCAGAGCTCCGGCC TGTACTCCCTGTCTAGTGTGGTCACCGTGCCTTCAAGCAATTTCGG GACTCAGACCTATACATGCAACGTGGACCATAAGCCATCTAATACT AAGGTCGATAAAACCGTGGAGCGAAAATGCTGCGTGGAATGCCCAC CTTGTCCTGCTCCACCAGCCGCTGCACCAAGCGTGTTCCTGTTTCC TCCAAAGCCCAAAGACACACTGATGATCAGCAGAACTCCTGAGGTC ACCTGCGTGGTCGTGGACGTGTCCCACGAGGATCCCGAAGTCCAGT TTAACTGGTACGTGGATGGGGTCGAAGTGCATAATGCAAAGACTAA ACCTCGGGAGGAACAGTTCAACTCTACCTTTAGAGTCGTGAGTGTG CTGACAGTCGTGCACCAGGACTGGCTGAACGGAAAGGAGTATAAGT GCAAAGTGTCTAATAAGGGCCTGCCCGCCCCTATCGAGAAAACAAT TAGTAAGACTAAAGGCCAGCCAAGGGAACCCCAGGTGTACACACTG CCCCCTAGTCGCGAGGAAATGACAAAGAACCAGGTCTCACTGACTT GTCTGGTGAAAGGGTTCTATCCATCCGACATTGCCGTGGAGTGGGA |

TABLE 18-continued

Amino Acid and Nucleic Acid Sequences of the Constant Region of Human IgG2 with Mutations V234A and G237A and C-terminal Lysine

| Name | Sequence |
|---|---|
| | ATCTAATGGACAGCCCGAAAACAATTACAAGACCACACCACCCATG<br>CTGGACAGCGATGGATCCTTCTTTCTGTATTCAAAGCTGACCGTGG<br>ATAAAAGCCGGTGGCAGCAGGGCAATGTCTTTTCCTGCTCTGTGAT<br>GCACGAAGCCCTGCACAACCACTACACTCAGAAGTCCCTGTCCCTG<br>TCTCCTGGCAAATGA |

TABLE 19

Amino Acid and Nucleic Acid Sequences of the Constant Region of Human IgG2 With Mutations V234A and G237A and Without C-terminal Lysine

| Name | Sequence |
|---|---|
| Amino acid sequence (SEQ ID NO. 55) | ASTKGPSVFPLAPCSRSTSESTAALGCLVKDYFPEPVTVSWNSGAL<br>TSGVHTFPAVLQSSGLYSLSSVVTVPSSNFGTQTYTCNVDHKPSNT<br>KVDKTVERKCCVECPPCPAPPAAAPSVFLFPPKPKDTLMISRTPEV<br>TCVVVDVSHEDPEVQFNWYVDGVEVHNAKTKPREEQFNSTFRVVSV<br>LTVVHQDWLNGKEYKCKVSNKGLPAPIEKTISKTKGQPREPQVYTL<br>PPSREEMTKNQVSLTCLVKGFYPSDIAVEWESNGQPENNYKTTPPM<br>LDSDGSFFLYSKLTVDKSRWQQGNVFSCSVMHEALHNHYTQKSLSL<br>SPG |
| Nucleic acid sequence (SEQ ID NO. 56) | GCTAGCACAAAAGGCCCCTCTGTCTTCCCTCTGGCTCCCTGCTCCC<br>GCTCCACCTCCGAGTCCACTGCCGCTCTGGGCTGTCTGGTCAAGGA<br>TTACTTCCCTGAGCCAGTCACTGTGAGTTGGAACTCAGGCGCCCTG<br>ACCAGCGGAGTCCACACATTTCCCGCTGTGCTGCAGAGCTCCGGCC<br>TGTACTCCCTGTCTAGTGTGGTCACCGTGCCTTCAAGCAATTTCGG<br>GACTCAGACCTATACATGCAACGTGGACCATAAGCCATCTAATACT<br>AAGGTCGATAAAACCGTGGAGCGAAAATGCTGCGTGGAATGCCCAC<br>CTTGTCCTGCTCCACCAGCCGCTGCACCAAGCGTGTTCCTGTTTCC<br>TCCAAAGCCCAAAGACACACTGATGATCAGCAGAACTCCTGAGGTC<br>ACCTGCGTGGTCGTGGACGTGTCCCACGAGGATCCCGAAGTCCAGT<br>TTAACTGGTACGTGGATGGGGTCGAAGTGCATAATGCAAAGACTAA<br>ACCTCGGGAGGAACAGTTCAACTCTACCTTTAGAGTCGTGAGTGTG<br>CTGACAGTCGTGCACCAGGACTGGCTGAACGGAAAGGAGTATAAGT<br>GCAAAGTGTCTAATAAGGGCCTGCCCGCCCCTATCGAGAAAACAAT<br>TAGTAAGACTAAAGGCCAGCCAAGGGAACCCCAGGTGTACACACTG<br>CCCCCTAGTCGCGAGGAAATGACAAAGAACCAGGTCTCACTGACTT<br>GTCTGGTGAAAGGGTTCTATCCATCCGACATTGCCGTGGAGTGGGA<br>ATCTAATGGACAGCCCGAAAACAATTACAAGACCACACCACCCATG<br>CTGGACAGCGATGGATCCTTCTTTCTGTATTCAAAGCTGACCGTGG<br>ATAAAAGCCGGTGGCAGCAGGGCAATGTCTTTTCCTGCTCTGTGAT<br>GCACGAAGCCCTGCACAACCACTACACTCAGAAGTCCCTGTCCCTG<br>TCTCCTGGCTGA |

TABLE 20

Amino Acid and Nucleic Acid Sequences of the Constant Region of Human Igκ

| Name | Sequence |
|---|---|
| Amino acid sequence (SEQ ID NO. 57) | RTVAAPSVFIFPPSDEQLKSGTASVVCLLNNFYPREAKVQWKVDNA<br>LQSGNSQESVTEQDSKDSTYSLSSTLTLSKADYEKHKVYACEVTHQ<br>GLSSPVTKSFNRGEC |
| Nucleic acid sequence (SEQ ID NO. 58) | CGTACGGTCGCCGCCCCCTCCGTGTTTATTTTTCCTCCATCTGACG<br>AACAGCTGAAGAGTGGGACCGCCTCCGTGGTGTGCCTGCTGAACAA<br>TTTCTACCCCCGGGAGGCCAAGGTGCAGTGGAAAGTCGACAACGCT<br>CTGCAGTCTGGCAATAGTCAGGAGTCAGTGACTGAACAGGACAGCA<br>AGGATTCCACCTATTCTCTGAGCTCCACCCTGACACTGAGCAAAGC<br>AGATTACGAAAAGCACAAAGTCTATGCCTGCGAAGTGACCCACCAG<br>GGGCTGAGCAGTCCAGTGACCAAGTCCTTTAACAGGGGAGAGTGTT<br>GA |

The gene sequences of the variable region of these humanized antibodies were synthesized by GenScript USA Inc., and inserted into the constant region of human IgG2 with or without a C-terminal lysine or pcDNA3.3 (Invitrogen) comprising the DNA sequence encoding the constant region of human Igκ. Said expression vectors were transfected into FreeStyle 293-F cells (Invitrogen) using FreeStyle 293 expression system (Invitrogen) in order to produce the antibodies. The supernatant was collected and purified with Protein A (GE Healthcare).

The full length (variable region+constant region) gene sequences of the humanized antibodies were similarly optimized, fully synthesized by GenScript USA Inc., and the heavy chain was inserted into pEE6.4 and the light chain into pEE12.4 (Lonza). These expression vectors were employed as above in order to produce the antibodies. The optimized nucleotide sequences of the humanized antibodies are shown in the following tables.

TABLE 21

Optimized Nucleic Acid Sequence of Humanized Anti-human Notch4 Antibody Heavy Chain (HK2 Variable Region + Human IgG2 Constant Region with Mutations V234A and G237A and Without C-terminal Lysine)

| Name | Sequence |
| --- | --- |
| Nucleic acid sequence (SEQ ID NO. 59) | GAAGTGCAGCTGGTCGAATCTGGGGGGGGTCTGGTGCAGCCAGGCG GATCCCTGAGACTGAGCTGCGCCGCTTCTGGGTTCACATTTTCCAG CTACGGCATGTCCTGGGTCCGCCAGGCTCCAGGCAAGGGACTGGAG CTGGTGAGTACAATCAACTCAAATGGGGGTCGAACTTACTATCCCG ACTCCGTGAAGGGCAGGTTCACTATTTCCCGGGATAACAGCAAAAA TACCCTGTACCTGCAGATGGGGTCCCTGCGAGCTGAAGACATGGCA GTGTACTATTGTGCCCGTGATCAGGGTTTCGCTTATTGGGGGCAGG GTACTCTGGTCACCGTGTCTAGTGCTTCTACCAAGGGACCATCCGT GTTCCCACTGGCACCATGCTCCCGGAGCACATCTGAGAGTACTGCA GCCCTGGGCTGTCTGGTGAAGGACTATTTCCCTGAACCAGTCACAG TGAGCTGGAACTCTGGCGCACTGACAAGCGGAGTCCACACTTTTCC TGCCGTGCTGCAGTCATCCGGCCTGTACTCTCTGAGCTCTGTGGTC ACTGTCCCCAGTTCAAATTTCGGAACTCAGACCTATACATGCAACG TGGACCATAAGCCTAGCAATACCAAGGTCGATAAAACAGTGGAGCG TAAATGCTGCGTGGAATGCCCACCTTGTCCAGCACCACCAGCTGCA GCCCCTTCCGTGTTCCTGTTTCCTCAAAGCCAAAAGACACCCTGA TGATCTCTAGAACCCCCGAGGTCACATGCGTGGTCGTGGACGTGAG TCACGAGGATCCTGAAGTCCAGTTTAACTGGTACGTGGATGGCGTC GAAGTGCATAATGCCAAGACAAAACCAAGAGAGGAACAGTTCAACT CAACCTTTCGCGTCGTGTCCGTGCTGACAGTCGTGCACCAGGATTG GCTGAACGGCAAGGAGTATAAGTGCAAAGTGTCCAATAAGGGACTG CCCGCTCCTATCGAGAAAACTATTTCCAAGACCAAAGGACAGCCTA GGGAACCACAGGTGTACACTCTGCCCCCTTCCCGGGAGGAAATGAC TAAGAACCAGGTCAGCCTGACCTGTCTGGTGAAAGGGTTCTATCCT AGTGACATTGCCGTGGAGTGGGAATCAAATGGTCAGCCAGAGAACA ATTACAAGACCACACCCACCCATGCTGGACAGTGATGGCTCATTCTT TCTGTATAGCAAGCTGACCGTCGATAAATCTAGGTGGCAGCAGGGA AACGTGTTCTCCTGCTCCGTGATGCACGAAGCACTGCACAACCATT ACACCCAGAAATCCCTGAGCCTGTCCCCCGGCTGA |

TABLE 22

Optimized Nucleic Acid Sequence of Humanized Anti-human Notch4 Antibody Heavy Chain (HK3 Variable Region + Human IgG2 Constant Region with Mutations V234A and G237A and Without C-terminal Lysine)

| Name | Sequence |
| --- | --- |
| Nucleic acid sequence (SEQ ID NO. 60) | GAGGTGCAGCTGGTCGAGTCCGGGGGGGGTCTGGTGCAGCCAGGAG GATCCCTGAGGCTGAGCTGCGCCGCTTCTGGGTTCACATTTTCCAG CTACGGCATGTCCTGGGTCCGCCAGGCACCAGGCAAGGGACTGGAG CTGGTGGCCACAATCAACAGTAATGGGGGTAGAACTTACTATCCCG ACTCAGTGAAGGGCAGGTTCACTATTAGTCGGGATAACTCAAAAAA TACCCTGTACCTGCAGATGGGGTCCCTGAAGGCTGAAGACATGGCA GTGTACTATTGTGCCCGCGATCAGGGTTTCGCTTATTGGGGGCAGG GTACTCTGGTCACCGTGTCTAGTGCCTCCACCAAGGGCCCAGCGT GTTTCCACTGGCTCCCTGCTCCCGAAGCACATCTGAGAGTACTGCA GCCCTGGGCTGTCTGGTGAAGGACTATTTCCCTGAACCAGTCACAG TGAGCTGGAACTCTGGCGCTCTGACATCTGGAGTCCACACTTTTCC TGCAGTGCTGCAGTCATCCGGCCTGTACTCCCTGAGCTCTGTGGTC ACTGTCCCCAGTTCAAATTTCGGAACTCAGACCTATACATGCAACG TGGACCATAAACCTAGCAATACCAAGGTCGATAAAACAGTGGAGCG GAAGTGCTGTGTGGAATGCCCACCTTGTCCAGCTCCACCAGCTGCA GCCCCTTCTGTGTTCCTGTTTCCTCCAAAGCCAAAAGACACCCTGA |

TABLE 22-continued

Optimized Nucleic Acid Sequence of Humanized
Anti-human Notch4 Antibody Heavy Chain (HK3 Variable
Region + Human IgG2 Constant Region with
Mutations V234A and G237A and Without C-terminal Lysine)

| Name | Sequence |
|---|---|
|  | TGATCAGCAGGACCCCCGAGGTCACATGTGTGGTCGTGGACGTGTC<br>TCACGAGGATCCTGAAGTCCAGTTTAACTGGTACGTGGATGGCGTC<br>GAAGTGCATAATGCAAAGACAAAACCAAGAGAGGAACAGTTCAACT<br>CTACCTTTCGCGTCGTGAGTGTGCTGACAGTCGTGCACCAGGATTG<br>GCTGAACGGCAAGGAGTATAAGTGCAAAGTGTCCAATAAGGGACTG<br>CCCGCCCCTATCGAGAAAACTATTAGCAAGACCAAAGGACAGCCTC<br>GAGAACCACAGGTGTACACTCTGCCCCCTAGTCGTGAGGAAATGAC<br>TAAGAACCAGGTCTCCCTGACCTGTCTGGTGAAAGGGTTCTATCCT<br>AGCGACATTGCCGTGGAGTGGGAATCTAATGGTCAGCCAGAGAACA<br>ATTACAAGACCACACCCACCCATGCTGGACAGTGATGGCTCATTCTT<br>TCTGTATTCAAAGCTGACCGTCGATAAATCCAGGTGGCAGCAGGGA<br>AATGTGTTTTCATGCTCCGTGATGCACGAAGCCCTGCACAACCATT<br>ACACCCAGAAGAGCCTGTCCCTGAGCCCCGGCTGA |

TABLE 23

Optimized Nucleic Acid Sequence of Humanized
Anti-human Notch4 Antibody Heavy Chain (HA2 Variable
Region + Human IgG2 Constant Region with
Mutations V234A and G237A and Without C-terminal Lysine)

| Name | Sequence |
|---|---|
| Nucleic acid<br>sequence<br>(SEQ ID NO. 61) | GAAGTGCAGCTGGTCGAGTCTGGGGGGGGCTGGTGCAGCCTGGCG<br>GATCCCTGAGACTGAGCTGCGCCGCTTCTGGGTTCACATTTTCCAG<br>CTACGGCATGTCCTGGGTCCGCCAGGCACCAGGCAAGGGACTGGAG<br>CTGGTGAGTACAATCAACTCAAATGGGGGTCGAACTTACTATGCTA<br>ACTCCGTGAAGGGCAGGTTCACTATTTCCCGGGACAACAGCAAAAA<br>TACCCTGTACCTGCAGATGGGGTCCCTGCGAGCTGAAGACATGGCA<br>GTGTACTATTGTGCCCGTGATCAGGGTTTCGCTTATTGGGGCAGG<br>GTACTCTGGTCACCGTGTCTAGTGCTTCTACCAAGGGGCCCAGTGT<br>GTTTCCACTGGCACCCTGCTCCCGGAGCACATCTGAGAGTACTGCA<br>GCCCTGGGCTGTCTGGTGAAGGATTATTTCCCTGAACCAGTCACAG<br>TGAGCTGGAACTCTGGCGCACTGACAAGCGGAGTCCACACTTTTCC<br>TGCCGTGCTGCAGTCATCCGGCCTGTACTCTCTGAGCTCTGTGGTC<br>ACTGTCCCCAGTTCAAATTTCGGAACTCAGACCTATACATGCAACG<br>TGGACCATAAGCCTAGCAATACCAAGGTCGATAAAACAGTGGAGCG<br>TAAATGCTGTGTGGAATGCCCACCTTGTCCAGCTCCACCAGCTGCA<br>GCCCCTTCTGTGTTCCTGTTTCCTCCAAAGCCAAAAGACACCCTGA<br>TGATCTCTAGAACCCCCGAGGTCACATGTGTGGTCGTGGACGTCAG<br>TCACGAGGATCCAGAAGTCCAGTTTAACTGGTACGTGGATGGCGTC<br>GAAGTGCATAATGCAAAGACAAAACCCAGAGAGGAACAGTTCAACT<br>CAACCTTTCGCGTCGTGTCCGTGCTGACAGTCGTGCACCAGGACTG<br>GCTGAACGGCAAGGAGTATAAGTGCAAAGTGTCCAATAAGGGACTG<br>CCCGCCCCTATCGAGAAAACTATTTCCAAGACCAAAGGACAGCCTA<br>GGGAACCACAGGTGTACACTCTGCCCCCTTCCCGGGAGGAAATGAC<br>TAAGAACCAGGTCAGCCTGACCTGTCTGGTGAAAGGGTTCTATCCT<br>AGTGACATTGCCGTGGAGTGGGAATCAAATGGTCAGCCAGAGAACA<br>ATTACAAGACCACACCCACCCATGCTGGACAGTGATGGCTCATTCTT<br>TCTGTATAGCAAGCTGACCGTCGATAAATCTAGGTGGCAGCAGGGA<br>AATGTGTTTTCATGCTCCGTGATGCACGAAGCCCTGCACAACCACT<br>ACACACAGAAAAGCCTGAGCCTGAGCCCCGGCTGA |

TABLE 24

Optimized Nucleic Acid Sequence of Humanized
Anti-human Notch4 Antibody Light Chain
(L3 Variable Region + Human Igκ Constant Region)

| Name | Sequence |
|---|---|
| Nucleic acid<br>sequence<br>(SEQ ID NO. 62) | GAAATCGTGATGACTCAGTCCCCCGCTACACTGAGCGTGTCTCCCG<br>GAGAGAGAGCTACTCTGTCTTGCAAGGCAAGTCAGGACGTGGGAAC<br>TGCAGTCGCCTGGTACCAGCAGAAACCAGGACAGGCACCACGACTG<br>CTGATCTATTGGGCTAGTACAAGGCACACTGGCATTCCTGCCCGGT<br>TCAGTGGCTCAGGATCCGGGACAGAGTTTACCCTGACAATCTCCAG |

TABLE 24-continued

Optimized Nucleic Acid Sequence of Humanized
Anti-human Notch4 Antibody Light Chain
(L3 Variable Region + Human Igκ Constant Region)

| Name | Sequence |
|---|---|
| | CCTGCAGTCCGAAGATTTCGCTGTGTACTATTGCCAGCAGTACTCT<br>AGTTATCCTTGGACCTTTGGTCAGGGCACAAAGGTCGAGATCAAAC<br>GAACCGTGGCCGCTCCAAGCGTCTTCATTTTTCCCCCTTCTGACGA<br>ACAGCTGAAGTCAGGTACAGCCTCCGTGGTCTGTCTGCTGAACAAT<br>TTCTACCCAAGGGAGGCAAAGGTGCAGTGGAAAGTCGATAACGCCC<br>TGCAGAGCGGCAATTCTCAGGAGAGTGTGACTGAACAGGACTCAAA<br>GGATTCCACCTATAGCCTGTCATCCACTCTGACCCTGAGCAAAGCT<br>GACTACGAAAAGCATAAAGTGTATGCATGTGAAGTCACACACCAGG<br>GTCTGAGTTCTCCAGTCACCAAATCTTTTAATAGAGGCGAGTGCTG<br>A |

TABLE 25

Optimized Nucleic Acid Sequence of Humanized
Anti-human Notch4 Antibody Light Chain
(L4 Variable Region + Human Igκ Constant Region)

| Name | Sequence |
|---|---|
| Nucleic acid<br>sequence<br>(SEQ ID NO. 63) | GAAATCGTGATGACCCAGTCTCCTGCTACACTGAGCGTGTCTCCCG<br>GAGAGAGAGCTACTCTGTCTTGCAAGGCAAGTCAGGACGTGGGAAC<br>TGCAGTCGCCTGGTACCAGCAGAAACCAGGACAGGCACCACGACTG<br>CTGATCTATTGGGCTAGTACAAGGCACACTGGCATTCCTGCCCGGT<br>TCAGTGGCTCAGGATCCGGGACAGAGTTTACCCTGACAATCTCCAG<br>CCTGCAGTCCGAAGATTTCGCTGTGTACTTTTGCCAGCAGTACTCT<br>AGTTATCCTTGGACCTTCGGTCAGGGCACAAAGGTCGAGATCAAAC<br>GAACCGTGGCCGCTCCAAGCGTCTTCATTTTTCCCCCTTCTGACGA<br>ACAGCTGAAGTCAGGTACAGCCTCCGTGGTCTGTCTGCTGAACAAT<br>TTTTACCCAAGGGAGGCAAAGGTGCAGTGGAAAGTCGATAACGCCC<br>TGCAGAGCGGCAATTCTCAGGAGAGTGTGACTGAACAGGACTCAAA<br>GGATTCCACCTATAGCCTGTCATCCACTCTGACCCTGAGCAAAGCT<br>GACTACGAAAAGCATAAAGTGTATGCATGTGAAGTCACACACCAGG<br>GTCTGTCCAGTCCAGTCACCAAATCCTTTAATCGGGGAGAGTGCTG<br>A |

TABLE 26

Optimized Nucleic Acid Sequence of Humanized
Anti-human Notch4 Antibody Light Chain
(L5 Variable Region + Human Igκ Constant Region)

| Name | Sequence |
|---|---|
| Nucleic acid<br>sequence<br>(SEQ ID NO. 64) | GATATTCAGATGACCCAGTCTCCTTCCAGCCTGTCTGCAAGTGTGG<br>GAGACAGGGTCACCATCACATGCAAAGCCTCCCAGGATGTGGGAAC<br>CGCAGTCGCCTGGTACCAGCAGAAGCCAGGGAAAAGCCCCAAGCTG<br>CTGATCTACTGGGCTTCTACCAGGCACACAGGCGTGCCAAGTCGGT<br>TCTCAGGCTCCGGAAGCGGGACCGACTTTACTCTGACCATCTCCAG<br>CCTGCAGCCTGAGGATGTGGCAACATACTTCTGCCAGCAGTACTCT<br>AGTTATCCATGGACTTTTGGTCAGGGCACCAAAGTCGAGATCAAGA<br>GAACTGTGGCCGCTCCCTCCGTCTTCATTTTTCCCCCTAGCGACGA<br>ACAGCTGAAGAGTGGTACAGCCTCAGTGGTCTGTCTGCTGAACAAT<br>TTCTACCCTAGGGAGGCTAAAGTGCAGTGGAAGGTCGATAACGCAC<br>TGCAGTCTGGCAATAGTCAGGAGTCAGTGACAGAACAGGACTCCAA<br>AGATAGCACTTATTCTCTGTCATCCACACTGACTCTGTCTAAGGCC<br>GACTACGAAAAGCATAAAGTGTATGCTTGTGAGGTCACACACCAGG<br>GTCTGAGCAGTCCAGTCACCAAGAGCTTTAACCGAGGAGAGTGCTG<br>A |

TABLE 27

Optimized Nucleic Acid Sequence of Humanized
Anti-human Notch4 Antibody Light Chain
(L6 Variable Region + Human Igκ Constant Region)

| Name | Sequence |
|---|---|
| Nucleic acid sequence (SEQ ID NO. 65) | GAAATCGTGATGACCCAGTCTCCTGCTACACTGAGCGTGTCTCCCG GAGAGAGAGCTACTCTGTCTTGCAAGGCAAGTCAGGACGTGGGAAC TGCAGTCGCCTGGTACCAGCAGAAACCAGGGCAGAGTCCCCGCCTG CTGATCTATTGGGCCTCCACAAGGCACACTGGCATTCCTGCTCGGT TCAGTGGCTCAGGATCCGGGACAGAGTTTACCCTGACAATCTCCAG CCTGCAGAGCGAAGATTTCGCCGTGTACTTTTGCCAGCAGTACTCT AGTTATCCTTGGACCTTCGGTCAGGGCACAAAGGTCGAGATCAAAC GAACCGTGGCCGCTCCAAGCGTCTTCATTTTTCCCCCTTCTGACGA ACAGCTGAAGTCAGGTACAGCTTCCGTGGTCTGTCTGCTGAACAAT TTTTACCCAAGGGAGGCAAAGGTGCAGTGGAAAGTCGATAACGCCC TGCAGAGCGGCAATTCTCAGGAGAGTGTGACTGAACAGGACTCAAA GGATTCCACCTATAGCCTGTCATCCACTCTGACCCTGTCTAAAGCT GACTACGAAAAGCATAAAGTGTATGCATGTGAAGTCACCCACCAGG GGCTGAGTAGTCCAGTCACCAAGAGTTTTAATCGGGGCGAGTGTTG A |

In the following Examples, experiments were carried out with antibodies comprising the amino acid sequence of CDR of antibody 6-3-A6 determined in Example 1.

For convenience, the specific antibodies employed in the following Example will be referred to as "Antibody A," "Antibody B," "Antibody C," "Antibody D," "Antibody E," "Antibody F," and "Antibody G."

In Antibody A, the heavy chain variable region comprises the heavy chain variable region of HK2 described in Example 1 and the light chain variable region comprises the light chain variable region of L3 described in Example 1.

In Antibody B, the heavy chain variable region comprises the heavy chain variable region of HK3 described in Example 1 and the light chain variable region comprises the light chain variable region of L3 described in Example 1.

In Antibody C, the heavy chain variable region comprises the heavy chain variable region of HK2 described in Example 1 and the light chain variable region comprises the light chain variable region of L4 described in Example 1.

In Antibody D, the heavy chain variable region comprises the heavy chain variable region of HK3 described in Example 1 and the light chain variable region comprises the light chain variable region of L5 described in Example 1.

In Antibody E, the heavy chain variable region comprises the heavy chain variable region of HK2 described in Example 1 and the light chain variable region comprises the light chain variable region of L6 described in Example 1.

In Antibody F, the heavy chain variable region comprises the heavy chain variable region of HA2 described in Example 1 and the light chain variable region comprises the light chain variable region of L3 described in Example 1.

In Antibody G, the heavy chain variable region comprises the heavy chain variable region of HK3 described in Example 1 and the light chain variable region comprises the light chain variable region of L4 described in Example 1.

Note that in Antibodies A-G, lysine (Lys) that is located at the C-terminal of the heavy chain of a common human antibody is deleted.

Example 2: Neutralizing Activity of Anti-Human Notch4 Antibody

The neutralizing activity of anti-human Notch4 antibody (Antibody B) was evaluated with Notch4-GAL4 *luciferase* reporter assay. This experiment is an experiment system that evaluates signal transduction specific to Notch4 by evaluating the *luciferase* activity when b. end3 cell line in which a modified gene having a part of Notch4 intracellular domain substituted with GAL4 DNA binding domain as well as a fused gene expression vector between GAL4 UAS and *Luciferase* 2CP introduced (hereinafter referred as a "reporter cell") is stimulated with DLL4, which is a Notch ligand.

Recombinant human DLL4 (R&D Systems, 1506-D4-050/CF) was dissolved in PBS to prepare a 10 μg/mL solution (hereinafter DLL4 solution). To a flat-bottomed 96-well white plate (Greiner, 655083), 50 μL/well (500 ng/well) of the DLL4 solution and 50 μL/well of PBS for non-stimulated wells were each dispensed, and this was left overnight at 4° C. to allow DLL4 to be solid phased to the 96-well white plate. The reporter cells were suspended in a D-MEM culture medium comprising 10% Fetal Bovine Serum (FBS) and penicillin/streptomycin to prepare a cell suspension at $1\times10^5$/mL. Each well with solid phased DLL4 was washed three times with PBS, and 50 μL/well (5,000 cells/well) of the cell suspension was seeded. Anti-human Notch4 antibody dilutions (final concentrations: 0, 0.00064, 0.0032, 0.016, 0.08, 0.4, 2, and 10 μg/mL) or Human IgG2 κ (SIGMA, 15404, final concentration: 10 μg/mL) were each added at 50 μL, and this was cultured at 37° C. for 22 hours. The *luciferase* activity of the reporter cells was evaluated with Steady-Glo Assay System (Promega, E2510) as follows.

One hundred microliters of Steady-Glo solution was added to each well after culturing, stirred, and then left at room temperature for 30 minutes. Luminescence was measured with Multilabel Plate Reader (Envision 2102-0020, Perkin Elmer). Relative luminescence (%) was calculated from the measured luminescence value by the following formula.

Relative luminescence (%)=(Luminescence intensity of the specimen well–Average luminescence intensity of non-stimulated wells)/(Average luminescence intensity of control wells–Average luminescence intensity of non-stimulated wells)

Figure 1:
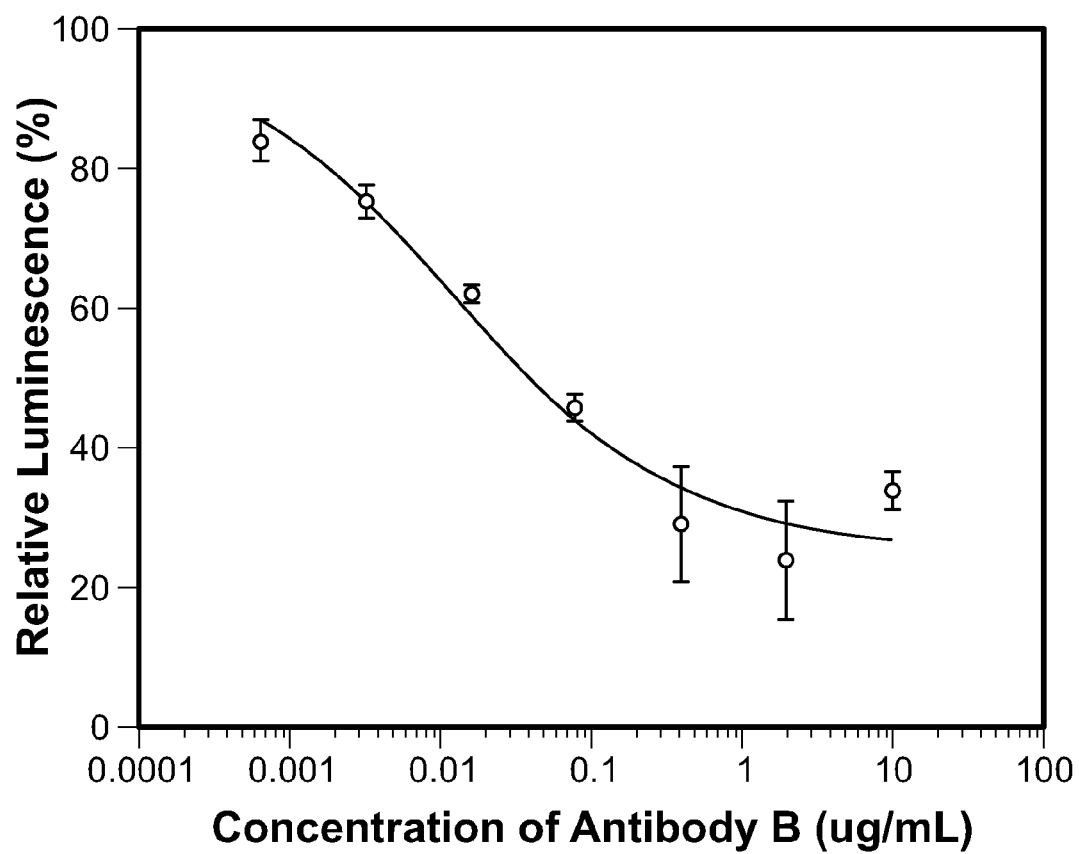
FIG. 1 shows the relationship between the concentration of Antibody B and the relative luminescence (%) value.

The relationship between the concentration of Antibody B and the relative luminescence (%) value is shown in FIG. 1. The graph in FIG. 1 shows the average value of three independent test results, and the error bar shows the standard deviation thereof. IC50 was 0.011 μg/mL (95% CI; 0.0036-0.034).

Next, similar experiments were performed for a plurality of anti-human Notch4 antibodies including Antibody B (Antibody A, Antibody B, Antibody C, Antibody D, Antibody E, Antibody F, and Antibody G), and the neutralizing activity of the antibodies were measured.

Recombinant human DLL4 (R&D Systems, 1506-D4-050/CF) was dissolved in PBS to prepare a 10 µg/mL solution (hereinafter DLL4 solution). To a flat-bottomed 96-well white plate (Greiner, 655083), 50 µL/well (500 ng/well) of the DLL4 solution and 50 µL/well of PBS for non-stimulated wells were each dispensed, and this was left overnight at 4° C. to allow DLL4 to be solid phased to the 96-well white plate. The reporter cells were suspended in a D-MEM culture medium comprising 10% Fetal Bovine Serum (FBS) and penicillin/streptomycin to prepare a cell suspension at 1×10^5/mL. Each well with solid phased DLL4 was washed three times with PBS, and 50 µL/well (5,000 cells/well) of the cell suspension was seeded. Each anti-human Notch4 antibody dilution (final concentrations: 0 and 10 µg/mL) or Human IgG2 κ (SIGMA, 15404, final concentration: 10 µg/mL) was added at 50 µL, and this was cultured at 37° C. for 22 hours. The *luciferase* activity of the reporter cells was evaluated with Dual luc-Glo Assay System (Promega, E2940) as follows.

One hundred microliters of Dual-Glo *Luciferase* Substrate solution was added to each well after culturing, stirred, and then left at room temperature for 20 minutes. Luminescence of firefly *luciferase* was measured with Multilabel Plate Reader (Envision 2102-0020, Perkin Elmer). Next, 100 µL of Dual-Glo Stop & Glo Substrate solution was added to each well, stirred, and then left at room temperature for 20 minutes. Luminescence of *Renilla luciferase* was measured with Multilabel Plate Reader (Envision 2102-0020, Perkin Elmer). Relative Luminescence of each well (firefly *luciferase/Renilla luciferase*) was calculated from the ratio of luminescence values. Further, relative luminescence (%) was calculated from each calculated value using the following formula, and Notch4 signal inhibitory activity of each antibody was evaluated.

Relative luminescence (%)=(Average relative luminescence of specimen wells−Average relative luminescence of non-stimulated wells)/(Average relative luminescence of control wells−Average relative luminescence of non-stimulated wells)

Notch4 signal inhibitory activity of each antibody (tests performed at 10 µg/ml concentration) is described in Table 28 below.

In the table below, e.g. the description "HK2L3 (Lys-)" means that the heavy chain variable region of the humanized anti-human Notch4 antibody employed in the experiment is the heavy chain variable region of the humanized anti-human Notch4 antibody heavy chain HK2 in Example 1, light chain variable region is the light chain variable region of the humanized anti-human Notch4 antibody light chain L3 in Example 1, and lysine (Lys) located at the C-terminal of the heavy chain of a common human antibody is deleted in this antibody.

TABLE 28

| Sample | H/L chain | % of Control | S.D. | p value |
|---|---|---|---|---|
| Antibody A | HK2L3 (Lys-) | 0.1 | 3.2 | 5.9E−11 |
| Antibody B | HK3L3 (Lys-) | 10.8 | 11.4 | 8.3E−07 |
| Antibody C | HK2L4 (Lys-) | −9.9 | 14.0 | 8.0E−07 |
| Antibody D | HK3L5 (Lys-) | 21 | 8 | 1.8E−07 |

TABLE 28-continued

| Sample | H/L chain | % of Control | S.D. | p value |
|---|---|---|---|---|
| Antibody E | HK2L6 (Lys-) | 5 | 3 | 1.7E−11 |
| Antibody F | HA2L3 (Lys-) | 17 | 5 | 3.5E−09 |
| Antibody G | HK3L4 (Lys-) | 13 | 9 | 2.4E−07 |

Example 3: Kinetic Analysis of Binding of Humanized Anti-Notch4 Antibody to Recombinant Notch4-NRR Domain Protein Kinetic analysis of the interaction of human, cynomolgus monkey, mouse, and rat Notch4-NRR domains with Antibody B was carried out with BIACORE. Antibody B was purified with protein A affinity chromatography from the culture supernatant of a stable CHO cell line transfected with Antibody B. Human, monkey, mouse, and rat Notch4-NRR domains were prepared as fusion proteins with secretory alkaline phosphatase (SEAP) and 10× histidine tag. The genes for these proteins were transfected into Expi293F cells in Opti-MEM (INVITROGEN) using ExpiFectamine 293. These cells were cultured in Expi293 Expression Medium (INVITROGEN). Briefly, cells were diluted to $7.5 \times 10^7$ cells/25.5 mL, and transfected by ExpiFectamine 293 reagent on Day 0. About 16 hours after transfection, 150 uL of ExpiFectamine 293 Transfection Enhancer 1 and 1.5 mL of ExpiFectamine 293 Transfection Enhancer 2 were added to each flask. The supernatant was collected on Day 4. These antigens were purified with Ni-NTA Superflow column (QIAGEN). The interaction was analyzed as below. The purified Antibody B was captured by anti-human IgG Fc antibody fixed on a CM5 sensor chip (GE healthcare). The purified Notch4-NRR fusion proteins were injected onto the sensor chip at 8 different concentrations, and the interaction and dissociation thereof were observed as per manufacturer's instructions.

TABLE 29

Calculated Kinetic Parameters of Antibody B

| Protein | Ka (1/Ms) | Kd (1/s) | KD (M) |
|---|---|---|---|
| Human Notch4-NRR | 3.17E+05 | 1.18E−03 | 3.74E−09 |
| Cynomolgus monkey Notch4-NRR | 2.95E+05 | 1.06E−03 | 3.62E−09 |
| Mouse Notch4-NRR | 6.01E+05 | 7.27E−03 | 1.12E−08 |
| Rat Notch4-NRR | ND | ND | ND |

Kinetic analysis of further anti-Notch4 inhibitory humanized antibodies was carried out as follows. Human Notch4-NRR domain Fc fusion proteins were expressed with a CHO cell line. The antigen in the culture supernatant was captured by the anti-human Notch4 antibody fixed on a CM5 sensor chip that recognizes different epitopes of human Notch4. The humanized anti-human Notch4 antibody was then injected onto the sensor chip at various concentrations. The interaction and disassociation constants thereof were calculated according to manufacturer's instructions. The results are shown in Table 30.

In the table below, e.g. the description "HK2L3 (Lys-)" means that the heavy chain variable region of the humanized anti-human Notch4 antibody employed in the experiment is the heavy chain variable region of the humanized anti-human Notch4 antibody heavy chain HK2 in Example 1, light chain variable region is the light chain variable region of the humanized anti-human Notch4 antibody light chain L3 in Example 1, and lysine (Lys) located at the C-terminal of the heavy chain of a common human antibody is deleted in this antibody. Those without the description "(Lys-)" mean that Lys located at the C-terminal of the heavy chain of the human antibody is not deleted.

TABLE 30

Calculated Kinetic Parameters of Humanized Anti-Notch4 Inhibitory Antibodies Against Human Notch4-NRR Fusion Protein

| Sample | H/L Chain | ka (1/Ms) | kd (1/s) | KD (M) | Rmax1 (RU) |
|---|---|---|---|---|---|
| Antibody A | HK2L3(Lys-) | 1.62E+06 | 8.89E−04 | 5.55E−10 | 33.4 |
| Antibody B | HK3L3(Lys-) | 1.66E+06 | 7.10E−04 | 4.41E−10 | 26.2 |
| Antibody C | HK2L4(Lys-) | 1.91E+06 | 1.06E−03 | 5.56E−10 | 35.9 |
| Antibody D | HK3L5(Lys-) | 1.82E+06 | 8.63E−04 | 4.75E−10 | 37 |
| Antibody E | HK2L6(Lys-) | 2.23E+06 | 1.15E−03 | 5.19E−10 | 28.9 |
| Antibody F | HA2L3(Lys-) | 1.55E+06 | 1.36E−03 | 9.82E−10 | 20.2 |
| Antibody G | HK3L4(Lys-) | 1.78E+06 | 1.11E−03 | 6.33E−10 | 29.2 |

Experimental results of experiments similar to the above Table 30 performed with further more antibodies are shown in Table 31.

TABLE 31

| No. | HL construct | ka (averaged) | kd (averaged) | KD (averaged) | N |
|---|---|---|---|---|---|
| 6-3-A6 | Original | 2.35E+06 | 7.42E−04 | 3.21E−10 | 9 |
| 37 | HK3L3(Lys-) | 2.48E+06 | 8.22E−04 | 3.31E−10 | 2 |
| 34 | HK2L3(Lys-) | 5.05E+06 | 1.24E−03 | 3.95E−10 | 2 |
| 31 | HA2L3(Lys-) | 3.50E+06 | 8.94E−04 | 4.34E−10 | 2 |
| 39 | HK3L5(Lys-) | 2.10E+06 | 1.09E−03 | 5.29E−10 | 5 |
| 15 | HK2L5 | 2.07E+06 | 1.12E−03 | 5.49E−10 | 6 |
| 20 | HK3L5 | 1.72E+06 | 1.02E−03 | 6.01E−10 | 6 |
| 30 | HA2L5 | 2.49E+06 | 1.36E−03 | 6.12E−10 | 6 |
| 36 | HK2L5(Lys-) | 1.93E+06 | 1.13E−03 | 6.17E−10 | 5 |
| 41 | HK2L6(Lys-) | 1.87E+06 | 1.15E−03 | 6.20E−10 | 3 |
| 14 | HK2L4 | 1.89E+06 | 1.17E−03 | 6.34E−10 | 6 |
| 13 | HK2L3 | 1.62E+06 | 1.09E−03 | 6.82E−10 | 6 |
| 35 | HK2L4(Lys-) | 1.81E+06 | 1.27E−03 | 7.15E−10 | 5 |
| 28 | HA2L3 | 1.95E+06 | 1.37E−03 | 7.27E−10 | 6 |
| 29 | HA2L4 | 2.33E+06 | 1.69E−03 | 7.38E−10 | 6 |
| 19 | HK3L4 | 1.61E+06 | 1.20E−03 | 7.55E−10 | 6 |
| 38 | HK3L4(Lys-) | 1.86E+06 | 1.24E−03 | 7.60E−10 | 5 |
| 42 | HK3L6(Lys-) | 1.51E+06 | 1.14E−03 | 7.66E−10 | 3 |
| 33 | HA2L5(Lys-) | 2.01E+06 | 1.50E−03 | 7.76E−10 | 3 |
| 32 | HA2L4(Lys-) | 2.43E+06 | 1.62E−03 | 8.30E−10 | 5 |
| 40 | HA2L6(Lys-) | 1.83E+06 | 1.51E−03 | 8.38E−10 | 3 |
| 18 | HK3L3 | 1.22E+06 | 1.04E−03 | 8.97E−10 | 6 |
| 17 | HK3L2 | 1.13E+06 | 1.45E−03 | 1.29E−09 | 4 |
| 12 | HK2L2 | 1.23E+06 | 1.57E−03 | 1.38E−09 | 4 |
| 27 | HA2L2 | 1.63E+06 | 2.22E−03 | 1.41E−09 | 4 |
| 16 | HK3L1 | 7.83E+05 | 1.33E−03 | 1.76E−09 | 4 |
| 26 | HA2L1 | 9.49E+05 | 1.66E−03 | 1.76E−09 | 4 |
| 10 | HK1L5 | 2.72E+06 | 4.89E−03 | 1.78E−09 | 3 |
| 11 | HK2L1 | 8.75E+05 | 1.60E−03 | 1.84E−09 | 4 |
| 9 | HK1L4 | 2.78E+06 | 1.18E−02 | 4.34E−09 | 2 |
| 8 | HK1L3 | 3.71E+06 | 1.96E−02 | 4.87E−09 | 2 |
| 25 | HA1L5 | 6.36E+06 | 4.52E−02 | 7.20E−09 | 2 |
| 24 | HA1L4 | 1.18E+07 | 1.13E−01 | 9.54E−09 | 1 |
| 23 | HA1L3 | 3.57E+07 | 5.24E−01 | 1.47E−08 | 1 |
| 22 | HA1L2 | 6.49E+05 | 1.22E−02 | 1.86E−08 | 2 |
| 21 | HA1L1 | 6.15E+04 | 2.79E−02 | 4.53E−07 | 1 |

Example 4: In Vivo Pharmacological Test Employing Anti-Human Notch4 Antibody (Antitumor Effect and Blood Perfusion Suppressive Effect of Antibody B in Calu6 Xenograft Model)

Human non-small cell lung cancer cell line Calu6 (ATCC number HTB-56) cultured in an EMEM culture medium comprising 10% FBS, MEM non-essential amino acids, sodium pyruvate, and penicillin/streptomycin was prepared to a concentration of $1.6 \times 10^8$ cells/mL with EMEM culture medium, and mixed with Matrigel™ (CORNING Cat#354234) at 1:1 to prepare a cell suspension of $8.0 \times 10^7$ cells/mL. A dose of 0.1 mL was subcutaneously transplanted to the right posterior dorsal region of 6 weeks-old nude mice (CAnN.Cg-Foxn1nu/CrlCrlj, female, CHARLES RIVER LABORATORIES JAPAN, INC.) Twenty-eight days after transplantation, minor and major axes of the tumor were measured with an electronic digital caliper (DIGIMATIC™ CALIPER, Mitsutoyo Corporation), and the tumor volume TV was calculated with the following calculation formula.

$$TV\ (mm^3) = Major\ axis\ (mm) \times Minor\ axis\ (mm) \times Minor\ axis\ (mm)/2$$

Figure 2A:
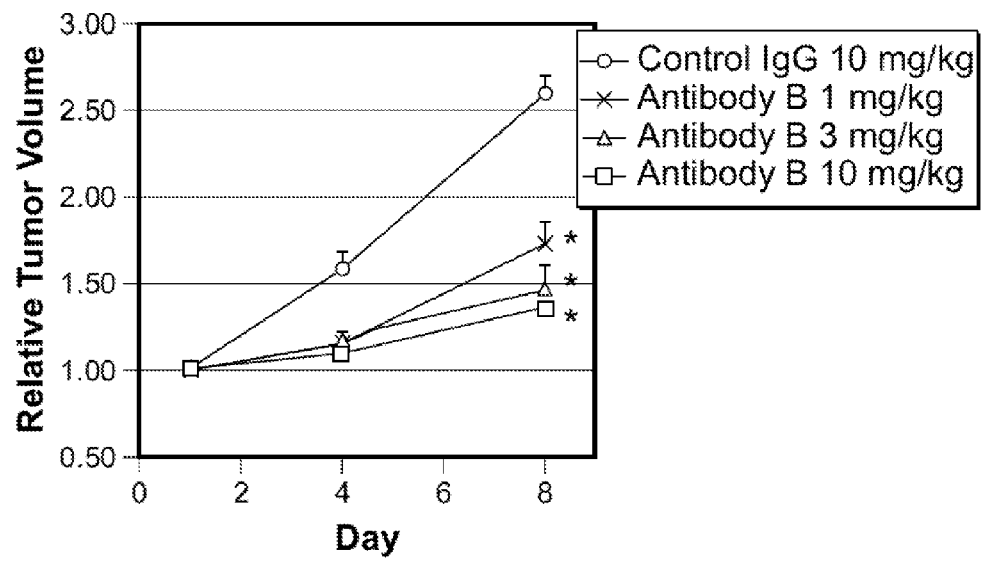
FIGS. 2A and 2B show the antitumor effect and blood perfusion suppressive effect of Antibody B in a Calu6 xenograft model.

Randomization was carried out based on the tumor volume on the first day of administration so that the average value of the tumor volumes will be approximately equal among the groups. Antibody B was diluted immediately before administration so that vehicle solution (25 mM Histidine, 250 mM Sucrose, and 0.05% Tween80 (pH5.3)) and saline is 1:9 to obtain 0.1, 0.3, and 1.0 mg/mL evaluation specimens (1, 3, and 10 mg/kg administration group, respectively). Evaluation specimens were administered by tail vein injection at a dosage of 0.2 mL/20 g of mouse body weight twice a week (Day 1 and Day 4 when counting the day of grouping as Day 1). For the control group, 11.6 mg/mL of Control IgG (ChromPure Human IgG, whole molecule, Jackson ImmunoResearch Laboratories, Cat#009-000-003) was diluted with PBS to 1.0 mg/mL, and administered by tail vein injection at 0.2 mL/20 g of mouse body weight (administration volume 10 mg/kg). The experiment was performed with 8 mice per group. Relative tumor volume RTV was calculated for each of the Control IgG group and Antibody B administration group with the following formula and shown in FIG. 2A.

$$RTV = Tumor\ volume\ on\ the\ day\ of\ measurement/\ Tumor\ volume\ at\ the\ start\ of\ administration$$

Antibody B showed significant antitumor effect at all dosages in Calu6 xenograft model.

Tumor blood perfusion was evaluated by determining the fluorescence by nucleus staining of cells around blood vessels due to a fluorescent dye (Hoechst) injected in the tail vein (Funahashi et al. (2014), Cancer Sci., 105(10), 1334-42.). After measuring the tumor diameter on the final test day, 10 mg/mL of Hoechst 33342 (Life technologies Cat# H3570) was diluted to 2x with PBS, and 5.0 mg/mL of the diluted Hoechst 33342 was injected in the tail vein at 0.1 mL/head. Mice were euthanized by cervical dislocation 5 minutes after injecting Hoechst, and the collected tumors were embedded in OCT Compound (Sakura Finetek Japan Co., Ltd. Cat#4583) to produce frozen blocks.

Figure 2B:
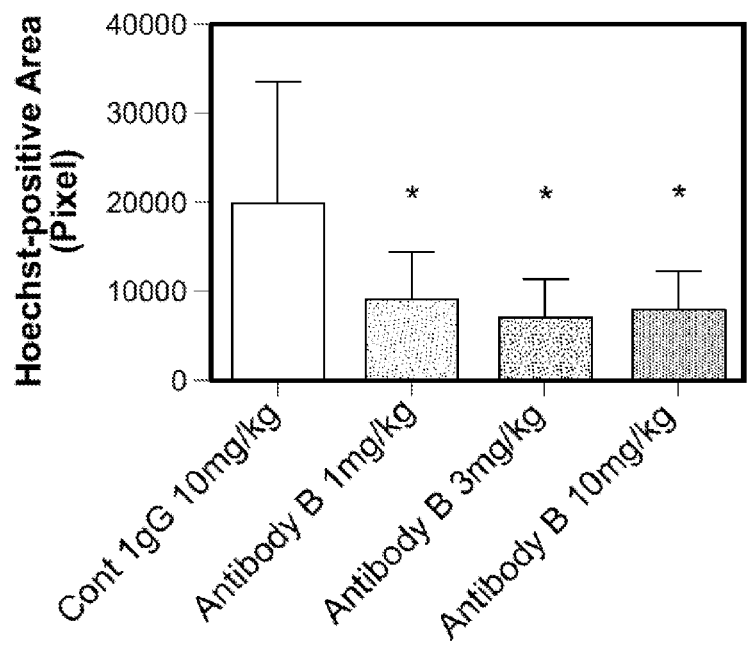

Tumor blood vessels of frozen sections were subjected to immunofluorescent staining with anti-CD31 antibody (FITC conjugated, BD Pharmingen Cat#553372), and Hoechst fluorescence of tumor blood vessel hotspots (5 per tumor) were photographed with BIOREVO fluorescence microscope (KEYENCE, BZ-9000). Hoechst-positive area was determined with an image analysis software (Lumina Vision ver 2.2.2, MITANI CORPORATION), and the average of each tumor section was calculated and shown in FIG. 2B.

Antibody B showed significant blood perfusion suppressive effect at all dosages in Calu6 xenograft model.

Example 5: Combination Use of Antibody B and Cisplatin in Calu6 Xenograft Model

Human non-small cell lung cancer cell line Calu6 (ATCC number HTB-56) cultured in an EMEM culture medium comprising 10% FBS and penicillin/streptomycin was prepared to a concentration of $1.2 \times 10^8$ cells/mL with EMEM culture medium, and mixed with Matrigel™ (CORNING Cat#354234) at 1:1 to prepare a cell suspension of $6.0 \times 10^7$ cells/mL A dose of 0.1 mL was subcutaneously transplanted to the right posterior dorsal region of 7 weeks-old nude mice (CAnN.Cg-Foxn1nu/CrlCrlj, female, CHARLES RIVER LABORATORIES JAPAN, INC.) Twenty-seven days after transplantation, minor and major axes of the tumor were measured with an electronic digital caliper (DIGIMATIC™ CALIPER, Mitsutoyo Corporation), and the tumor volume TV was calculated with the following calculation formula.

Tumor volume TV (mm$^3$)=Major axis (mm)×Minor axis (mm)×Minor axis (mm)/2

Figure 3:
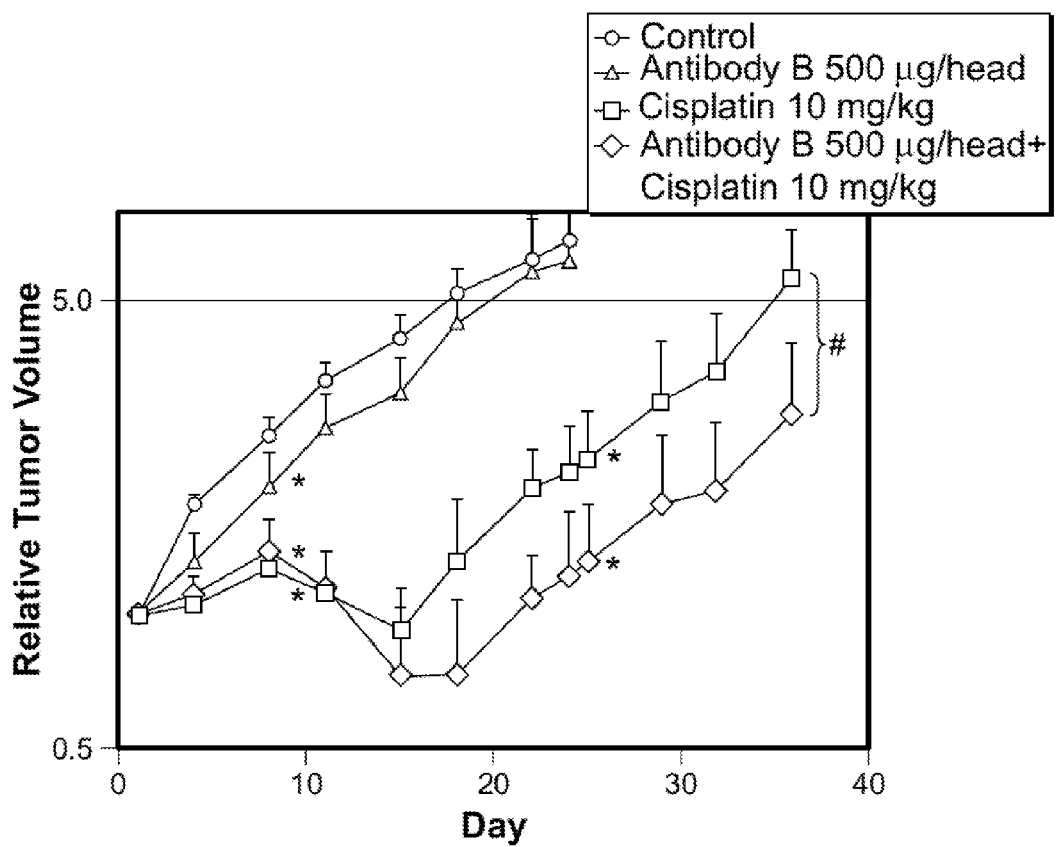
FIG. 3 shows the antitumor effect due to the combination use of Antibody B and cisplatin in a Calu6 mouse subcutaneous transplantation model. The change in relative tumor volume (RTV) of the control (non-treated) group, Antibody B administration group (twice-a-week tail vein administration), cisplatin administration group (one-time tail vein administration), and Antibody B (twice-a-week tail vein administration)+cisplatin (one-time tail vein administration) combination group (N=4, mean±standard error) (*: P<0.05 vs control group (Student's t-test, Day 8, Day 24), #: P<0.05 cisplatin 10 mg/kg administration group vs Antibody B+cisplatin combination group (Student's t-test, Day 36)).

Randomization was carried out based on the tumor volume on the first day of administration so that the average value of tumor volumes will be approximately equal among the groups. For Antibody B, a 10.34 mg/mL solution (vehicle: 25 mM Phosphate, 200 mM Trehalose, and 0.05% Tween80 (pH 5.5)) was diluted immediately before administration with PBS to prepare a solution at 2.5 mg/mL, and this was administered by intravenous injection at a dosage of 0.2 mL (500 µg)/head, twice a week for 5 weeks. Cisplatin was administered once on the first day of administration by tail vein administration at a dose of 10 mg/kg. The experiment was performed with 4 mice per group. The relative tumor volume RTV was calculated for each of the control (non-treated) group, Antibody B administration group, cisplatin administration group, and Antibody B+cisplatin combination group with the following formula and shown in FIG. 3.

RTV=Tumor volume on the day of measurement/ Tumor volume at the start of administration The combination use of Antibody B and cisplatin showed significantly superior antitumor effect compared to cisplatin alone in Calu6 xenograft model.

Example 6: Combination Use of Antibody B and Lenvatinib Mesylate in FTC238 Xenograft Model Human thyroid cancer cell line FTC238 (purchased from Sumitomo Dainippon Pharma Co., Ltd.) cultured in an DMEM/HAM's F12 (1:1) culture medium comprising 10% FBS and penicillin/streptomycin was prepared to a concentration of $1.2 \times 10^8$ cells/mL with DMEM/HAM's F12 (1:1) culture medium, and mixed with Matrigel™ (CORNING Cat#354234) at 1:1 to prepare a cell suspension of $6.0 \times 10^7$ cells/mL. A dose of 0.1 mL was subcutaneously transplanted to the right flank of 7 weeks-old nude mice (CAnN.Cg-Foxn1nu/CrlCrlj, female, CHARLES RIVER LABORATORIES JAPAN, INC.) Eight days after transplantation, minor and major axes of the tumor were measured with an electronic digital caliper (DIGIMATIC™ CALIPER, Mitsutoyo Corporation), and the tumor volume TV was calculated with the following calculation formula.

Tumor volume TV (mm$^3$)=Major axis (mm)×Minor axis (mm)×Minor axis (mm)/2

Figure 4:
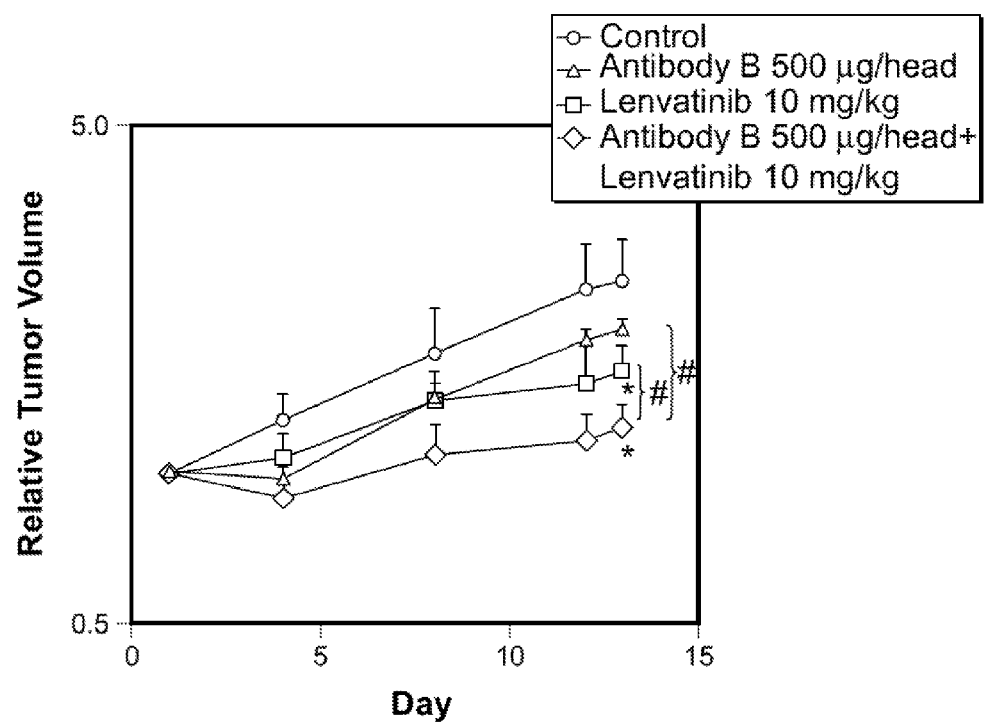
FIG. 4 shows the antitumor effect due to the combination use of Antibody B and lenvatinib mesylate in a FTC238 human thyroid cancer cell line xenograft model. The change in relative tumor volume (RTV) (N=5, mean±standard error) of the control (non-treated) group, Antibody B administration group (twice-a-week tail vein administration), lenvatinib mesylate administration group (once-a-day oral administration), and Antibody B (twice-a-week tail vein administration)+lenvatinib mesylate (once-a-day oral administration) combination group (*: P<0.05 vs control group (Student's t-test, Day 13), #: P<0.05 single agent administration group vs Antibody B+lenvatinib mesylate combination group (Student's t-test, Day 13)).

Randomization was carried out based on the tumor volume on the first day of administration so that the average value of tumor volumes will be approximately equal among the groups. For Antibody B, 10.8 mg/mL Antibody B (vehicle: 25 mM Histidine and 250 mM Sucrose (pH 5.3)) was diluted immediately before administration with the vehicle solution to prepare 2.5 mg/mL Antibody B, and this was administered by tail vein injection at a dosage of 0.2 mL (500 µg)/head, twice a week for 2 weeks. Lenvatinib mesylate was orally administered at a dose of 10 mg/kg, once a day for 12 days. The experiment was performed with 5 mice per group. The relative tumor volume RTV was calculated for each of the control (non-treated) group, Antibody B administration group, lenvatinib mesylate administration group, and Antibody B+lenvatinib mesylate combination group with the following formula and shown in FIG. 4.

RTV=Tumor volume on the day of measurement/ Tumor volume at the start of administration The combination use of Antibody B and lenvatinib mesylate showed significantly superior antitumor effect compared to Antibody B administered alone or lenvatinib mesylate alone in FTC238 xenograft model.

Example 7: Combination Use of Mouse Antibody 6-3-A6 and Paclitaxel in DU145 Xenograft Model Human prostate cancer cell line DU145 (ATCC number HTB-81) cultured in a RPMI1640 culture medium comprising 10% FBS, sodium pyruvate, 2-mercaptoethanol, and penicillin/streptomycin was prepared to a concentration of $6.0 \times 10^7$ cells/mL with RPMI1640 culture medium. A dose of 0.1 mL was subcutaneously transplanted to the right flank of 6 weeks-old nude mice (CAnN.Cg-Foxn1nu/CrlCrlj, female, CHARLES RIVER LABORATORIES JAPAN, INC.) Twenty-four days after transplantation, minor and major axes of the tumor were measured with an electronic digital caliper (DIGIMATIC™ CALIPER, Mitsutoyo Corporation), and the tumor volume TV was calculated with the following calculation formula.

Tumor volume TV (mm$^3$)=Major axis (mm)×Minor axis (mm)×Minor axis (mm)/2

Figure 5:
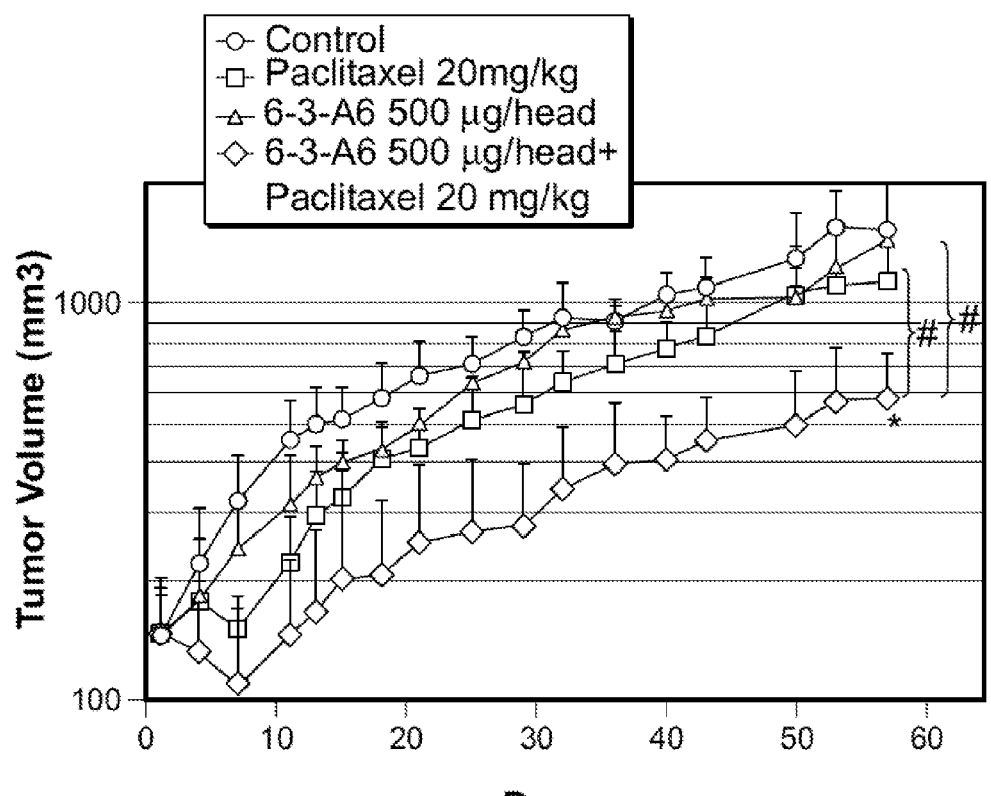
FIG. 5 shows the antitumor effect due to the combination use of Antibody B and paclitaxel in a DU145 human prostate cancer cell line xenograft model. The change in tumor volume (TV) of the control (non-treated) group, Antibody B administration group (twice-a-week tail vein administration), paclitaxel administration group (once-a-day 5-day tail vein administration), and Antibody B (twice-a-week tail vein administration)+paclitaxel (once-a-day 5-day tail vein administration) combination group (N=4, mean±standard error) (*: P<0.05 vs control group (Student's t-test, Day 57), #: P<0.05 single agent administration group vs Antibody B+paclitaxel combination group (Student's t-test, Day 57).
Figure 6:
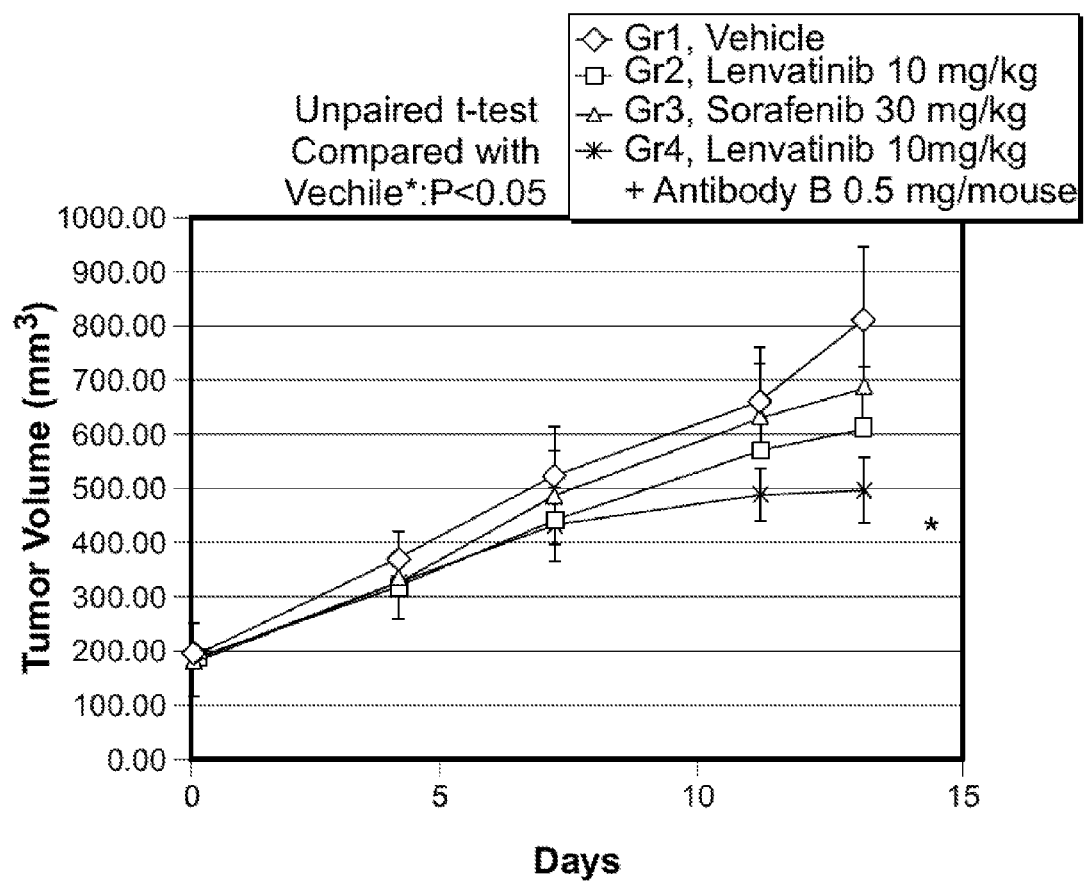
FIG. 6 shows the antitumor effect due to the combination use of Antibody B and lenvatinib mesylate in a human patient deribed hepatocellular carcinoma xenograft model. The change in tumor volume (TV) of the control (3 mam HCl) group, lenvatinib mesilate (10 mg/kg) gorop, sorafenib tosylate (30 mg/kg) group, and lenvatinib mesilate (10 mg/kg) plus Antibody B (0.5 mg/mouse) group (N=10, mean±standard error) (*: P<0.05 vs control group, unpaired t-test, Day 13).

Randomization was carried out based on the tumor volume on the first day of administration so that the average value of tumor volumes will be approximately equal among the groups. For 6-3-A6, 5.11 mg/mL 6-3-A6 (vehicle: PBS) was diluted immediately before administration with PBS to prepare 2.5 mg/mL 6-3-A6, and this was administered by tail vein injection at a dosage of 0.2 mL (500 µg)/head, twice a week for 4 weeks. Paclitaxel was administered by tail vein administration at a dose or 20 mg/kg, once a day for 5 days. The experiment was performed with 4 mice per group. The tumor volume TV of each of the control (non-treated) group, 6-3-A6 administration group, paclitaxel administration group, and 6-3-A6+paclitaxel combination group are shown in FIG. 5.

The combination use of 6-3-A6 and paclitaxel showed significantly superior antitumor effect compared to 6-3-A6 alone or paclitaxel alone in DU145 xenograft model.

Example 8: Combination of Antibody B with Lenvatinib Mesilate in Hepetocellular Carcinoma Patient Derived Xenograft Model To examine the antitumor effect of Antibody B on hepatocellualr carcinoma (HCC), LI0050, a HuPrime® patient derived xenograft model (Crown Bioscience Inc.), was used. The LI0050 is a model mouse inoculated with primary tumor tissues from a female HCC patient, which has been reported sorafenib resistant (International Patent Pamphlet WO2015/031604).

Tumor fragments from LI0050 stock mice were harvested and a fragment of 2-4 mm in diameter was inoculated subcutaneously into the right flank of BALB/c nude mice for tumor development. Tumor size was measured in two dimensions using a caliper, and the tumor volume TV was calculated with the following calculation formula.

Tumor volume TV (mm$^3$)=Major axis (mm)×Minor axis (mm)×Minor axis (mm)/2

The treatment was started when the average tumor size reached about 192 mm$^3$. Randomization was carried out based on the tumor volume on the first day of administration so that the average value of tumor volumes will be approximately equal among the groups. Each group consisted of 10 mice. The day of randomization was denoted as Day 0. From Day 0 through Day 13, mice of each group were treated once daily by each of (i) control (3 mM HCl), (ii) lenvatinib mesilate (10 mg/kg), (iii) sorafenib tosylate (30 mg/kg), or (iv) lenvatinib mesilate (10 mg/kg) plus Antibody B (0.5 mg/mouse). For comparison between two groups, an independent sample t-test has been used.

The combination of Antibody B and lenvatinib mesilate showed significantly superior antitumor effect compared with control group.

Example 9: Comparison of Signal Inhibitory Activity Between Anti-Human Notch4 Polyclonal Antibody and Antibody B Next, signal inhibitory activities of polyclonal anti-human Notch4 antibody (Santa Cruz, SC8643, hereinafter N-17) and Antibody B were compared with Notch4-GAL4 *luciferase* reporter assay system.

Slide-A-Lyzer (Thermo scientific, 66333) was employed to perform dialysis at 4° C. for 8 hours in PBS in order to remove sodium azide contained in N-17. After concentrating the dialyzed N-17 solution with Amicon Ultra (Millipore, UFC503096), and the concentration was measured with a microspectrophotometer (Nano Drop, Thermo).

Recombinant human DLL4 (R&D Systems, 1506-D4-050/CF) was dissolved in PBS to prepare a 10 μg/mL solution (hereinafter DLL4 solution). To a flat-bottomed 96 well white plate (Greiner, 655083), 50 μL/well (500 ng/well) of the DLL4 solution and 50 μL/well of PBS for non-stimulated wells were each dispensed, and this was left overnight at 4° C. to allow DLL4 to be solid phased to the 96-well white plate. The reporter cells were suspended in a D-MEM culture medium comprising 10% Fetal Bovine Serum (FBS) and penicillin/streptomycin to prepare a cell suspension at 1×10$^5$/mL. Each well with solid phased DLL4 was washed three times with PBS, and 50 μL/well (5,000 cells/well) of the cell suspension was seeded. After dialysis/concentration, N-17 dilutions or Antibody B dilutions diluted with the culture medium (final concentrations: 0, 0.01, 0.1, 1, and 10 μg/mL) were each added at 50 μL, and this was cultured at 37° C. for 22 hours. The *luciferase* activity of the reporter cells was evaluated with Steady-Glo Assay System (Promega, E2510) as follows.

One hundred microliters of Steady-Glo solution was added to each well after culturing, stirred, and then left at room temperature for 30 minutes. Luminescence was measured with Multilabel Plate Reader (Envision 2102-0020, Perkin Elmer). Relative luminescence was calculated from the measured luminescence value by the following formula.

Relative luminescence (%)=(Luminescence intensity of the specimen well−Average luminescence intensity of non-stimulated wells)/(Average luminescence intensity of control wells−Average luminescence intensity of non-stimulated wells)

Figure 7:
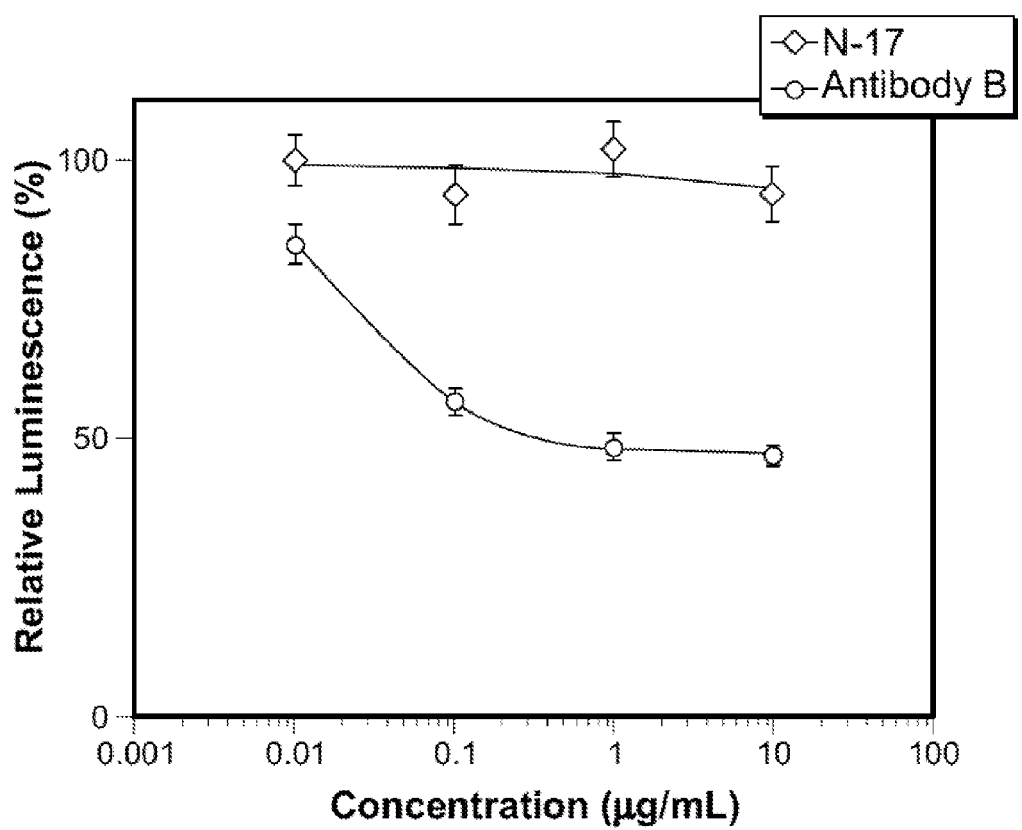
FIG. 7 shows the relationship between the concentration of Antibody B and the relative luminescence (%) value. The graph shows the average value of three independent test results, and the error bar shows the standard deviation thereof.

The relationship between the concentration of Antibody B and the relative luminescence (%) value is shown in FIG. 7. The graph in FIG. 7 shows the average value of three independent test results, and the error bar shows the standard deviation thereof. Signal inhibitory activity was confirmed for Antibody B, but for N-17, Notch4 signal inhibitory activity of N-17 was not seen in the investigated concentration range.

Example 10: Kinetics Analysis of Binding Between Antibody B and Recombinant Soluble Human Notch NRR Domain Kinetics analysis using BIAcore T100 was performed for the interaction between the NRR domain of human Notch isotypes (Notch1, Notch2, Notch3, and Notch4) and Antibody B. Antibody B was purified from the culture supernatant of a stable expression CHO cell line of Antibody B with sequential use of protein A affinity chromatography, Capto Q anion exchange chromatography, and UNOsphere S cation exchange chromatography. Fusion proteins of Human Notch1 NRR domain (Genbank Accession No. 017617; sequence positions 1307-1733), human Notch2 NRR domain (Genbank Accession No. 024408; sequence positions 1239-1650), human Notch3 NRR domain (Genbank Accession No. 000435; sequence positions 1246-1641), and human Notch4 NRR domain (Genbank Accession No. NP_004548.3; sequence positions 1046-1445) with secretory alkaline phosphatase (SEAP), a hemagglutinin (HA) tag, and a histidine tag (×10) were created, and these were purified with HisTrap™ Fast Flow column (GE Healthcare). The interaction between Antibody B and the NRR domain of each human Notch isotypes was measured with the following method. The purified Antibody B was captured by anti-human IgG Fc antibody fixed on a CM5 sensor chip (GE Healthcare). The purified NRR domain of each human Notch isotypes was injected onto the sensor chip at 6 different concentrations, and the interaction and dissociation with the antibody were observed as per operation manual.

The overlaid interaction sensorgram and the calculated kinetics parameters are each shown in FIGS. 8A-8D and Table 32.

TABLE 32

Calculated Kinetic Parameters of Interaction Between Antibody B and Human Notch4-NRR Fusion Proteins

| Sample | Ka (1/Ms) | Kd (1/s) | KD (M) |
|---|---|---|---|
| Human Notch1-NRR-SEAP-HA-His | ND | ND | ND |
| Human Notch2-NRR-SEAP-HA-His | ND | ND | ND |
| Human Notch3-NRR-SEAP-HA-His | ND | ND | ND |
| Human Notch4-NRR-SEAP-HA-His | 2.72E+04 | 8.31E−04 | 3.05E−08 |

The invention claimed is:

1. An anti-Notch4 antibody or a Notch4 binding fragment thereof, wherein said antibody or Notch4 binding fragment thereof comprises a heavy chain variable region and a light chain variable region, wherein:
the heavy chain variable region comprises heavy chain variable region complementarity determining regions CDR1, CDR2, and CDR3 comprising the amino acid sequences set forth in SEQ ID NO:15, SEQ ID NO:17, and SEQ ID NO:19, respectively; and
the light chain variable region comprises light chain variable region complementarity determining regions CDR1, CDR2, and CDR3 comprising the amino acid sequences set forth in SEQ ID NO:20, SEQ ID NO:21, and SEQ ID NO:22, respectively.

2. A pharmaceutical composition comprising the anti-Notch4 antibody or Notch4 binding fragment thereof according to claim 1.

3. The pharmaceutical composition according to claim 2 which further comprises a pharmaceutically acceptable carrier.

4. A method of treating non-small cell lung cancer carcinoma in a human subject in need thereof, comprising administering a therapeutically effective amount of the pharmaceutical composition according to claim 3 to the human subject.

5. A method of treating thyroid cancer in a human subject in need thereof, comprising administering a therapeutically effective amount of the pharmaceutical composition according to claim 3 to the human subject.

6. A method of treating prostate cancer in a human subject in need thereof, comprising administering a therapeutically effective amount of the pharmaceutical composition according to claim 3 to the human subject.

7. A method of treating hepatocellular carcinoma in a human subject in need thereof, comprising administering a therapeutically effective amount of the pharmaceutical composition according to claim 3 to the human subject.

8. An anti-Notch4 antibody or a Notch4 binding fragment thereof, wherein said antibody or Notch4 binding fragment thereof comprises a heavy chain variable region and a light chain variable region, wherein:
the heavy chain variable region comprises heavy chain variable region complementarity determining regions CDR1, CDR2, and CDR3 comprising the amino acid sequences set forth in SEQ ID NO:16, SEQ ID NO:18, and SEQ ID NO:19, respectively; and
the light chain variable region comprises light chain variable region complementarity determining regions CDR1, CDR2, and CDR3 comprising the amino acid sequences set forth in SEQ ID NO:20, SEQ ID NO:21, and SEQ ID NO:22, respectively.

9. A pharmaceutical composition comprising the anti-Notch4 antibody or Notch4 binding fragment thereof according to claim 8.

10. The pharmaceutical composition according to claim 9 which further comprises a pharmaceutically acceptable carrier.

11. A method of treating non-small cell lung cancer carcinoma in a human subject in need thereof, comprising administering a therapeutically effective amount of the pharmaceutical composition according to claim 10 to the human subject.

12. A method of treating thyroid cancer in a human subject in need thereof, comprising administering a therapeutically effective amount of the pharmaceutical composition according to claim 10 to the human subject.

13. A method of treating prostate cancer in a human subject in need thereof, comprising administering a therapeutically effective amount of the pharmaceutical composition according to claim 10 to the human subject.

14. A method of treating hepatocellular carcinoma in a human subject in need thereof, comprising administering a therapeutically effective amount of the pharmaceutical composition according to claim 10 to the human subject.

* * * * *

SEQUENCE LISTING

<160> NUMBER OF SEQ ID NOS: 65

<210> SEQ ID NO 1
<211> LENGTH: 2003
<212> TYPE: PRT
<213> ORGANISM: Homo sapiens

<400> SEQUENCE: 1

```
Met Gln Pro Pro Ser Leu Leu Leu Leu Leu Leu Leu Leu Leu
1               5                   10                  15

Cys Val Ser Val Val Arg Pro Arg Gly Leu Leu Cys Gly Ser Phe Pro
                20                  25                  30

Glu Pro Cys Ala Asn Gly Gly Thr Cys Leu Ser Leu Ser Leu Gly Gln
            35                  40                  45

Gly Thr Cys Gln Cys Ala Pro Gly Phe Leu Gly Glu Thr Cys Gln Phe
        50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
    290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365
```

-continued

```
Thr Cys Ile Asp Arg Val Gly Ser Phe Ser Cys Leu Cys Pro Pro Gly
    370                 375                 380
Arg Thr Gly Leu Leu Cys His Leu Glu Asp Met Cys Leu Ser Gln Pro
385                 390                 395                 400
Cys His Gly Asp Ala Gln Cys Ser Thr Asn Pro Leu Thr Gly Ser Thr
                405                 410                 415
Leu Cys Leu Cys Gln Pro Gly Tyr Ser Gly Pro Thr Cys His Gln Asp
            420                 425                 430
Leu Asp Glu Cys Leu Met Ala Gln Gln Gly Pro Ser Pro Cys Glu His
        435                 440                 445
Gly Gly Ser Cys Leu Asn Thr Pro Gly Ser Phe Asn Cys Leu Cys Pro
450                 455                 460
Pro Gly Tyr Thr Gly Ser Arg Cys Glu Ala Asp His Asn Glu Cys Leu
465                 470                 475                 480
Ser Gln Pro Cys His Pro Gly Ser Thr Cys Leu Asp Leu Leu Ala Thr
                485                 490                 495
Phe His Cys Leu Cys Pro Pro Gly Leu Glu Gly Gln Leu Cys Glu Val
            500                 505                 510
Glu Thr Asn Glu Cys Ala Ser Ala Pro Cys Leu Asn His Ala Asp Cys
        515                 520                 525
His Asp Leu Leu Asn Gly Phe Gln Cys Ile Cys Leu Pro Gly Phe Ser
        530                 535                 540
Gly Thr Arg Cys Glu Glu Asp Ile Asp Glu Cys Arg Ser Ser Pro Cys
545                 550                 555                 560
Ala Asn Gly Gly Gln Cys Gln Asp Gln Pro Gly Ala Phe His Cys Lys
                565                 570                 575
Cys Leu Pro Gly Phe Glu Gly Pro Arg Cys Gln Thr Glu Val Asp Glu
            580                 585                 590
Cys Leu Ser Asp Pro Cys Pro Val Gly Ala Ser Cys Leu Asp Leu Pro
        595                 600                 605
Gly Ala Phe Phe Cys Leu Cys Pro Ser Gly Phe Thr Gly Gln Leu Cys
        610                 615                 620
Glu Val Pro Leu Cys Ala Pro Asn Leu Cys Gln Pro Lys Gln Ile Cys
625                 630                 635                 640
Lys Asp Gln Lys Asp Lys Ala Asn Cys Leu Cys Pro Asp Gly Ser Pro
                645                 650                 655
Gly Cys Ala Pro Pro Glu Asp Asn Cys Thr Cys His His Gly His Cys
            660                 665                 670
Gln Arg Ser Ser Cys Val Cys Asp Val Gly Trp Thr Gly Pro Glu Cys
        675                 680                 685
Glu Ala Glu Leu Gly Gly Cys Ile Ser Ala Pro Cys Ala His Gly Gly
        690                 695                 700
Thr Cys Tyr Pro Gln Pro Ser Gly Tyr Asn Cys Thr Cys Pro Thr Gly
705                 710                 715                 720
Tyr Thr Gly Pro Thr Cys Ser Glu Glu Met Thr Ala Cys His Ser Gly
                725                 730                 735
Pro Cys Leu Asn Gly Gly Ser Cys Asn Pro Ser Pro Gly Gly Tyr Tyr
            740                 745                 750
Cys Thr Cys Pro Pro Ser His Thr Gly Pro Gln Cys Gln Thr Ser Thr
        755                 760                 765
Asp Tyr Cys Val Ser Ala Pro Cys Phe Asn Gly Gly Thr Cys Val Asn
        770                 775                 780
Arg Pro Gly Thr Phe Ser Cys Leu Cys Ala Met Gly Phe Gln Gly Pro
```

```
                    785                 790                 795                 800
            Arg Cys Glu Gly Lys Leu Arg Pro Ser Cys Ala Asp Ser Pro Cys Arg
                            805                 810                 815

Asn Arg Ala Thr Cys Gln Asp Ser Pro Gln Gly Pro Arg Cys Leu Cys
                            820                 825                 830

Pro Thr Gly Tyr Thr Gly Gly Ser Cys Gln Thr Leu Met Asp Leu Cys
                            835                 840                 845

Ala Gln Lys Pro Cys Pro Arg Asn Ser His Cys Leu Gln Thr Gly Pro
                        850                 855                 860

Ser Phe His Cys Leu Cys Leu Gln Gly Trp Thr Gly Pro Leu Cys Asn
            865                 870                 875                 880

Leu Pro Leu Ser Ser Cys Gln Lys Ala Ala Leu Ser Gln Gly Ile Asp
                            885                 890                 895

Val Ser Ser Leu Cys His Asn Gly Gly Leu Cys Val Asp Ser Gly Pro
                        900                 905                 910

Ser Tyr Phe Cys His Cys Pro Pro Gly Phe Gln Gly Ser Leu Cys Gln
                            915                 920                 925

Asp His Val Asn Pro Cys Glu Ser Arg Pro Cys Gln Asn Gly Ala Thr
                        930                 935                 940

Cys Met Ala Gln Pro Ser Gly Tyr Leu Cys Gln Cys Ala Pro Gly Tyr
            945                 950                 955                 960

Asp Gly Gln Asn Cys Ser Lys Glu Leu Asp Ala Cys Gln Ser Gln Pro
                            965                 970                 975

Cys His Asn His Gly Thr Cys Thr Pro Lys Pro Gly Gly Phe His Cys
                        980                 985                 990

Ala Cys Pro Pro Gly Phe Val Gly Leu Arg Cys Glu Gly Asp Val Asp
                        995                 1000                1005

Glu Cys Leu Asp Gln Pro Cys His Pro Thr Gly Thr Ala Ala Cys
                    1010                1015                1020

His Ser Leu Ala Asn Ala Phe Tyr Cys Gln Cys Leu Pro Gly His
                    1025                1030                1035

Thr Gly Gln Trp Cys Glu Val Glu Ile Asp Pro Cys His Ser Gln
                    1040                1045                1050

Pro Cys Phe His Gly Gly Thr Cys Glu Ala Thr Ala Gly Ser Pro
                    1055                1060                1065

Leu Gly Phe Ile Cys His Cys Pro Lys Gly Phe Glu Gly Pro Thr
                    1070                1075                1080

Cys Ser His Arg Ala Pro Ser Cys Gly Phe His His Cys His His
                    1085                1090                1095

Gly Gly Leu Cys Leu Pro Ser Pro Lys Pro Gly Phe Pro Pro Arg
                    1100                1105                1110

Cys Ala Cys Leu Ser Gly Tyr Gly Gly Pro Asp Cys Leu Thr Pro
                    1115                1120                1125

Pro Ala Pro Lys Gly Cys Gly Pro Pro Ser Pro Cys Leu Tyr Asn
                    1130                1135                1140

Gly Ser Cys Ser Glu Thr Thr Gly Leu Gly Gly Pro Gly Phe Arg
                    1145                1150                1155

Cys Ser Cys Pro His Ser Ser Pro Gly Pro Arg Cys Gln Lys Pro
                    1160                1165                1170

Gly Ala Lys Gly Cys Glu Gly Arg Ser Gly Asp Gly Ala Cys Asp
                    1175                1180                1185

Ala Gly Cys Ser Gly Pro Gly Gly Asn Trp Asp Gly Gly Asp Cys
                    1190                1195                1200
```

-continued

```
Ser Leu Gly Val Pro Asp Pro Trp Lys Gly Cys Pro Ser His Ser
1205                1210                1215

Arg Cys Trp Leu Leu Phe Arg Asp Gly Gln Cys His Pro Gln Cys
1220                1225                1230

Asp Ser Glu Glu Cys Leu Phe Asp Gly Tyr Asp Cys Glu Thr Pro
1235                1240                1245

Pro Ala Cys Thr Pro Ala Tyr Asp Gln Tyr Cys His Asp His Phe
1250                1255                1260

His Asn Gly His Cys Glu Lys Gly Cys Asn Thr Ala Glu Cys Gly
1265                1270                1275

Trp Asp Gly Gly Asp Cys Arg Pro Glu Asp Gly Asp Pro Glu Trp
1280                1285                1290

Gly Pro Ser Leu Ala Leu Leu Val Val Leu Ser Pro Pro Ala Leu
1295                1300                1305

Asp Gln Gln Leu Phe Ala Leu Ala Arg Val Leu Ser Leu Thr Leu
1310                1315                1320

Arg Val Gly Leu Trp Val Arg Lys Asp Arg Asp Gly Arg Asp Met
1325                1330                1335

Val Tyr Pro Tyr Pro Gly Ala Arg Ala Glu Glu Lys Leu Gly Gly
1340                1345                1350

Thr Arg Asp Pro Thr Tyr Gln Glu Arg Ala Ala Pro Gln Thr Gln
1355                1360                1365

Pro Leu Gly Lys Glu Thr Asp Ser Leu Ser Ala Gly Phe Val Val
1370                1375                1380

Val Met Gly Val Asp Leu Ser Arg Cys Gly Pro Asp His Pro Ala
1385                1390                1395

Ser Arg Cys Pro Trp Asp Pro Gly Leu Leu Leu Arg Phe Leu Ala
1400                1405                1410

Ala Met Ala Ala Val Gly Ala Leu Glu Pro Leu Leu Pro Gly Pro
1415                1420                1425

Leu Leu Ala Val His Pro His Ala Gly Thr Ala Pro Pro Ala Asn
1430                1435                1440

Gln Leu Pro Trp Pro Val Leu Cys Ser Pro Val Ala Gly Val Ile
1445                1450                1455

Leu Leu Ala Leu Gly Ala Leu Leu Val Leu Gln Leu Ile Arg Arg
1460                1465                1470

Arg Arg Arg Glu His Gly Ala Leu Trp Leu Pro Pro Gly Phe Thr
1475                1480                1485

Arg Arg Pro Arg Thr Gln Ser Ala Pro His Arg Arg Arg Pro Pro
1490                1495                1500

Leu Gly Glu Asp Ser Ile Gly Leu Lys Ala Leu Lys Pro Lys Ala
1505                1510                1515

Glu Val Asp Glu Asp Gly Val Val Met Cys Ser Gly Pro Glu Glu
1520                1525                1530

Gly Glu Glu Val Gly Gln Ala Glu Glu Thr Gly Pro Pro Ser Thr
1535                1540                1545

Cys Gln Leu Trp Ser Leu Ser Gly Gly Cys Gly Ala Leu Pro Gln
1550                1555                1560

Ala Ala Met Leu Thr Pro Pro Gln Glu Ser Glu Met Glu Ala Pro
1565                1570                1575

Asp Leu Asp Thr Arg Gly Pro Asp Gly Val Thr Pro Leu Met Ser
1580                1585                1590
```

-continued

```
Ala Val Cys Cys Gly Glu Val Gln Ser Gly Thr Phe Gln Gly Ala
1595                1600                1605

Trp Leu Gly Cys Pro Glu Pro Trp Glu Pro Leu Leu Asp Gly Gly
1610                1615                1620

Ala Cys Pro Gln Ala His Thr Val Gly Thr Gly Glu Thr Pro Leu
1625                1630                1635

His Leu Ala Ala Arg Phe Ser Arg Pro Thr Ala Ala Arg Arg Leu
1640                1645                1650

Leu Glu Ala Gly Ala Asn Pro Asn Gln Pro Asp Arg Ala Gly Arg
1655                1660                1665

Thr Pro Leu His Ala Ala Val Ala Ala Asp Ala Arg Glu Val Cys
1670                1675                1680

Gln Leu Leu Leu Arg Ser Arg Gln Thr Ala Val Asp Ala Arg Thr
1685                1690                1695

Glu Asp Gly Thr Thr Pro Leu Met Leu Ala Ala Arg Leu Ala Val
1700                1705                1710

Glu Asp Leu Val Glu Glu Leu Ile Ala Ala Gln Ala Asp Val Gly
1715                1720                1725

Ala Arg Asp Lys Trp Gly Lys Thr Ala Leu His Trp Ala Ala Ala
1730                1735                1740

Val Asn Asn Ala Arg Ala Ala Arg Ser Leu Leu Gln Ala Gly Ala
1745                1750                1755

Asp Lys Asp Ala Gln Asp Asn Arg Glu Gln Thr Pro Leu Phe Leu
1760                1765                1770

Ala Ala Arg Glu Gly Ala Val Glu Val Ala Gln Leu Leu Leu Gly
1775                1780                1785

Leu Gly Ala Ala Arg Glu Leu Arg Asp Gln Ala Gly Leu Ala Pro
1790                1795                1800

Ala Asp Val Ala His Gln Arg Asn His Trp Asp Leu Leu Thr Leu
1805                1810                1815

Leu Glu Gly Ala Gly Pro Pro Glu Ala Arg His Lys Ala Thr Pro
1820                1825                1830

Gly Arg Glu Ala Gly Pro Phe Pro Arg Ala Arg Thr Val Ser Val
1835                1840                1845

Ser Val Pro Pro His Gly Gly Ala Leu Pro Arg Cys Arg Thr
1850                1855                1860

Leu Ser Ala Gly Ala Gly Pro Arg Gly Gly Gly Ala Cys Leu Gln
1865                1870                1875

Ala Arg Thr Trp Ser Val Asp Leu Ala Ala Arg Gly Gly Gly Ala
1880                1885                1890

Tyr Ser His Cys Arg Ser Leu Ser Gly Val Gly Ala Gly Gly Gly
1895                1900                1905

Pro Thr Pro Arg Gly Arg Arg Phe Ser Ala Gly Met Arg Gly Pro
1910                1915                1920

Arg Pro Asn Pro Ala Ile Met Arg Gly Arg Tyr Gly Val Ala Ala
1925                1930                1935

Gly Arg Gly Gly Arg Val Ser Thr Asp Asp Trp Pro Cys Asp Trp
1940                1945                1950

Val Ala Leu Gly Ala Cys Gly Ser Ala Ser Asn Ile Pro Ile Pro
1955                1960                1965

Pro Pro Cys Leu Thr Pro Ser Pro Glu Arg Gly Ser Pro Gln Leu
1970                1975                1980

Asp Cys Gly Pro Pro Ala Leu Gln Glu Met Pro Ile Asn Gln Gly
```

```
                1985                1990                1995

Gly Glu  Gly Lys Lys
    2000

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acatcactcc gt                                                          12

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acggagtgat gtccgtcgac gtatctctgc gttgatactt cagcgtagct                 50

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agctacgctg aagtatcaac gcagag                                           26

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccagtggat agactgatgg                                                  20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatggataca gttggtgcag c                                                21

<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Gln Gly Phe Ala Tyr Trp Gly Gln Gly Thr Leu Val Thr
            100                 105                 110

Val Ser Ala
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Trp
                85                  90                  95

Thr Phe Gly Gly Gly Thr Lys Leu Glu Ile Lys
            100                 105

<210> SEQ ID NO 9
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaggtgcagc tggtggagtc tgggggaggc ttagtgcagc ctggagggtc cctgaaactc      60
tcctgtgcag cctctggatt cactttcagt agctatggca tgtcttgggt tcgccagact     120
ccagacaaga ggctggagtt ggtcgcaacc attaatagta atggtggtag aacctattat     180
ccagacagtg tgaagggccg attcaccatc tccagagaca atgccaagaa caccctgtac     240
ctgcaaatga gcagtctgaa gtctgaggac acagccatgt attactgtgc aagagaccag     300

```
ggttttgctt actggggcca agggactctg gtcactgtct ctgca            345
```

<210> SEQ ID NO 10
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gacattgtga tgacccagtc tcacaaattc atgtccacat cagtaggaga cagggtcagc    60
atcacctgca aggccagtca ggatgtgggt actgctgtag cctggtatca acagaaacca   120
gggcaatctc ctaaactact gatttactgg gcatccaccc ggcacactgg agtccctgat   180
cgcttcacag gcagtggatc tgggacagat ttcactctca ccattagcaa tgtgcagtct   240
gaagacttgg cagattattt ctgtcagcaa tatagcagct atccgtggac gttcggtgga   300
ggcaccaagc tggaaatcaa a                                             321
```

<210> SEQ ID NO 11
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Gln Gly Phe Ala Tyr Trp Gly Gln Gly Thr Leu Val Thr
            100                 105                 110

Val Ser Ala Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Ala Ala Ala Pro Ser Val Phe Leu Phe Pro Pro Lys

```
                 225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 13
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
gaggtgcagc tggtggagtc tgggggaggc ttagtgcagc ctggagggtc cctgaaactc      60
tcctgtgcag cctctggatt cactttcagt agctatggca tgtcttgggt tcgccagact     120
ccagacaaga ggctggagtt ggtcgcaacc attaatagta atggtggtag aacctattat     180
ccagacagtg tgaagggccg attcaccatc tccagagaca atgccaagaa caccctgtac     240
ctgcaaatga gcagtctgaa gtctgaggac acagccatgt attactgtgc aagagaccag     300
ggttttgctt actggggcca agggactctg gtcactgtct ctgcagctag cacaaaaggc     360
ccctctgtct tccctctggc tccctgctcc cgctccacct ccgagtccac tgccgctctg     420
ggctgtctgg tcaaggatta cttccctgag ccagtcactg tgagttggaa ctcaggcgcc     480
ctgaccagcg gagtccacac atttccggct gtgctgcaga gctccggcct gtactccctg     540
tctagtgtgt caccgtgcc ttcaagcaat ttcgggactc agacctatac atgcaacgtg     600
gaccataagc catctaatac taaggtcgat aaaaccgtgg agcgaaaatg ctgcgtggaa     660
tgcccacctt gtcctgctcc accagccgct gcaccaagcg tgttcctgtt tcctccaaag     720
cccaaagaca cactgatgat cagcagaact cctgaggtca cctgcgtggt cgtggacgtg     780
tcccacgagg atcccgaagt ccagtttaac tggtacgtgg atggggtcga agtgcataat     840
gcaaagacta aacctcggga ggaacagttc aactctacct ttagagtcgt gagtgtgctg     900
acagtcgtgc accaggactg gctgaacgga aaggagtata agtgcaaagt gtctaataag     960
ggcctgcccg cccctatcga gaaacaatt agtaagacta aaggccagcc aagggaaccc    1020
caggtgtaca cactgccccc tagtcgcgag gaaatgacaa agaaccaggt ctcactgact    1080
tgtctggtga aagggttcta tccatccgac attgccgtgg agtgggaatc taatggacag    1140
cccgaaaaca attacaagac cacaccaccc atgctggaca gcgatggatc cttctttctg    1200
tattcaaagc tgaccgtgga taaagccgg tggcagcagg gcaatgtctt ttcctgctct    1260
gtgatgcacg aagccctgca caaccactac actcagaagt ccctgtccct gtctcctggc    1320
aaatga                                                              1326
```

<210> SEQ ID NO 14
<211> LENGTH: 645
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 14

```
gacattgtga tgacccagtc tcacaaattc atgtccacat cagtaggaga cagggtcagc    60
atcacctgca aggccagtca ggatgtgggt actgctgtag cctggtatca acagaaacca   120
gggcaatctc ctaaactact gatttactgg gcatccaccc ggcacactgg agtccctgat   180
cgcttcacag gcagtggatc tgggacagat ttcactctca ccattagcaa tgtgcagtct   240
gaagacttgg cagattattt ctgtcagcaa tatagcagct atccgtggac gttcggtgga   300
ggcaccaagc tggaaatcaa acgtacggtc gccgcccct ccgtgtttat ttttcctcca    360
tctgacgaac agctgaagag tgggaccgcc tccgtggtgt gcctgctgaa caatttctac   420
cccgggagg ccaaggtgca gtggaaagtc gacaacgctc tgcagtctgg caatagtcag    480
gagtcagtga ctgaacagga cagcaaggat tccacctatt ctctgagctc caccctgaca   540
ctgagcaaag cagattacga aaagcacaaa gtctatgcct gcgaagtgac ccaccagggg   600
ctgagcagtc cagtgaccaa gtcctttaac aggggagagt gttga                   645
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Tyr Gly Met Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Thr Phe Ser Ser Tyr Gly Met Ser
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ile Asn Ser Asn Gly Gly Arg Thr Tyr Tyr Pro Asp Ser Val Lys
1               5                   10                  15
Gly

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 18

Thr Ile Asn Ser Asn Gly Gly Arg Thr Tyr
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Gln Gly Phe Ala Tyr
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ala Ser Gln Asp Val Gly Thr Ala Val Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Ala Ser Thr Arg His Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Tyr Ser Ser Tyr Pro Trp Thr
1               5

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agctatggca tgtct                                                      15

<210> SEQ ID NO 24
<211> LENGTH: 30
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 24
ggattcactt tcagtagcta tggcatgtct                                      30

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
accattaata gtaatggtgg tagaacctat tatccagaca gtgtgaaggg c              51

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
accattaata gtaatggtgg tagaacctat                                      30

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaccagggtt ttgcttac                                                   18

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaggccagtc aggatgtggg tactgctgta gcc                                  33

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgggcatcca cccggcacac t                                               21

<210> SEQ ID NO 30
<211> LENGTH: 27
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 30
cagcaatata gcagctatcc gtggacg                                              27

<210> SEQ ID NO 31
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Tyr Val
        35                  40                  45

Ser Thr Ile Asn Ser Asn Gly Gly Arg Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Asp Gln Gly Phe Ala Tyr Trp Gly Gln Gly Thr Leu Val Thr
            100                 105                 110

Val Ser Ser
        115

<210> SEQ ID NO 32
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaggtgcagc tggtcgagag cggagggggg ctggtgcagc caggagggtc tctgaggctg     60
agttgcgccg cttcaggctt caccttcagc tcctacggga tgtcttgggt gcgccaggct    120
ccagggaagg gactggagta tgtcagcacc atcaactcca atggaggccg aacatactat    180
cctgactccg tgaagggccg gttcactatc tctagagata acagtaagaa caccctgtac    240
ctgcagatgg gcagcctgag agcagaagac atggccgtct actattgtgc aagggatcag    300
ggattcgcat actggggaca gggaactctg gtgaccgtct caagc                    345

<210> SEQ ID NO 33
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ser Thr Ile Asn Ser Asn Gly Gly Arg Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Asp Gln Gly Phe Ala Tyr Trp Gly Gln Gly Thr Leu Val Thr
            100                 105                 110

Val Ser Ser
        115

<210> SEQ ID NO 34
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gaagtgcagc tggtcgagag cggggagggg ctggtgcagc caggagggtc tctgaggctg      60
agttgcgccg cttcaggctt caccttcagc tcctacggga tgtcttgggt gcgccaggct     120
ccagggaagg gactggagct ggtcagcacc atcaactcca atggaggccg aacatactat     180
cctgactccg tgaagggccg gttcactatc tctagagata acagtaagaa caccctgtat     240
ctgcagatgg gcagcctgag agcagaagac atggccgtct actattgtgc ccgagatcag     300
gggttcgctt attggggaca ggggacactg gtgaccgtga gcagc                     345

<210> SEQ ID NO 35
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Thr Ile Asn Ser Asn Gly Gly Arg Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Lys Ala Glu Asp Met Ala Val Tyr Tyr Cys
                85                  90                  95

Ala Arg Asp Gln Gly Phe Ala Tyr Trp Gly Gln Gly Thr Leu Val Thr
            100                 105                 110

Val Ser Ser
        115

<210> SEQ ID NO 36
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gaagtgcagc tggtcgagag tgggggaggc ctggtgcagc caggagggtc tctgaggctg     60
agttgcgccg cttcaggctt caccttcagc tcctacggga tgtcctgggt gcgccaggct    120
ccagggaaag gactggagct ggtcgccacc atcaactcta atggaggccg aacatactat    180
cctgacagtg tgaagggccg gttcactatt agcagagata actccaaaaa taccctgtat    240
ctgcagatgg gcagcctgaa ggcagaagac atggccgtct actattgtgc tcgggatcag    300
gggttcgcct attgggggca ggggactctg gtcactgtct cttcc                    345

<210> SEQ ID NO 37
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Tyr Val
        35                  40                  45

Ser Thr Ile Asn Ser Asn Gly Gly Arg Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Asp Gln Gly Phe Ala Tyr Trp Gly Gln Gly Thr Leu Val Thr
            100                 105                 110

Val Ser Ser
        115

<210> SEQ ID NO 38
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gaagtgcagc tggtcgaatc tgggggggga ctggtgcagc caggagggtc tctgaggctg     60
agttgcgccg cttcaggctt caccttcagc tcctacggga tgtcttgggt gcgccaggct    120
cctgggaagg gactggagta tgtcagcacc atcaactcca atggaggccg aacatactat    180
gccaactccg tgaagggccg gttcactatc tctagagaca acgtaagaa cacccctgtac   240 ctgcagatgg gcagcctgag agcagaagat atggccgtct actattgtgc tcgggatcag    300

```
ggctttgctt attggggaca ggggacactg gtcaccgtct cctcc              345
```

<210> SEQ ID NO 39
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ser Thr Ile Asn Ser Asn Gly Gly Arg Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Asp Gln Gly Phe Ala Tyr Trp Gly Gln Gly Thr Leu Val Thr
            100                 105                 110

Val Ser Ser
        115

<210> SEQ ID NO 40
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
gaggtgcagc tggtcgaatc cggggggggg ctggtgcagc caggagggtc tctgaggctg     60
agttgcgccg cttcaggctt caccttcagc tcctacggga tgtcttgggt gcgccaggct    120
cctgggaagg gactggagct ggtcagcacc atcaactcca atggaggccg aacatactat    180
gccaactccg tgaagggccg gttcactatc tctagagaca cagtaagaa caccctgtat     240 ctgcagatgg gcagcctgag agcagaagat atggccgtct actattgtgc tcgggatcag    300
ggcttcgcct actgggggca gggaacactg gtcaccgtct cctca                    345
```

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Val Pro Lys Leu Leu Ile
        35                  40                  45

```
Tyr Trp Ala Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Ser Ser Tyr Pro Trp
                85                  90                  95

Thr Phe Gly Gln Gly Thr Lys Val Glu Ile Lys
            100                 105

<210> SEQ ID NO 42
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gacattcaga tgacacagag cccttcatct ctgagtgcat cagtgggaga cagggtcacc      60
atcacatgca aagccagcca ggatgtggga accgcagtcg cttggtacca gcagaagccc     120
gggaaagtgc ctaagctgct gatctactgg gctagtacac ggcacactgg cgtcccatcc     180
agattcagcg gctccgggtc tggaaccgac tttactctga ccatcagctc cctgcagccc     240
gaggatgtgg ccacatacta ttgccagcag tattcatctt atccttggac cttcggacag     300
ggaacaaaag tggaaatcaa a                                               321

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Gly Thr Ala
                20                  25                  30

Val Ala Trp Tyr Gln Gln Lys Pro Gly Lys Val Pro Lys Leu Leu Ile
             35                  40                  45

Tyr Trp Ala Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Val Ala Thr Tyr Phe Cys Gln Gln Tyr Ser Ser Tyr Pro Trp
                85                  90                  95

Thr Phe Gly Gln Gly Thr Lys Val Glu Ile Lys
            100                 105

<210> SEQ ID NO 44
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
```

```
gatattcaga tgactcagag cccctcctct ctgagtgcat cagtgggaga cagggtcacc    60
atcacatgca aagccagcca ggatgtggga accgcagtcg cttggtacca gcagaagccc   120
gggaaagtgc ctaagctgct gatctactgg gctagtacac ggcacactgg cgtcccatcc   180
agattcagcg gctccgggtc tggaaccgac tttactctga ccatcagctc cctgcagccc   240
gaggatgtgg ccacatactt ctgccagcag tattcatcct atccttggac cttcggacag   300
ggaactaaag tggagattaa g                                             321
```

```
<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Trp
                85                  90                  95

Thr Phe Gly Gln Gly Thr Lys Val Glu Ile Lys
            100                 105

```
<210> SEQ ID NO 46
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gaaattgtga tgacccagtc tcccgccaca ctgtctgtga gtccaggaga gagggcaact    60
ctgtcttgca aggccagtca ggacgtggga accgcagtcg cttggtacca gcagaaaccc   120
gggcaggctc ctcggctgct gatctattgg gcatccactc ggcacaccgg cattcccgcc   180
agattctcag gcagcgggtc cggaacagag tttaccctga caatcagctc cctgcagagc   240
gaagatttcg ctgtctacta ttgccagcag tattctagtt atccttggac attcggccag   300
ggaacaaaag tggaaatcaa a                                             321
```

```
<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

Glu Ile Val Met Thr Gln Ser Pro Ala Thr Leu Ser Val Ser Pro Gly

```
1               5                   10                  15
Glu Arg Ala Thr Leu Ser Cys Lys Ala Ser Gln Asp Val Gly Thr Ala
                    20                  25                  30

Val Ala Trp Tyr Gln Gln Lys Pro Gly Gln Ala Pro Arg Leu Leu Ile
            35                  40                  45

Tyr Trp Ala Ser Thr Arg His Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Trp
                85                  90                  95

Thr Phe Gly Gln Gly Thr Lys Val Glu Ile Lys
            100                 105
```

<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
gaaatcgtga tgacccagag ccccgcaaca ctgtctgtga gtccaggaga gagggcaact    60
ctgtcttgca aggccagtca ggacgtggga accgcagtcg cttggtacca gcagaaaccc   120
gggcaggctc ctcggctgct gatctattgg gcatccactc ggcacaccgg cattcccgcc   180
agattctcag gcagcgggtc cggaacagag tttaccctga caatcagctc cctgcagagc   240
gaagatttcg ctgtctactt ttgccagcag tattcatcct atccttggac cttcggacag   300
ggaacaaaag tggaaatcaa a                                             321
```

<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
                    20                  25                  30

Val Ala Trp Tyr Gln Gln Lys Pro Gly Lys Ser Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Ser Ser Tyr Pro Trp
                85                  90                  95

Thr Phe Gly Gln Gly Thr Lys Val Glu Ile Lys
            100                 105
```

<210> SEQ ID NO 50
<211> LENGTH: 321
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 50

```
gatatccaga tgacccagtc cccaagctcc ctgtccgcat ctgtgggcga ccgggtcacc      60
attacatgta aagccagtca ggatgtggga acagccgtcg cttggtacca gcagaagccc     120
ggcaaatctc ctaagctgct gatctattgg cttccacac ggcacactgg cgtgccctct     180
agattcagtg gctcagggag cggaacagac tttactctga ccatttctag tctgcagcca     240
gaggatgtgg caacttactt ctgccagcag tactcaagct atccctggac ctttggccag     300
gggacaaaag tcgaaatcaa g                                               321
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Gly Thr Ala
            20                  25                  30

Val Ala Trp Tyr Gln Gln Lys Pro Gly Gln Ser Pro Arg Leu Leu Ile
        35                  40                  45

Tyr Trp Ala Ser Thr Arg His Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Trp
                85                  90                  95

Thr Phe Gly Gln Gly Thr Lys Val Glu Ile Lys
            100                 105
```

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
gaaatcgtga tgacccagag ccccgcaaca ctgtctgtga gtccaggaga gagggcaact      60
ctgtcttgca aggccagtca ggacgtggga accgcagtcg cttggtacca gcagaaaccc     120
gggcagtctc ctcggctgct gatctattgg catccactc ggcacaccgg cattcccgcc     180
agattctcag gcagcgggtc cggaacagag tttaccctga caatcagctc cctgcagagc     240
gaagatttcg ctgtctactt ttgccagcag tattcatcct atccttggac cttcggacag     300
ggaacaaaag tggaaatcaa a                                               321
```

<210> SEQ ID NO 53
<211> LENGTH: 326
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 54
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
```

```
gctagcacaa aaggcccctc tgtcttccct ctggctccct gctcccgctc cacctccgag      60
tccactgccg ctctgggctg tctggtcaag gattacttcc ctgagccagt cactgtgagt     120
tggaactcag gcgccctgac cagcggagtc cacacatttc cgctgtgct gcagagctcc     180 ggcctgtact ccctgtctag tgtggtcacc gtgccttcaa gcaatttcgg gactcagacc     240
tatacatgca acgtggacca taagccatct aatactaagg tcgataaaac cgtggagcga     300
aaatgctgcg tggaatgccc accttgtcct gctccaccag ccgctgcacc aagcgtgttc     360
ctgtttcctc caaagcccaa agacacactg atgatcagca gaactcctga ggtcacctgc     420
gtggtcgtgg acgtgtccca cgaggatccc gaagtccagt ttaactggta cgtggatggg     480
gtcgaagtgc ataatgcaaa gactaaacct cgggaggaac agttcaactc tacctttaga     540
gtcgtgagtg tgctgacagt cgtgcaccag gactggctga acggaaagga gtataagtgc     600
aaagtgtcta ataagggcct gcccgcccct atcgagaaaa caattagtaa gactaaaggc     660
cagccaaggg aacccaggt gtacacactg cccctagtc gcgaggaaat gacaaagaac     720
caggtctcac tgacttgtct ggtgaaaggg ttctatccat ccgacattgc cgtggagtgg     780
gaatctaatg gacagcccga aaacaattac aagaccacac cacccatgct ggacagcgat     840
ggatccttct ttctgtattc aaagctgacc gtggataaaa gccggtggca gcagggcaat     900
gtcttttcct gctctgtgat gcacgaagcc ctgcacaacc actacactca gaagtccctg     960
tccctgtctc ctggcaaatg a                                              981
```

<210> SEQ ID NO 55
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

Ser Thr Phe Arg Val Val Ser Val Leu Thr Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly
                325

<210> SEQ ID NO 56
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gctagcacaa aaggcccctc tgtcttccct ctggctccct gctcccgctc cacctccgag     60
tccactgccg ctctgggctg tctggtcaag gattacttcc ctgagccagt cactgtgagt    120
tggaactcag gcgccctgac cagcggagtc cacacatttc ccgctgtgct gcagagctcc    180
ggcctgtact ccctgtctag tgtggtcacc gtgccttcaa gcaatttcgg gactcagacc    240
tatacatgca acgtggacca taagccatct aatactaagg tcgataaaac cgtggagcga    300
aaatgctgcg tggaatgccc accttgtcct gctccaccag ccgctgcacc aagcgtgttc    360
ctgtttcctc caaagcccaa agacacactg atgatcagca aactcctga ggtcacctgc    420 gtggtcgtgg acgtgtccca cgaggatccc gaagtccagt ttaactggta cgtggatggg    480
gtcgaagtgc ataatgcaaa gactaaacct cgggaggaac agttcaactc tacctttaga    540
gtcgtgagtg tgctgacagt cgtgcaccag gactggctga acggaaagga gtataagtgc    600
aaagtgtcta ataagggcct gcccgcccct atcgagaaaa caattagtaa gactaaaggc    660
cagccaaggg aaccccaggt gtacacactg cccctagtc gcgaggaaat gacaaagaac    720
caggtctcac tgacttgtct ggtgaaaggg ttctatccat ccgacattgc cgtggagtgg    780
gaatctaatg gacagcccga aaacaattac aagaccacac acccatgct ggacagcgat    840 ggatccttct ttctgtattc aaagctgacc gtggataaaa gccggtggca gcagggcaat    900
gtcttttcct gctctgtgat gcacgaagcc ctgcacaacc actacactca gaagtccctg    960
tccctgtctc ctggctga                                                  978

<210> SEQ ID NO 57
<211> LENGTH: 107
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 57

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 58
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
cgtacggtcg ccgcccctc cgtgtttatt tttcctccat ctgacgaaca gctgaagagt     60
gggaccgcct ccgtggtgtg cctgctgaac aatttctacc cccgggaggc caaggtgcag    120
tggaaagtcg acaacgctct gcagtctggc aatagtcagg agtcagtgac tgaacaggac    180
agcaaggatt ccacctattc tctgagctcc accctgacac tgagcaaagc agattacgaa    240
aagcacaaag tctatgcctg cgaagtgacc caccaggggc tgagcagtcc agtgaccaag    300
tcctttaaca ggggagagtg ttga                                           324

<210> SEQ ID NO 59
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gaagtgcagc tggtcgaatc tgggggggt ctggtgcagc caggcggatc cctgagactg      60
agctgcgccg cttctgggtt cacatttcc agctacggca tgtcctgggt ccgccaggct     120
ccaggcaagg gactggagct ggtgagtaca atcaactcaa atggggggtcg aacttactat    180 cccgactccg tgaagggcag gttcactatt tcccgggata cagcaaaaa taccctgtac     240 ctgcagatgg ggtccctgcg agctgaagac atggcagtgt actattgtgc ccgtgatcag    300
ggtttcgctt attgggggca gggtactctg gtcaccgtgt ctagtgcttc taccaaggga    360
ccatccgtgt tcccactggc accatgctcc cggagcacat ctgagagtac tgcagccctg    420
ggctgtctgg tgaaggacta tttccctgaa ccagtcacag tgagctggaa ctctggcgca    480
ctgacaagcg gagtccacac ttttcctgcc gtgctgcagt catccggcct gtactctctg    540

```
agctctgtgg tcactgtccc cagttcaaat ttcggaactc agacctatac atgcaacgtg      600
gaccataagc ctagcaatac caaggtcgat aaaacagtgg agcgtaaatg ctgcgtggaa      660
tgcccacctt gtccagcacc accagctgca gccccttccg tgttcctgtt tcctccaaag      720
ccaaaagaca ccctgatgat ctctagaacc cccgaggtca catgcgtggt cgtggacgtg      780
agtcacgagg atcctgaagt ccagtttaac tggtacgtgg atggcgtcga agtgcataat      840
gccaagacaa aaccaagaga ggaacagttc aactcaacct ttcgcgtcgt gtccgtgctg      900
acagtcgtgc accaggattg gctgaacggc aaggagtata agtgcaaagt gtccaataag      960
ggactgcccg ctcctatcga gaaaactatt tccaagacca aggacagcc  tagggaacca     1020 caggtgtaca ctctgccccc ttcccgggag gaaatgacta agaaccaggt cagcctgacc     1080
tgtctggtga aagggttcta tcctagtgac attgccgtgg agtgggaatc aaatggtcag     1140
ccagagaaca attacaagac cacaccaccc atgctggaca gtgatggctc attctttctg     1200
tatagcaagc tgaccgtcga taaatctagg tggcagcagg gaaacgtgtt ctcctgctcc     1260
gtgatgcacg aagcactgca caaccattac acccagaaat ccctgagcct gtccccggc      1320 tga                                                                   1323

<210> SEQ ID NO 60
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gaggtgcagc tggtcgagtc cgggggggt ctggtgcagc caggaggatc cctgaggctg       60
agctgcgccg cttctgggtt cacattttcc agctacggca tgtcctgggt ccggcaggca      120
ccaggcaagg gactggagct ggtggccaca atcaacagta tggggggtag aacttactat      180
cccgactcag tgaagggcag gttcactatt agtcgggata actcaaaaaa taccctgtac      240
ctgcagatgg gtccctgaa  ggctgaagac atggcagtgt actattgtgc ccgcgatcag      300
ggtttcgctt attgggggca gggtactctg gtcaccgtgt ctagtgcctc caccaagggg      360
cccagcgtgt ttccactggc tccctgctcc gaagcacat  ctgagagtac tgcagccctg      420
ggctgtctgg tgaaggacta tttccctgaa ccagtcacag tgagctggaa ctctggcgct      480
ctgacatctg gagtccacac ttttcctgca gtgctgcagt catccggcct gtactccctg      540
agctctgtgg tcactgtccc cagttcaaat ttcggaactc agacctatac atgcaacgtg      600
gaccataaac ctagcaatac caaggtcgat aaaacagtgg agcggaagtg ctgtgtggaa      660
tgcccacctt gtccagctcc accagctgca gccccttctg tgttcctgtt tcctccaaag      720
ccaaaagaca ccctgatgat cagcaggacc cccgaggtca catgtgtggt cgtggacgtg      780
tctcacgagg atcctgaagt ccagtttaac tggtacgtgg atggcgtcga agtgcataat      840
gcaaagacaa aaccaagaga ggaacagttc aactctacct ttcgcgtcgt gagtgtgctg      900
acagtcgtgc accaggattg gctgaacggc aaggagtata agtgcaaagt gtccaataag      960
ggactgcccg cccctatcga gaaaactatt agcaagacca aggacagcc  tcgagaacca     1020 caggtgtaca ctctgccccc tagtcgtgag gaaatgacta agaaccaggt ctccctgacc     1080
tgtctggtga aagggttcta tcctagcgac attgccgtgg agtgggaatc taatggtcag     1140
ccagagaaca attacaagac cacaccaccc atgctggaca gtgatggctc attctttctg     1200
```

```
tattcaaagc tgaccgtcga taaatccagg tggcagcagg gaaatgtgtt ttcatgctcc    1260
gtgatgcacg aagccctgca caaccattac acccagaaga gcctgtccct gagccccggc    1320
tga                                                                 1323
```

<210> SEQ ID NO 61
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gaagtgcagc tggtcgagtc tgggggggg  ctggtgcagc ctggcggatc cctgagactg     60
agctgcgccg cttctgggtt cacattttcc agctacggca tgtcctgggt ccgccaggca    120
ccaggcaagg gactggagct ggtgagtaca atcaactcaa atggggggtcg aacttactat   180 gctaactccg tgaagggcag gttcactatt tcccgggaca cagcaaaaa  taccctgtac    240 ctgcagatgg ggtccctgcg agctgaagac atggcagtgt actattgtgc ccgtgatcag    300 ggttttcgctt attgggggca gggtactctg gtcaccgtgt ctagtgcttc taccaagggg   360
cccagtgtgt ttccactggc accctgctcc cggagcacat ctgagagtac tgcagccctg    420
ggctgtctgg tgaaggatta tttccctgaa ccagtcacag tgagctggaa ctctggcgca    480
ctgacaagcg gagtccacac ttttcctgcc gtgctgcagt catccggcct gtactctctg    540
agctctgtgt tcactgtccc cagttcaaat ttcggaactc agacctatac atgcaacgtg    600
gaccataagc ctagcaatac caaggtcgat aaaacagtgg agcgtaaatg ctgtgtggaa    660
tgcccacctt gtccagctcc accagctgca gccccttctg tgttcctgtt tcctccaaag    720
ccaaaagaca ccctgatgat ctctagaacc cccgaggtca catgtgtggt cgtggacgtc    780
agtcacgagg atccagaagt ccagtttaac tggtacgtgg atggcgtcga agtgcataat    840
gcaaagacaa aacccagaga ggaacagttc aactcaacct ttcgcgtcgt gtccgtgctg    900
acagtcgtgc accaggactg gctgaacgga aaggagtata gtgcaaagt  gtccaataag    960 ggactgcccg cccctatcga gaaaactatt tccaagacca aggacagcc  tagggaacca   1020 caggtgtaca ctctgccccc ttcccgggag gaaatgacta agaaccaggt cagcctgacc   1080
tgtctggtga aagggttcta tcctagtgac attgccgtgg agtgggaatc aaatggtcag   1140
ccagagaaca attacaagac cacaccaccc atgctggaca gtgatggctc attcttttctg  1200 tatagcaagc tgaccgtcga taaatctagg tggcagcagg gaaatgtgtt ttcatgctcc   1260
gtgatgcacg aagccctgca caaccactac acacagaaaa gcctgagcct gagccccggc   1320
tga                                                                1323
```

<210> SEQ ID NO 62
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gaaatcgtga tgactcagtc ccccgctaca ctgagcgtgt ctcccggaga gagagctact     60
ctgtcttgca aggcaagtca ggacgtggga actgcagtcg cctggtacca gcagaaacca    120
```

| ggacaggcac cacgactgct gatctattgg gctagtacaa ggcacactgg cattcctgcc | 180 |
| cggttcagtg gctcaggatc cgggacagag tttaccctga caatctccag cctgcagtcc | 240 |
| gaagatttcg ctgtgtacta ttgccagcag tactctagtt atccttggac ctttggtcag | 300 |
| ggcacaaagg tcgagatcaa acgaaccgtg gccgctccaa gcgtcttcat tttteccect | 360 |
| tctgacgaac agctgaagtc aggtacagcc tccgtggtct gtctgctgaa caatttctac | 420 |
| ccaagggagg caaaggtgca gtggaaagtc gataacgccc tgcagagcgg caattctcag | 480 |
| gagagtgtga ctgaacagga ctcaaaggat tccacctata gcctgtcatc cactctgacc | 540 |
| ctgagcaaag ctgactacga aaagcataaa gtgtatgcat gtgaagtcac acaccagggt | 600 |
| ctgagttctc cagtcaccaa atcttttaat agaggcgagt gctga | 645 |

<210> SEQ ID NO 63
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| gaaatcgtga tgacccagtc tcctgctaca ctgagcgtgt ctcccggaga gagagctact | 60 |
| ctgtcttgca aggcaagtca ggacgtggga actgcagtcg cctggtacca gcagaaacca | 120 |
| ggacaggcac cacgactgct gatctattgg gctagtacaa ggcacactgg cattcctgcc | 180 |
| cggttcagtg gctcaggatc cgggacagag tttaccctga caatctccag cctgcagtcc | 240 |
| gaagatttcg ctgtgtactt tgccagcag tactctagtt atccttggac cttcggtcag | 300 |
| ggcacaaagg tcgagatcaa acgaaccgtg gccgctccaa gcgtcttcat tttteccect | 360 |
| tctgacgaac agctgaagtc aggtacagcc tccgtggtct gtctgctgaa caattttac | 420 |
| ccaagggagg caaaggtgca gtggaaagtc gataacgccc tgcagagcgg caattctcag | 480 |
| gagagtgtga ctgaacagga ctcaaaggat tccacctata gcctgtcatc cactctgacc | 540 |
| ctgagcaaag ctgactacga aaagcataaa gtgtatgcat gtgaagtcac acaccagggt | 600 |
| ctgtccagtc cagtcaccaa atcctttaat cggggagagt gctga | 645 |

<210> SEQ ID NO 64
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

| gatattcaga tgacccagtc tccttccagc ctgtctgcaa gtgtgggaga cagggtcacc | 60 |
| atcacatgca aagcctccca ggatgtggga accgcagtcg cctggtacca gcagaagcca | 120 |
| gggaaaagcc ccaagctgct gatctactgg gcttctacca gcacacagg cgtgccaagt | 180 |
| cggttctcag gctccggaag cgggaccgac tttactctga ccatctccag cctgcagcct | 240 |
| gaggatgtgg caacatactt ctgccagcag tactctagtt atccatggac ttttggtcag | 300 |
| ggcaccaaag tcgagatcaa agaactgtg gccgctccct ccgtcttcat tttccccct | 360 |
| agcgacgaac agctgaagag tggtacagcc tcagtggtct gtctgctgaa caatttctac | 420 |
| cctagggagg ctaaagtgca gtggaaggtc gataacgcac tgcagtctgg caatagtcag | 480 |
| gagtcagtga cagaacagga ctccaaagat agcacttatt ctctgtcatc cacactgact | 540 |

-continued

```
ctgtctaagg ccgactacga aaagcataaa gtgtatgctt gtgaggtcac acaccagggt      600
ctgagcagtc cagtcaccaa gagctttaac cgaggagagt gctga                     645

<210> SEQ ID NO 65
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gaaatcgtga tgacccagtc tcctgctaca ctgagcgtgt ctcccggaga gagagctact      60
ctgtcttgca aggcaagtca ggacgtggga actgcagtcg cctggtacca gcagaaacca     120
gggcagagtc cccgcctgct gatctattgg gcctccacaa ggcacactgg cattcctgct     180
cggttcagtg gctcaggatc cgggacagag tttaccctga caatctccag cctgcagagc     240
gaagatttcg ccgtgtactt ttgccagcag tactctagtt atccttggac cttcggtcag     300
ggcacaaagg tcgagatcaa acgaaccgtg gccgctccaa gcgtcttcat ttttcccct      360 tctgacgaac agctgaagtc aggtacagct tccgtggtct gtctgctgaa caattttac     420 ccaagggagg caaaggtgca gtggaaagtc gataacgccc tgcagagcgg caattctcag     480
gagagtgtga ctgaacagga ctcaaaggat tccacctata gcctgtcatc cactctgacc     540
ctgtctaaag ctgactacga aaagcataaa gtgtatgcat gtgaagtcac ccaccagggg     600
ctgagtagtc cagtcaccaa gagttttaat cggggcgagt gttga                    645
```